United States Patent
Masuyama et al.

(10) Patent No.: US 10,670,963 B2
(45) Date of Patent: Jun. 2, 2020

(54) SALT AND PHOTORESIST COMPOSITION CONTAINING THE SAME

(71) Applicant: SUMITOMO CHEMICAL COMPANY, LIMITED, Tokyo (JP)

(72) Inventors: Tatsuro Masuyama, Osaka (JP); Satoshi Yamaguchi, Osaka (JP); Koji Ichikawa, Osaka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 78 days.

(21) Appl. No.: 15/911,804

(22) Filed: Mar. 5, 2018

(65) Prior Publication Data

US 2018/0259851 A1 Sep. 13, 2018

(30) Foreign Application Priority Data

Mar. 8, 2017 (JP) .................... 2017-043568

(51) Int. Cl.
| | |
|---|---|
| *G03F 7/004* | (2006.01) |
| *G03F 7/38* | (2006.01) |
| *C07C 303/32* | (2006.01) |
| *C07C 309/04* | (2006.01) |
| *C07C 309/06* | (2006.01) |
| *C07C 309/17* | (2006.01) |
| *C07C 309/19* | (2006.01) |
| *C07C 381/12* | (2006.01) |
| *C07D 317/16* | (2006.01) |
| *C07D 317/24* | (2006.01) |
| *C07D 317/26* | (2006.01) |
| *C07D 319/04* | (2006.01) |
| *C07D 319/06* | (2006.01) |
| *C07D 319/08* | (2006.01) |
| *C07C 321/28* | (2006.01) |
| *G03F 7/038* | (2006.01) |
| *G03F 7/32* | (2006.01) |
| *G03F 7/16* | (2006.01) |
| *G03F 7/20* | (2006.01) |
| *G03F 7/039* | (2006.01) |

(52) U.S. Cl.
CPC .......... *G03F 7/0045* (2013.01); *C07C 303/32* (2013.01); *C07C 309/04* (2013.01); *C07C 309/06* (2013.01); *C07C 309/17* (2013.01); *C07C 309/19* (2013.01); *C07C 321/28* (2013.01); *C07C 381/12* (2013.01); *C07D 317/16* (2013.01); *C07D 317/24* (2013.01); *C07D 317/26* (2013.01); *C07D 319/04* (2013.01); *C07D 319/06* (2013.01); *C07D 319/08* (2013.01); *G03F 7/0046* (2013.01); *G03F 7/038* (2013.01); *G03F 7/039* (2013.01); *G03F 7/0392* (2013.01); *G03F 7/0397* (2013.01); *G03F 7/162* (2013.01); *G03F 7/168* (2013.01); *G03F 7/2006* (2013.01); *G03F 7/327* (2013.01); *G03F 7/38* (2013.01); *C07C 2603/74* (2017.05)

(58) Field of Classification Search
CPC .... G03F 7/0045; G03F 7/0392; G03F 7/0397; G03F 7/38; C07C 303/32; C07C 309/04; C07C 309/06; C07C 309/17; C07C 309/19; C07C 381/12; C07D 317/16; C07D 317/24; C07D 317/26; C07D 319/04; C07D 319/06; C07D 319/08
See application file for complete search history.

(56) References Cited

U.S. PATENT DOCUMENTS

| 9,229,321 B2 * | 1/2016 | Masuyama | G03F 7/40 |
|---|---|---|---|
| 2012/0135351 A1 | 5/2012 | Ichikawa et al. | |
| 2014/0295347 A1 * | 10/2014 | Aqad | G03F 7/0045 430/270.1 |
| 2015/0064620 A1 * | 3/2015 | Kaur | G03F 7/0046 430/270.1 |

FOREIGN PATENT DOCUMENTS

JP 2012193160 10/2012

* cited by examiner

*Primary Examiner* — John S Chu
(74) *Attorney, Agent, or Firm* — Birch, Stewart, Kolasch & Birch, LLP

(57) ABSTRACT

A salt represented by the formula (I).

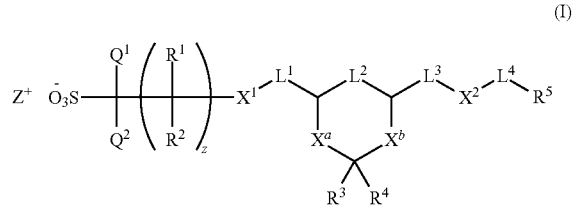

wherein $Z^+$, $Q^1$, $Q^2$, $R^1$, $R^2$, $R^3$, $R^4$, $R^5$, Z, $X^1$, $X^2$, $X^a$, $X^b$, $L^1$, $L^2$, $L^3$ and $L^4$ are defined in the specification.

7 Claims, No Drawings

SALT AND PHOTORESIST COMPOSITION CONTAINING THE SAME

This nonprovisional application claims priority under 35 U.S.C. § 119(a) on Patent Application No. 2017-043568 filed in JAPAN on Mar. 8, 2017, the entire contents of which are hereby incorporated by reference.

FIELD OF THE INVENTION

The present invention relates to a salt for photoresist compositions, and acid generator comprising the same, a photoresist composition and a method for producing a photoresist pattern.

BACKGROUND OF THE INVENTION

US2012/135351A1 mentions the following salt and a photoresist composition comprising the same as an acid generator.

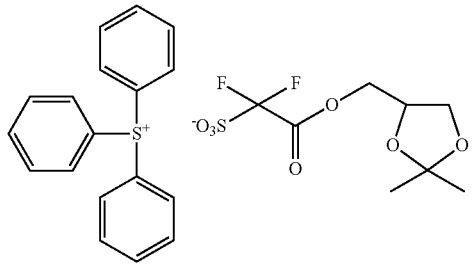

SUMMARY OF THE INVENTION

The present invention relates to the followings:
<1> A salt represented by the formula (I):

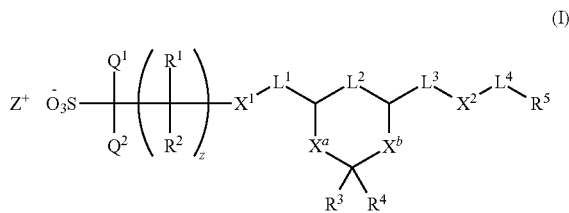

wherein $Q^1$ and $Q^2$ independently each represent a fluorine atom or a C1-C6 perfluoroalkyl group,
$R^1$ and $R^2$ independently each represent a hydrogen atom, a fluorine atom or a C1-C6 perfluoroalkyl group,
z represents an integer of 0 to 6,
$X^1$ and $X^2$ independently each represent *—CO—O—, *—O—CO—, —O—CO—O— or —O—, where * represents a binding potion to —C($R^1$)($R^2$)—, —C($Q^1$)($Q^2$)- or $L^4$.
L represents a C1-C28 divalent saturated hydrocarbon group in which a methylene group can be replaced by —O—, —S—, —CO— or —S(O)$_2$— and in which a hydrogen atom can be replaced by a fluorine atom or a hydroxyl group,
$L^2$, $L^3$ and $L^4$ independently each represent a single bond or a C1-C6 alkanediyl group, $X^a$ and $X^b$ independently each represent an oxygen atom or a sulfur atom,
$R^3$ and $R^4$ independently each represent a C1-C6 alkyl group, or jointly represent a C5-C12 alicyclic hydrocarbon ring together with a carbon atom bonded to $R^3$ and $R^4$,
$R^5$ represents a hydrogen atom, a hydroxyl group, a halogen atom or a C3-C24 cyclic hydrocarbon group in which a hydrogen atom can be replaced by a substituent and in which a methylene group can be replaced by —O—, —S—, —CO— or —S(O)$_2$—, and
$Z^+$ represents an organic cation.
<2> The salt according to <1>
wherein $X^1$ represents *—CO—O— or *—O—CO— where * represents a binding potion to —C($R^1$)($R^2$)— or —C($Q^1$)($Q^2$)-.
<3> The salt according to <1> or <2>
wherein $L^1$ represents a C1-C24 alkanediyl group in which a methylene group can be replaced by —O— or —CO—, or a group consisting of a divalent alicyclic hydrocarbon group and an alkanediyl group in which a methylene group can be replaced by —O— or —CO—.
<4> An acid generator comprising the salt according to any one of <1> to <3>.
<5> A photoresist composition comprising the acid generator according to <4> and a resin which comprises a structural unit having an acid-labile group.
<6> The photoresist composition according to <5> which further comprises a salt generating an acid weaker in acidity than an acid generated from the acid generator.
<7> A process for producing a photoresist pattern comprising the following steps (1) to (5):
  (1) a step of applying the photoresist composition according to <5> or <6> on a substrate,
  (2) a step of forming a photoresist film by conducting drying,
  (3) a step of exposing the photoresist film to radiation,
  (4) a step of baking the exposed photoresist film, and
  (5) a step of developing the baked photoresist film with an alkaline developer, thereby forming a photoresist pattern.

DESCRIPTION OF EMBODIMENTS

The salt of the disclosure is represented by the formula (I):

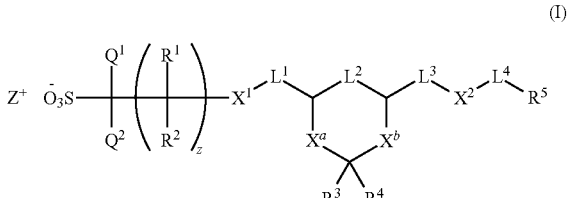

wherein $Q^1$ and $Q^2$ independently each represent a fluorine atom or a C1-C6 perfluoroalkyl group,
$R^1$ and $R^2$ independently each represent a hydrogen atom, a fluorine atom or a C1-C6 perfluoroalkyl group,
z represents an integer of 0 to 6,
$X^1$ and $X^2$ independently each represent *—CO—O—, *—O—CO—, —O—CO—O— or —O—, where * represents a binding potion to —C($R^1$)($R^2$)—, —C($Q^1$) ($Q^2$)- or $L^4$,
$L^1$ represents a C1-C28 divalent saturated hydrocarbon group in which a methylene group can be replaced by —O—, —S—, —CO— or —S(O)$_2$— and in which a hydrogen atom can be replaced by a fluorine atom or a hydroxyl group, $L^2$, $L^3$ and $L^4$ independently each represent a single bond or a C1-C6 alkanediyl group, $X^a$ and $X^b$ independently each represent an oxygen atom or a sulfur atom, $R^3$ and $R^4$ independently each represent a C1-C6 alkyl group, or represent a C5-C12 alicyclic hydrocarbon group together with a carbon atom bonded to $R^3$ and $R^4$, $R^5$ represents a hydrogen atom, a hydroxyl group, a halogen atom or a C3-C24 cyclic hydrocarbon group in which a methylene group can be replaced by —O—, —S—, —CO— or —S(O)$_2$—, and $Z^+$ represents an organic cation.

Hereinafter, the salt will be simply referred to as "salt (I)". In the salt (I), a structure having a negative charge represents "anion (I)", and a structure having a positive charge represents "cation (I)".

For $Q^1$, $Q^2$, $R^1$ and $R^2$, examples of a perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferred.

$Q^1$ and $Q^2$ each independently preferably represent a fluorine atom or a trifluoromethyl group, and $Q^1$ and $Q^2$ are more preferably fluorine atoms.

$R^1$ and $R^2$ each independently preferably represent a hydrogen atom or a fluorine atom.

z preferably represent 0.

$X^a$ and $X^b$ are preferably the same, and are more preferably —O—.

$X^1$ represents preferably *—CO—O— or *—O—CO— where * represents a binding potion to —C($R^1$)($R^2$)— or —C($Q^1$) ($Q^2$)-, more preferably *—CO—O— where * represents a binding potion to —C($R^1$)($R^2$)— or —C($Q^1$) ($Q^2$)-.

$X^2$ represents preferably *—O—CO— where * represents a binding potion to $L^4$.

For $L^1$, examples of the divalent saturated hydrocarbon group include linear alkylene groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and heptadecane-1,17-diyl group; branched alkylene groups such as an ethane-1,1-diyl group, a propane-1,1-diyl group, a propane-1,2-diyl group, a propane-2,2-diyl group, a pentane-2,4-diyl group, a 2-methylpropane-1,3-diyl group, 2-methylpropane-1,2-diyl group, pentane-1,4-diyl group, and 2-methylbutane-1,4-diyl group;

divalent monocyclic alicyclic hydrocarbon groups such as cyclobutane-1,3-diyl group, cyclopentane-1,3-diyl group, cyclohexane-1,4-diyl group and cyclooctane-1,5-diyl group; and divalent polycyclic alicyclic hydrocarbon groups such as norbornane-1,4-diyl group, norbornane-2,5-diyl group, adamantane-1,5-diyl group and adamantane-2,6-diyl group.

$L^1$ represents preferably a C1-C24 alkanediyl group in which a methylene group can be replaced by —O— or —CO—, or a group consisting of a C3-C18 divalent alicyclic hydrocarbon group and a C1-C6 alkanediyl group in which a methylene group can be replaced by —O— or —CO—, more preferably a C1-C6 alkanediyl group in which a methylene group can be replaced by —O— or —CO—, or a group consisting of a C3-C12 divalent alicyclic hydrocarbon group and a C1-C6 alkanediyl group in which a methylene group can be replaced by —O— or —CO—.

Preferred examples of L represents —(C3-C12 divalent alicyclic hydrocarbon)-(a C1-C6 alkanediyl group in which a methylene group can be replaced by —O— or —CO—)-, -(a C1-C6 alkanediyl group in which a methylene group can be replaced by —O— or —CO—)-(C3-C12 divalent alicyclic hydrocarbon)-, -(a C1-C6 alkanediyl group in which a methylene group can be replaced by —O— or —CO—)-(C3-C12 divalent alicyclic hydrocarbon)-(a C1-C6 alkanediyl group in which a methylene group can be replaced by —O— or —CO—)-.

For $L^2$, $L^3$ and $L^4$, examples of the alkanediyl group include a linear alkylene groups such as a methylene group, an ethylene group, a propane-1,3-diyl group, a butane-1,4-diyl group, a pentane-1,5-diyl group, a hexane-1,6-diyl group; and branched alkylene groups such as an ethane-1,1-diyl group, a propane-1,1-diyl group, a propane-1,2-diyl group, a propane-2,2-diyl group, a pentane-2,4-diyl group, a 2-methylpropane-1,3-diyl group, 2-methylpropane-1,2-diyl group, pentane-1,4-diyl group, and 2-methylbutane-1,4-diyl group.

$L^2$ is preferably a single bond or a methylene group, more preferably a methylene group.

$L^3$ is preferably a methylene group or an ethylene group, more preferably a methylene group.

$L^4$ is preferably a single bond or a C1 to C4 alkanediyl group, more preferably a single bond, a propanediyl group or a butanediyl group.

Preferably $X^a$ and $X^b$ are an oxygen atom.

For $R^3$ and $R^4$, examples of the alkyl group include a methyl group, an ethyl group, a propyl group, a butyl group, a pentyl group and a hexyl group.

For $R^3$ and $R^4$, examples the C5-C12 alicyclic hydrocarbon ring represented by them together with a carbon atom include a cycloheptane ring, a cyclohexane ring and an adamantane ring.

$R^3$ and $R^4$ are preferably each a methyl group, or a cyclohexane ring or adamantane ring together with a carbon atom bonded to them.

The cyclic hydrocarbon group represented by $R^5$ includes an alicyclic hydrocarbon group and an aromatic hydrocarbon group.

The cyclic hydrocarbon group may be a monocyclic one or polycyclic one such as a spiro ring, and be saturated hydrocarbon group or unsaturated hydrocarbon group.

Examples of the alicylic hydrocarbon group include a monocyclic alicylic hydrocarbon group such as a cyclopropyl group, a cyclobutyl group, a cyclopentyl group, a cyclohexyl group, a methylcyclohexyl group, a dimethylcyclohexyl group, a cycloheptyl group, a cyclooctyl group, a cycloheptyl group and a cyclodecyl group, and a polycyclic calicylic hydrocarbon groups such as an adamantyl group and a norbornyl group.

The alicylic hydrocarbon group has preferably 3 to 18 carbon atoms, more preferably 3 to 12 carbon atoms.

Examples of the aromatic hydrocarbon group include an aryl group such as a phenyl group, a 1-naphthyl group, a 2-naphthyl group, a biphenylyl group, an anthryl group, a phenanthryl group and binaphthyl group.

The aromatic hydrocarbon group has 3 to 14 carbon atoms, more preferably 6 to 10 carbon atoms.

The cyclic hydrocarbon group has preferably 6 to 24 carbon atoms in total, and may have a substituent.

Examples of the substituent include a hydroxy group, a group having a hydroxy group, a halogen atom, a cyano group, a C1-C12 alkyl group, a C1-C12 alkoxy group, a C2-C13 alkoxycarbonyl group, a C2-C13 alkylcarbonyloxy group, a C3-C12 alicyclic hydrocarbon group and a C6-C10 aromatic hydrocarbon group.

Examples of the C1-C12 alkyl group include a methyl group, an ethyl group, a propyl group, a butyl group, a pentyl group, a hexyl group, a heptyl group, an octyl group, a nonyl group, a decyl group, an undecyl group and dodecyl group.

Examples of the C1-C12 alkoxy group include a methoxy group, an ethoxy group, a propoxy group, a butoxy group, a pentyloxy group, a hexyloxy group, an octyloxy group, a 2-ethyl hexyloxy group, a nonyloxy group, a decyloxy group, an undecyloxy group and a dodecyloxy group.

Examples of the C2-C13 alkoxycarbonyl group include a methoxycarbonyl group, an ethoxycarbonyl group, a propoxycarbonyl group, a butoxycarbonyl group, a pentyloxycarbonyl group, a hexyloxycarbonyl group, an octyloxycarbonyl group, a 2-ethylhexyloxycarbonyl group, a nonyloxycarbonyl group, a decyloxycarbonyl group, an undecyloxycarbonyl group and dodecyloxycarbonyl group.

Examples of the C2-C13 alkylcarbonyl group include an acetyl group, a propionyl group and a butyryl group. Examples of the C2-C13 alkylcarbonyloxy group include an acetyloxy group, a propionyloxy group and a butyryloxy group.

Examples of the C3-C12 alicyclic hydrocarbon group include the following ones.

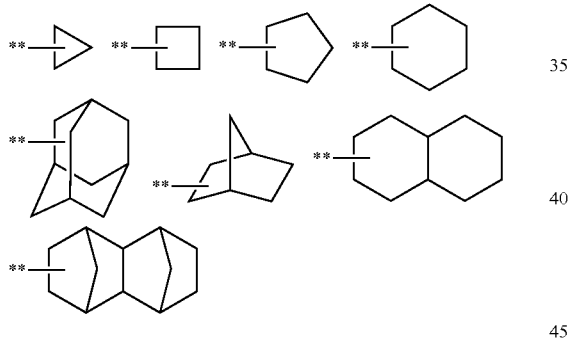

In the above, ** represents a binding position.

Examples of the C6-C10 aromatic hydrocarbon group include a phenyl group, a naphthyl group, a tolyl group, a xylyl group, and a cyclohexylphenyl group.

Examples of any combination of those groups include combinations of a hydroxy group and the C1-C12 alkyl group, and combinations of the C1-C12 alkyl group and the C6-C10 aromatic hydrocarbon group.

Examples of the combinations of a hydroxy group and the C1-C12 alkyl group include a C1-C12 hydroxyalkyl group such as a hydroxymethyl group and a hydroxyethyl group.

Examples of the combinations of the C1-C12 alkyl group and the C6-C10 aromatic hydrocarbon group include a C7-C2 aralkyl group such as a benzyl group.

Examples of the alicyclic hydrocarbon group represented by Y include preferably those represented by the formulae (Y1) to (Y40), more preferably those represented by the formulae (Y1) to (Y20), (Y30), (Y31), (Y39) and (Y40), still more preferably those represented by the formulae (Y11), (Y15), (Y30), (Y39) and (Y40).

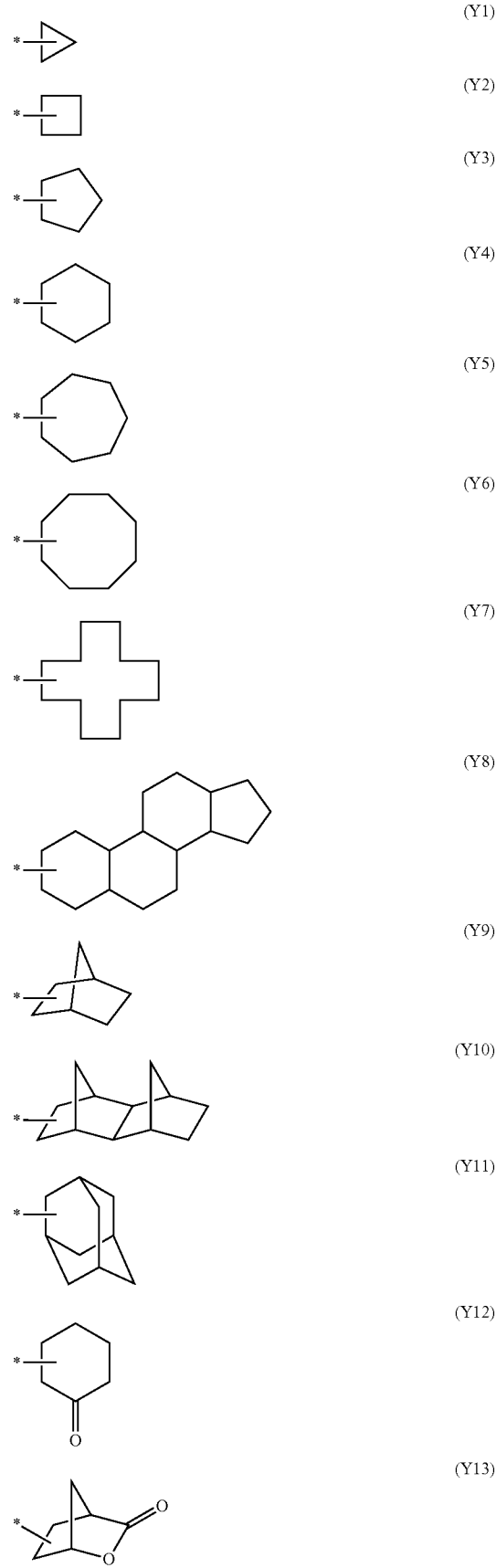

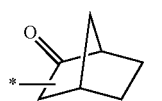 (Y3)
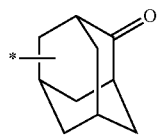 (Y4)
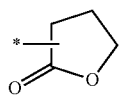 (Y5)
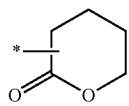 (Y6)
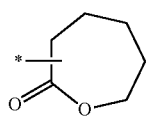 (Y7)
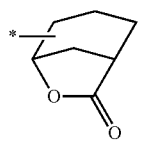 (Y8)
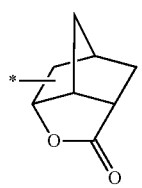 (Y9)
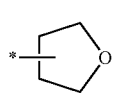 (Y10)
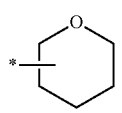 (Y11)
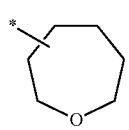 (Y12)
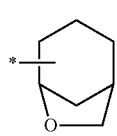 (Y13)
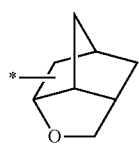 (Y14)
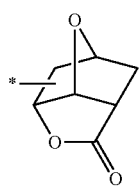 (Y15)
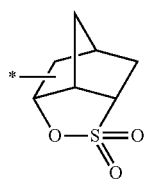 (Y16)
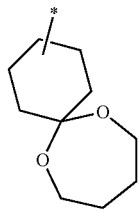 (Y17)
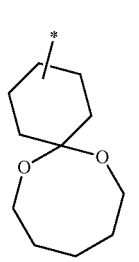 (Y18)
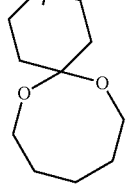 (Y19)
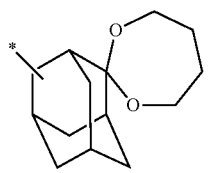 (Y20)
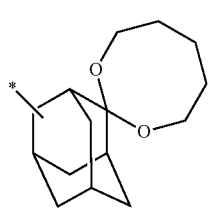 (Y21)
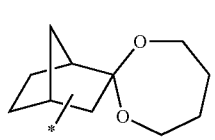 (Y22)
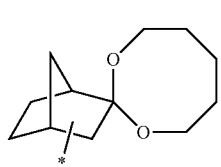 (Y23)

-continued (Y34)
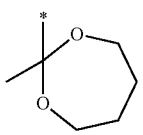

(Y35)
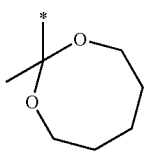

(Y36)
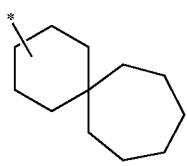

(Y37)
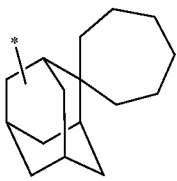

(Y38)
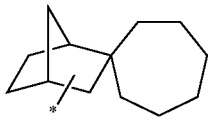

(Y39)
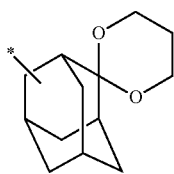

-continued (Y40)
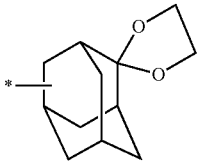

Substituents which $R^5$ has is preferably an alkyl group, a hydroxyl group, a group which has a hydroxyl group, such as a hydroxyalkyl group, and a halogen atom, and more preferably an alkyl group, a hydroxyl group and a fluorine atom.

$R^5$ is preferably an alkyl group or a C3-C18 alicyclic hydrocarbon group in which a hydrogen atom can be replaced by a substituent and in which a methylene group can be replaced by —O—, —S—, —CO— or —S(O)$_2$—, more preferably a t-butyl group, an adamantyl group in which a hydrogen atom can be replaced by a substituent and in which a methylene group can be replaced by —O—, —S—, —CO— or —S(O)$_2$—, or a cyclohexyl group in which a hydrogen atom can be replaced by a substituent and in which a methylene group can be replaced by —O—, —S—, —CO— or —S(O)$_2$—, and still more preferably a t-butyl group, an adamantyl group, an adamantyl group in which a hydrogen atom can be replaced by an alkyl group, a cyclohexyl group, a hydroxyadamantyl group, an oxoadamantyl group, and the following group, and further more preferably a t-butyl group or an adamantyl group in which a hydrogen atom can be replaced by an alkyl group.

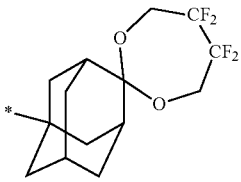 [SMILES: *C12CC3CC(C1)C1(OCC(F)(F)C(F)(F)CO1)C(C3)C2]

Specific examples of the anion (I) include the following ones. Among them, preferred are those represented by formulae (Ia-1) to (Ia-28).

(Ia-1)
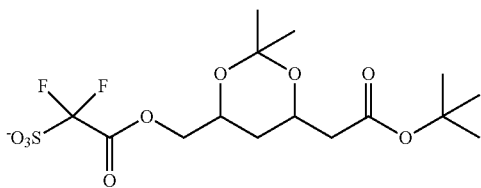

(Ia-2)
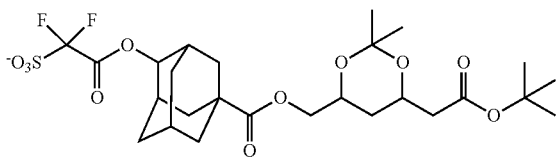

(Ia-3)
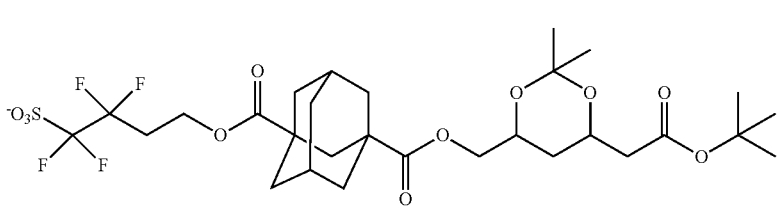

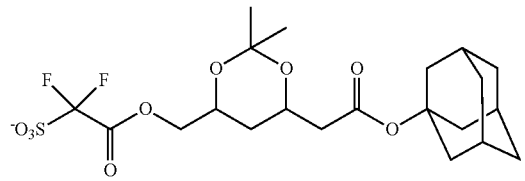
(Ia-4)
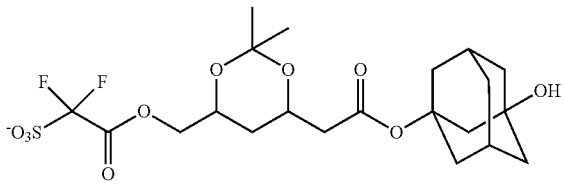
(Ia-5)
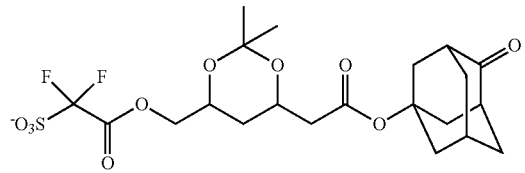
(Ia-6)
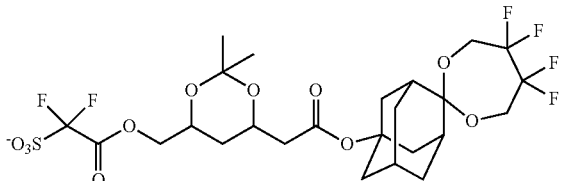
(Ia-7)
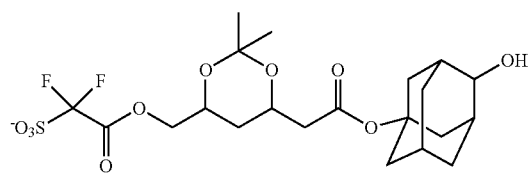
(Ia-8)
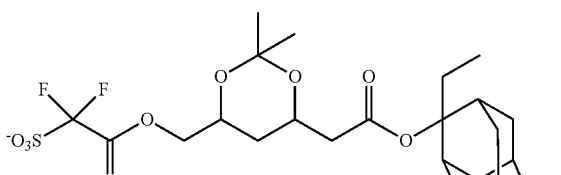
(Ia-9)
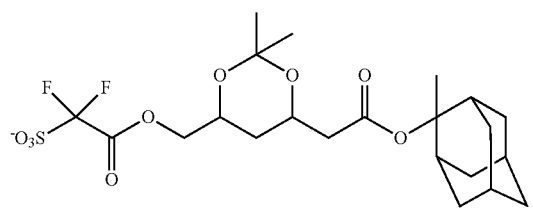
(Ia-10)
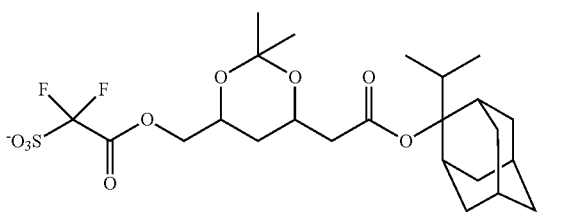
(Ia-11)
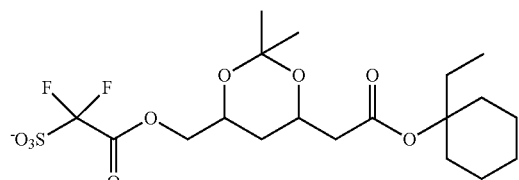
(Ia-12)
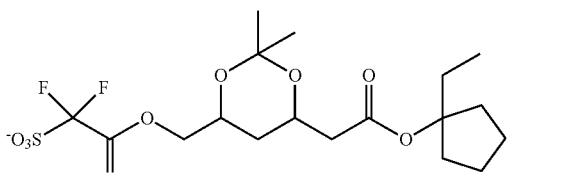
(Ia-13)
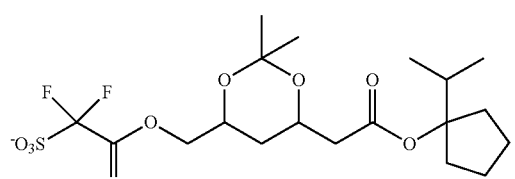
(Ia-14)
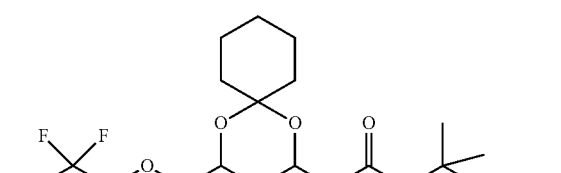
(Ia-15)
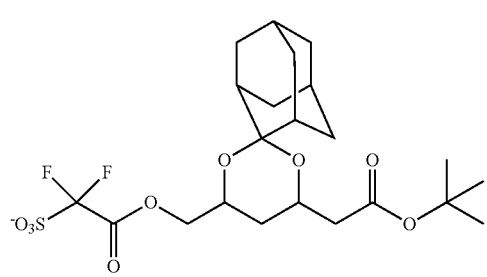
(Ia-16)

(Ia-17)
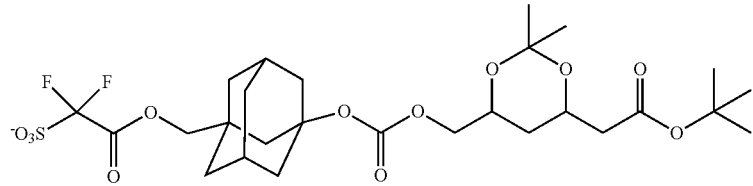
(Ia-18)
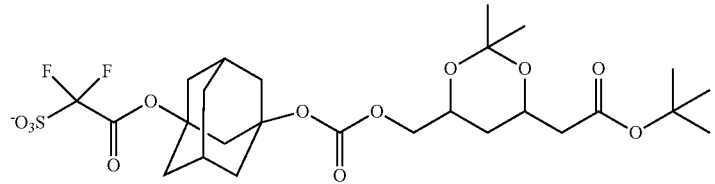
(Ia-19)
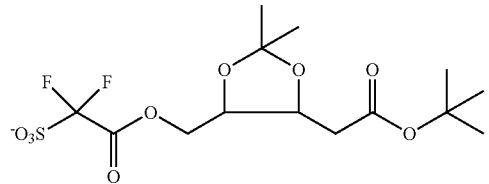
(Ia-20)
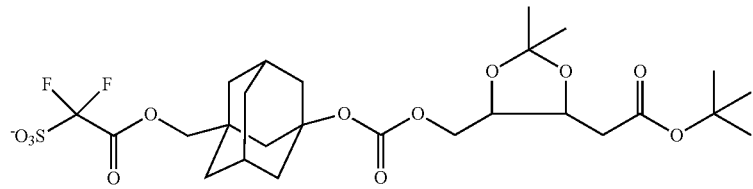
(Ia-21)
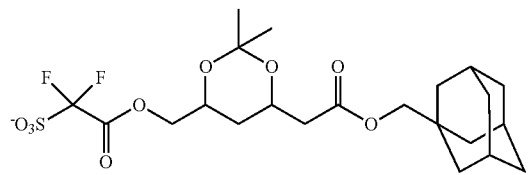
(Ia-22)
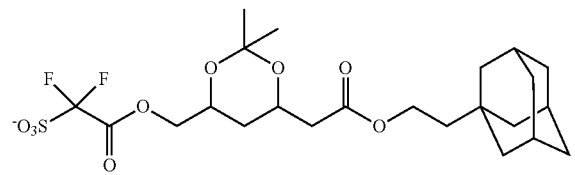
(Ia-23)
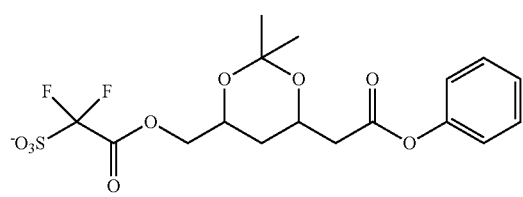
(Ia-24)
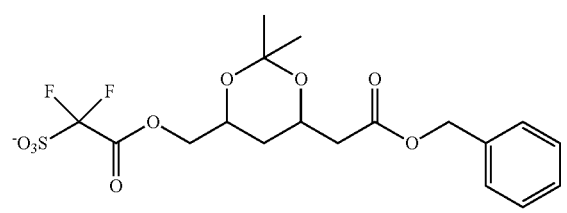
(Ia-25)
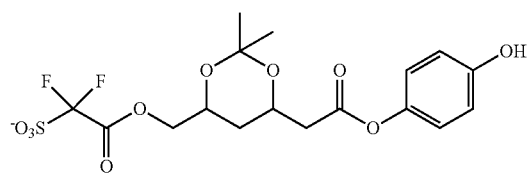
(Ia-26)
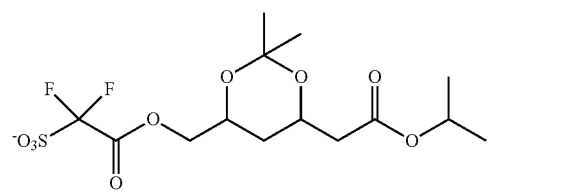

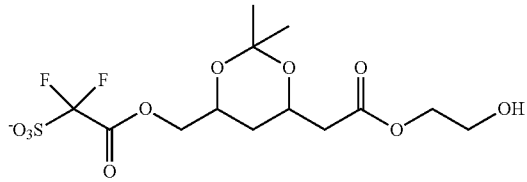
(Ia-27)

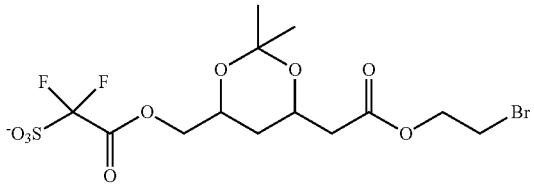
(Ia-28)

Examples of the organic cation represented by $Z^+$ include an organic onium cation such as an organic sulfonium cation, an organic iodonium cation, an organic ammonium cation, a benzothiazolium cation and an organic phosphonium cation.

Among them, an organic sulfonium cation and an organic iodonium cation are preferred, and a sulfonium cation, specifically arylsulfonium cation, is more preferred.

Preferred examples of the cation include those represented by the formulae (b2-1), (b2-2), (b2-3) and (b2-4):

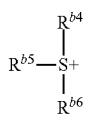
(b2-1)

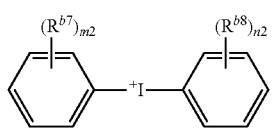
(b2-2)

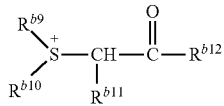
(b2-3)

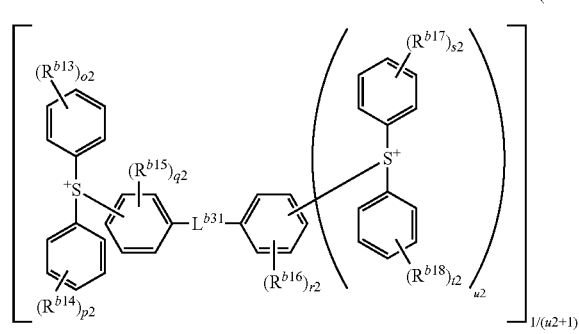
(b2-4)

In the formulae (b2-1) to (b2-4), $R^{b4}$, $R^{b5}$ and $R^{b6}$ independently represent a C1-C30 aliphatic hydrocarbon group, a C3-C36 alicyclic hydrocarbon group and a C6-C36 aromatic hydrocarbon group. The aliphatic hydrocarbon group can have a substituent selected from the group consisting of a hydroxy group, a C1-C12 alkoxy group, a C3-C12 alicyclic hydrocarbon group and a C6-C18 aromatic hydrocarbon group. The alicyclic hydrocarbon group can have a substituent selected from the group consisting of a halogen atom, a C1-C18 aliphatic hydrocarbon group, a C2-C4 acyl group and a glycidyloxy group. The aromatic hydrocarbon group can have a substituent selected from the group consisting of a halogen atom, a hydroxy group, a C1-C18 aliphatic hydrocarbon group and a C1-C12 alkoxy group.

$R^{b4}$ and $R^{b5}$ can be bonded to form a ring together with the adjacent $S^+$, and a methylene group in the ring may be replaced by —CO—, —O— or —SO—.

$R^{b7}$ and $R^{b8}$ are independently in each occurrence a hydroxy group, a C1-C12 aliphatic hydrocarbon group or a C1-C12 alkoxy group, m2 and n2 independently represents an integer of 0 to 5.

$R^{b9}$ and $R^{b10}$ independently represent a C1-C36 aliphatic hydrocarbon group or a C3-C36 alicyclic hydrocarbon group.

$R^{b9}$ and $R^{b10}$ can be bonded to form a ring together with the adjacent S+, and a methylene group in the divalent acyclic hydrocarbon group may be replaced by —CO—, —O— or —SO—.

$R^{b11}$ represents a hydrogen atom, a C1-C36 aliphatic hydrocarbon group, a C3-C36 alicyclic hydrocarbon group or a C6-C18 aromatic hydrocarbon group.

$R^{b12}$ represents a C1-C12 aliphatic hydrocarbon group in which a hydrogen atom can be replaced by a C6-C18 aromatic hydrocarbon group, a C3-C18 saturated cyclic hydrocarbon group and a C6-C18 aromatic hydrocarbon group in which a hydrogen atom can be replaced by a C1-C12 alkoxy group or a (C1-C12 alkyl)carbonyloxy group.

$R^{b11}$ and $R^{b12}$ can be bonded each other to form a C1-C10 divalent acyclic hydrocarbon group which forms a 2-oxo-cycloalkyl group together with the adjacent —CHCO—, and a methylene group in the divalent acyclic hydrocarbon group may be replaced by —CO—, —O— or —SO—.

$R^{b13}$, $R^{b14}$, $R^{b15}$, $R^{b16}$, $R^{b17}$ and $R^{b18}$ independently represent a hydroxy group, a C1-C12 aliphatic hydrocarbon group or a C1-C12 alkoxy group.

$L^{b31}$ represents —S— or —O— and o2, p2, s2 and t2 each independently represents an integer of 0 to 5, q2 and r2 each independently represents an integer of 0 to 4, and u2 represents 0 or 1.

Preferred examples of the aliphatic hydrocarbon group represented by $R^{b4}$ to $R^{b12}$ include an alkyl group such as a methyl group, an ethyl group, a n-propyl group, an isopropyl group, a n-butyl group, sec-butyl group, a tert-butyl group, a pentyl group, a hexyl group, an octyl group and 2-ethylhexyl group. The aliphatic hydrocarbon group represented by $R^{b9}$, $R^{b10}$, $R^{b11}$ and $R^{b12}$ has preferably 1 to 12 carbon atoms.

The alicyclic hydrocarbon group may be monocyclic or polycyclic one. Preferred examples of the monocyclic hydrocarbon group include a cycloalkyl group such as a cyclopentyl group, a cyclohexyl group, a methylcyclohexyl group, a dimethylcyclohexyl group, a cycloheptyl group and a cyclooctyl group. Preferred examples of the polycyclic hydrocarbon group include an adamantyl group, a norbornyl group and a decahydronaphtyl group, and the following groups.

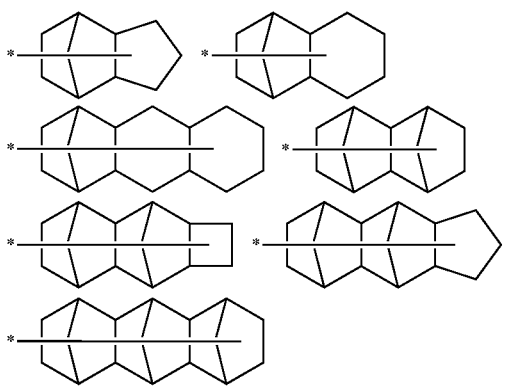

The alicyclic hydrocarbon group represented by $R^{b9}$, $R^{b10}$, $R^{b11}$ and $R^{b12}$ has preferably 3 to 18 carbon atoms, more preferably 4 to 12 carbon atoms.

Examples of the alicyclic hydrocarbon group in which a hydrogen atom has been replaced by an aliphatic hydrocarbon group include a methylcyclohexyl group, a dimethylcyclohexyl group, a methylnorbornyl group, and an isonorbornyl group.

The alicyclic hydrocarbon group in which a hydrogen atom has been replaced by an aliphatic hydrocarbon group has preferably 20 or less carbon atoms in total.

Examples of the aromatic hydrocarbon group include an aryl group such as a phenyl group, tolyl group, xylyl group, cumenyl group, mesityl group, p-ethylphenyl group, p-tert-butylphenyl group, p-adamantylphenyl group, a biphenylyl group, a naphthyl group, a phenanthryl group, a 2,6-diethylphenyl group, a 2-methyl-6-ethylphenyl group.

When the aromatic hydrocarbon group has an alicyclic hydrocarbon group or an aliphatic hydrocarbon group, it is preferred that the alicyclic hydrocarbon group and the aliphatic hydrocarbon group have respectively 1 to 18 carbon atoms and 3 to 18 carbon atoms.

Examples of the aromatic hydrocarbon group in which a hydrogen atom has been replaced by an alkoxy group include p-methoxyphenyl group.

Examples of the aliphatic hydrocarbon group in which a hydrogen atom has been replaced by an aromatic hydrocarbon group include a benzyl group, a phenethyl group, a phenylpropyl group, trityl group, naphthylmethyl group, and a naphthylethyl group.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the acyl group include an acetyl group, a propyonyl group and a butyryl group.

Examples of the halogen atom include a fluorine atom, a chlorine atom, a bromine atom and an iodine atom.

Examples of alkylcarbonyloxy group include a methylcarbonyloxy group, an ethylcarbonyloxy group, a n-propylcarbonyloxy group, an isopropylcarbonyloxy group, a n-butylcarbonyloxy group, a sec-butylcarbonyloxy group, a tert-butylcarbonyloxy group, a pentylcarbonyloxy group, a hexylcarbonyloxy group, an octylcarbonyloxy group and a 2-ethyl hexylcarbonyloxy group.

The ring group formed by bonding $R^{b4}$ and $R^{b5}$ together with the adjacent $S^+$ may be monocyclic or polycyclic, saturated or unsaturated, aromatic or nonaromatic group. The ring is generally 3 to 12-membered one, preferably 3 to 7-membered one. Examples of the ring include the following ones.

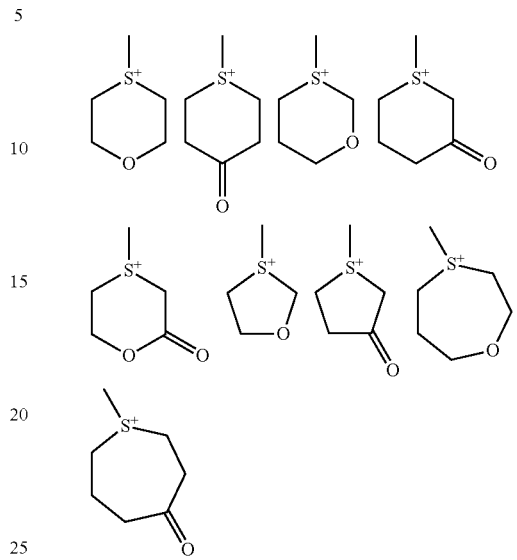

The ring group formed by bonding $R^{b9}$ and $R^{b10}$ together with the adjacent $S^+$ may be monocyclic or polycyclic, saturated or unsaturated, aromatic or nonaromatic group. The ring has generally C3-C12, preferably C3-C7 carbon atoms. Examples of the ring include a thiolan-1-ium ring (tetrahydrothiphenium ring), a thian-1-ium ring and a 1,4-oxathian-4-ium ring.

The ring group formed by bonding $R^{b11}$ and $R^{b12}$ together with —CH—CO— may be monocyclic or polycyclic, saturated or unsaturated, aromatic or nonaromatic group. The ring has generally C3-C12, preferably C3-C7 carbon atoms. Examples of the ring include an oxocycloheptane ring, an oxocyclohexane ring, an oxonorbornane ring, and an oxoadamantane ring.

Preferred examples of the cation for the acid generator include an arylsulfonium cation, specifically cation of formula (b2-1), and more specifically a phenylsulfonium cation.

Preferably, the cation of formula (b2-1) has one or three phenyl groups. When the cation of formula (b2-1) has one phenyl group, it has further a thiolan-1-ium ring or a 1,4-oxathian-4-ium ring.

Examples of the cation represented by the formula (b2-1) include the followings.

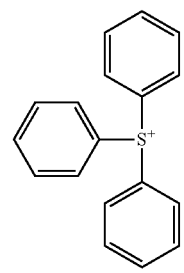

(b2-c-1)

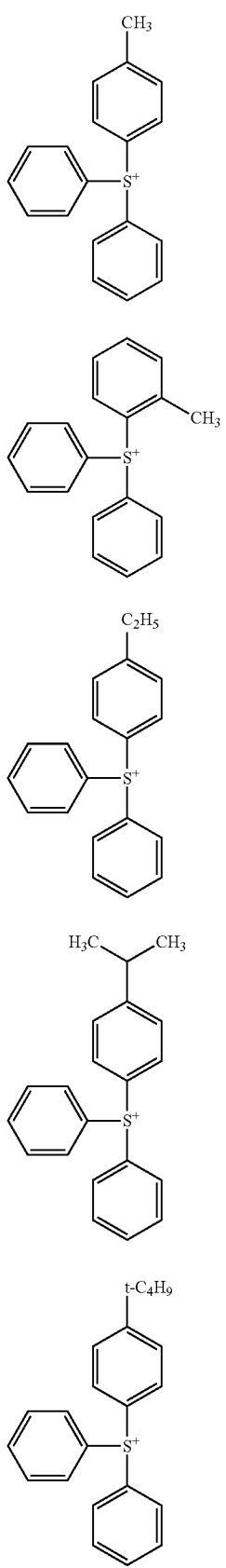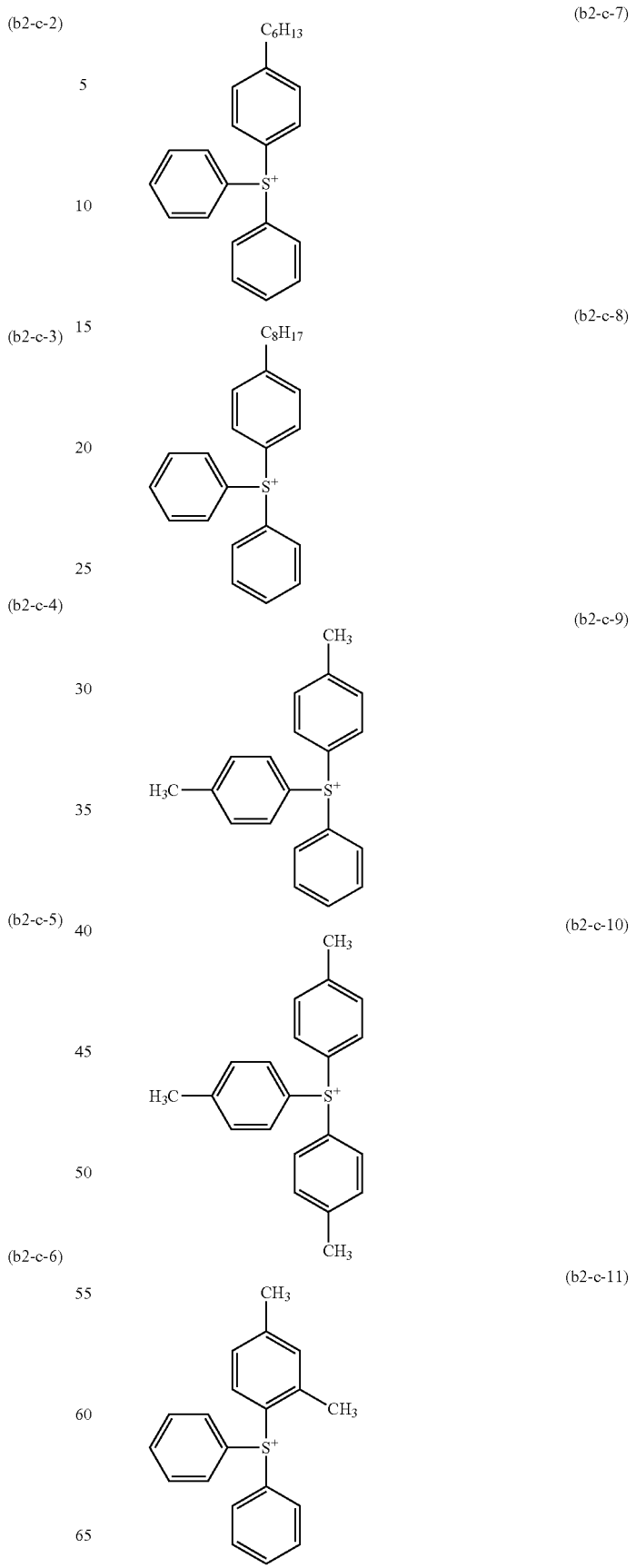

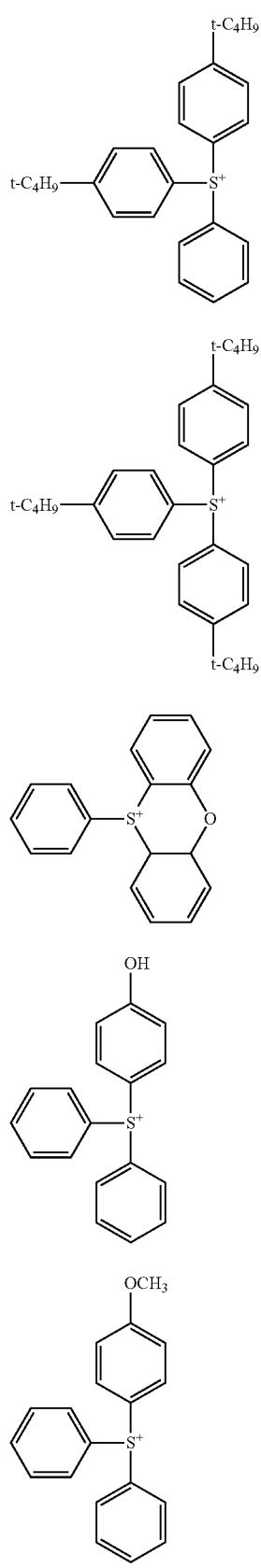
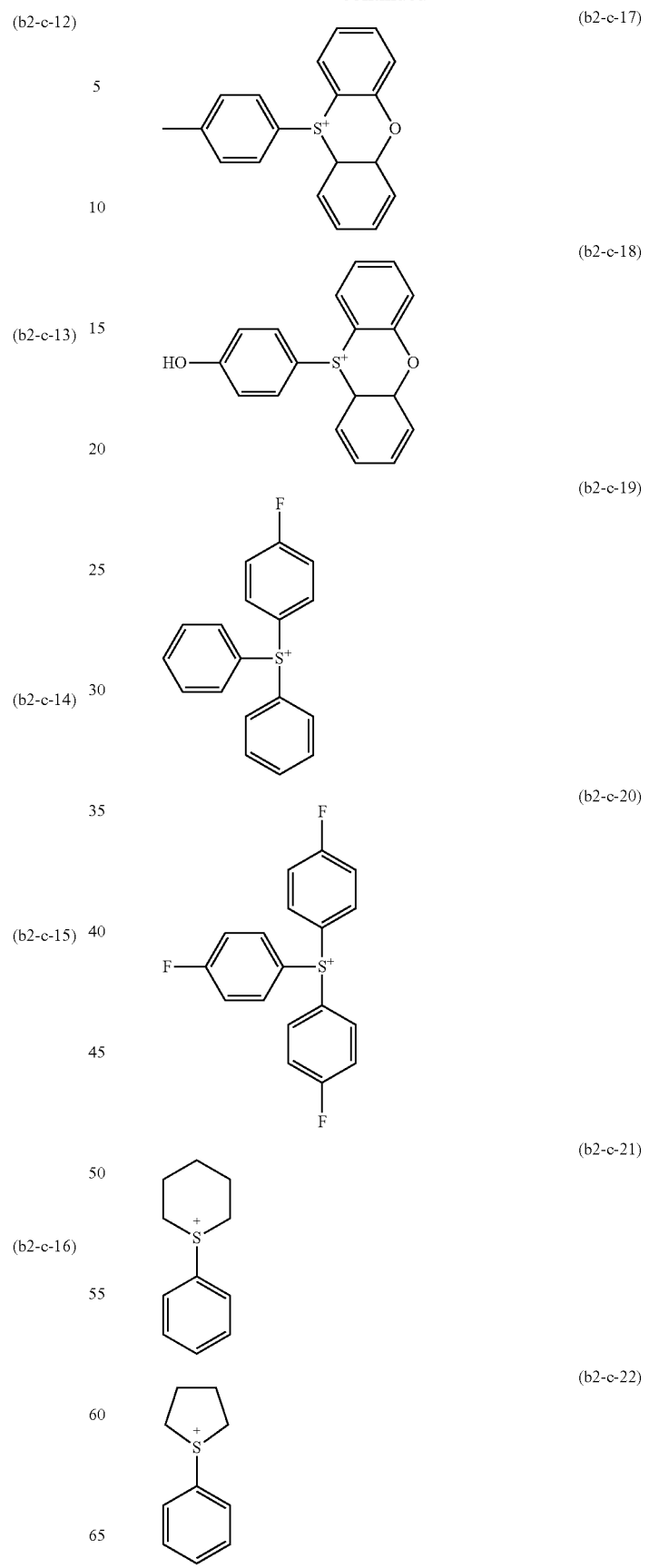

(b2-c-23)
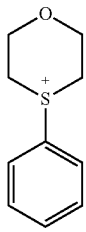
(b2-c-24)
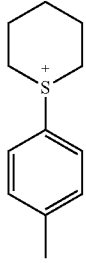
(b2-c-25)
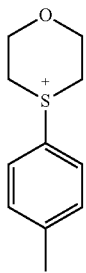
(b2-c-26)
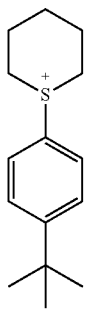
(b2-c-27)
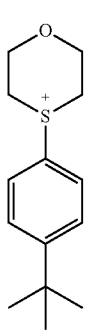
Examples of the cation represented by the formula (b2-2) include the followings.
(b2-c-28)
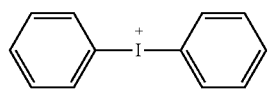
(b2-c-29)
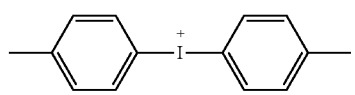
(b2-c-30)
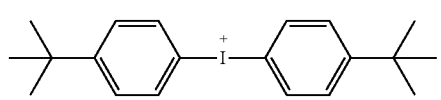
Examples of the cation represented by the formula (b2-3) include the followings.
(b2-c-31)
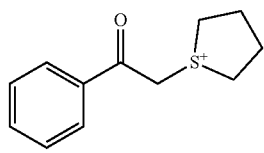
(b2-c-32)
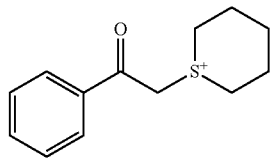
(b2-c-33)
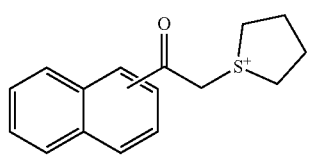
(b2-c-34)
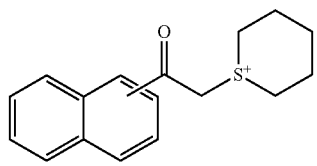
Examples of the cation represented by the formula (b2-4) include the followings.
(b2-c-35)
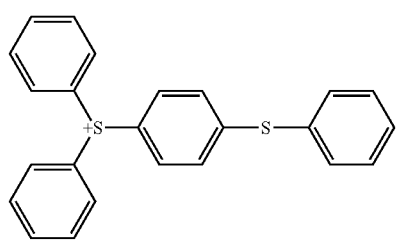

(b2-c-36)
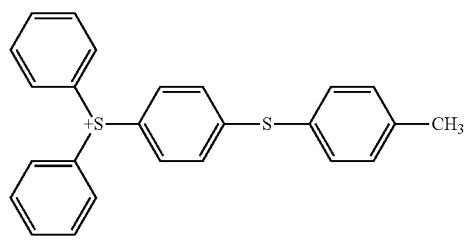
(b2-c-37)
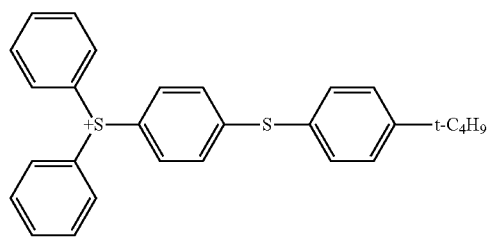
(b2-c-38)
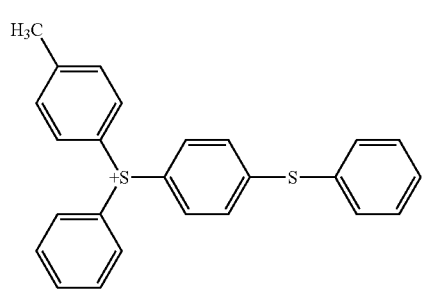
(b2-c-41)
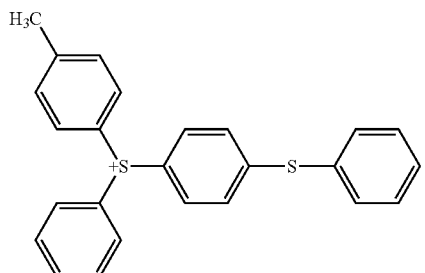
(b2-c-42)
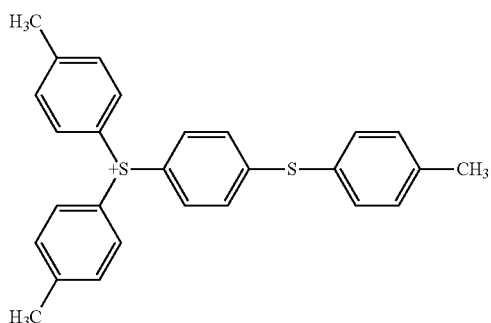
(b2-c-43)
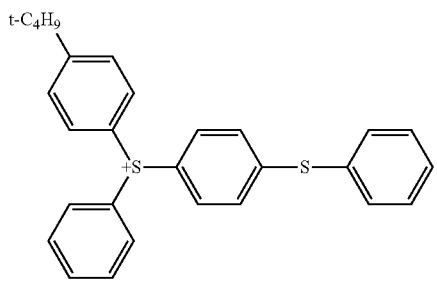
(b2-c-39)
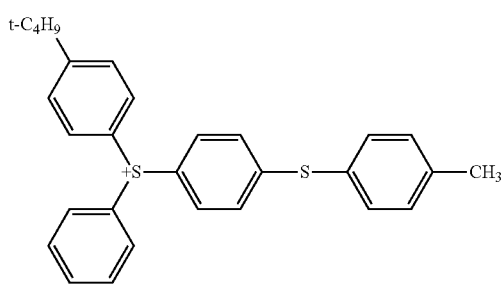
(b2-c-44)
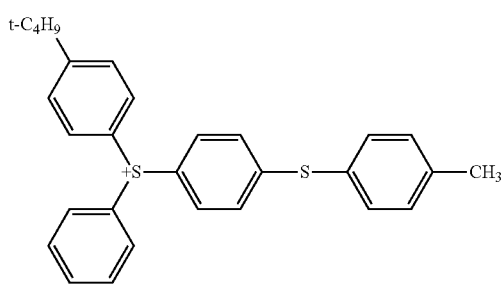
(b2-c-40)
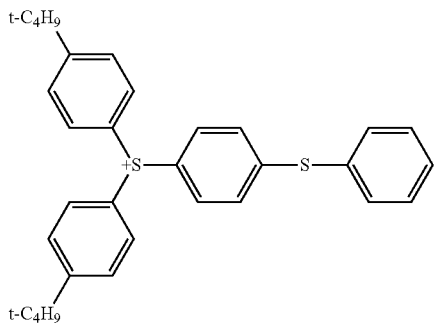
(b2-c-45)

-continued (b2-c-46)

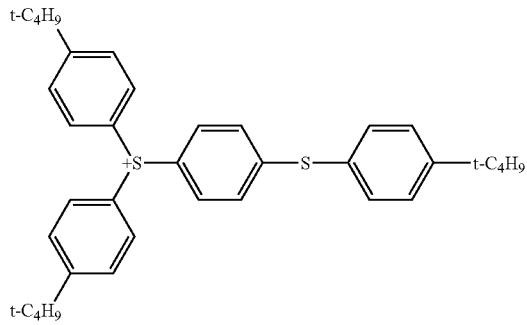

Specific examples of the salt (I) include those as listed in following Tables.

In those tables, every character in each column represents a sign which represents one of the chemical formulae specifically illustrated above. For example, the salt (I-1) consists of the anion of formula (Ia-1) and the cation of formula (b2-c-1) as shown below.

(I-1)

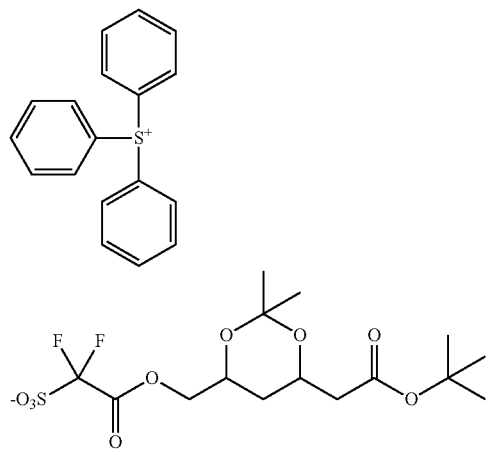

TABLE I

| Salt (I) | anion (I) | Cation (I) |
|---|---|---|
| (I-1) | (Ia-1) | (b2-c-1) |
| (I-2) | (Ia-2) | (b2-c-1) |
| (I-3) | (Ia-3) | (b2-c-1) |
| (I-4) | (Ia-4) | (b2-c-1) |
| (I-5) | (Ia-5) | (b2-c-1) |
| (I-6) | (Ia-6) | (b2-c-1) |
| (I-7) | (Ia-7) | (b2-c-1) |
| (I-8) | (Ia-8) | (b2-c-1) |
| (I-9) | (Ia-9) | (b2-c-1) |
| (I-10) | (Ia-10) | (b2-c-1) |
| (I-11) | (Ia-11) | (b2-c-1) |
| (I-12) | (Ia-12) | (b2-c-1) |
| (I-13) | (Ia-13) | (b2-c-1) |
| (I-14) | (Ia-14) | (b2-c-1) |
| (I-15) | (Ia-15) | (b2-c-1) |
| (I-16) | (Ia-16) | (b2-c-1) |
| (I-17) | (Ia-17) | (b2-c-1) |
| (I-18) | (Ia-18) | (b2-c-1) |
| (I-19) | (Ia-19) | (b2-c-1) |
| (I-20) | (Ia-20) | (b2-c-1) |
| (I-21) | (Ia-1) | (b2-c-10) |
| (I-22) | (Ia-2) | (b2-c-10) |

TABLE I-continued

| Salt (I) | anion (I) | Cation (I) |
|---|---|---|
| (I-23) | (Ia-3) | (b2-c-10) |
| (I-24) | (Ia-4) | (b2-c-10) |
| (I-25) | (Ia-5) | (b2-c-10) |
| (I-26) | (Ia-6) | (b2-c-10) |
| (I-27) | (Ia-7) | (b2-c-10) |
| (I-28) | (Ia-8) | (b2-c-10) |
| (I-29) | (Ia-9) | (b2-c-10) |
| (I-30) | (Ia-10) | (b2-c-10) |
| (I-31) | (Ia-11) | (b2-c-10) |
| (I-32) | (Ia-12) | (b2-c-10) |
| (I-33) | (Ia-13) | (b2-c-10) |
| (I-34) | (Ia-14) | (b2-c-10) |
| (I-35) | (Ia-15) | (b2-c-10) |
| (I-36) | (Ia-16) | (b2-c-10) |
| (I-37) | (Ia-17) | (b2-c-10) |
| (I-38) | (Ia-18) | (b2-c-10) |
| (I-39) | (Ia-19) | (b2-c-10) |
| (I-40) | (Ia-20) | (b2-c-10) |

TABLE 2

| Salt (I) | anion (I) | Cation (I) |
|---|---|---|
| (I-41) | (Ia-1) | (b2-c-12) |
| (I-42) | (Ia-2) | (b2-c-12) |
| (I-43) | (Ia-3) | (b2-c-12) |
| (I-44) | (Ia-4) | (b2-c-12) |
| (I-45) | (Ia-5) | (b2-c-12) |
| (I-46) | (Ia-6) | (b2-c-12) |
| (I-47) | (Ia-7) | (b2-c-12) |
| (I-48) | (Ia-8) | (b2-c-12) |
| (I-49) | (Ia-9) | (b2-c-12) |
| (I-50) | (Ia-10) | (b2-c-12) |
| (I-51) | (Ia-11) | (b2-c-12) |
| (I-52) | (Ia-12) | (b2-c-12) |
| (I-53) | (Ia-13) | (b2-c-12) |
| (I-54) | (Ia-14) | (b2-c-12) |
| (I-55) | (Ia-15) | (b2-c-12) |
| (I-56) | (Ia-16) | (b2-c-12) |
| (I-57) | (Ia-17) | (b2-c-12) |
| (I-58) | (Ia-18) | (b2-c-12) |
| (I-59) | (Ia-19) | (b2-c-12) |
| (I-60) | (Ia-20) | (b2-c-12) |
| (I-61) | (Ia-1) | (b2-c-14) |
| (I-62) | (Ia-2) | (b2-c-14) |
| (I-63) | (Ia-3) | (b2-c-14) |
| (I-64) | (Ia-4) | (b2-c-14) |
| (I-65) | (Ia-5) | (b2-c-14) |
| (I-66) | (Ia-6) | (b2-c-14) |
| (I-67) | (Ia-7) | (b2-c-14) |
| (I-68) | (Ia-8) | (b2-c-14) |
| (I-69) | (Ia-9) | (b2-c-14) |
| (I-70) | (Ia-10) | (b2-c-14) |
| (I-71) | (Ia-11) | (b2-c-14) |
| (I-72) | (Ia-12) | (b2-c-14) |
| (I-73) | (Ia-13) | (b2-c-14) |
| (I-74) | (Ia-14) | (b2-c-14) |
| (I-75) | (Ia-15) | (b2-c-14) |
| (I-76) | (Ia-16) | (b2-c-14) |
| (I-77) | (Ia-17) | (b2-c-14) |
| (I-78) | (Ia-18) | (b2-c-14) |
| (I-79) | (Ia-19) | (b2-c-14) |
| (I-80) | (Ia-20) | (b2-c-14) |

TABLE 3

| Salt (I) | anion (I) | Cation (I) |
|---|---|---|
| (I-81) | (Ia-1) | (b2-c-27) |
| (I-82) | (Ia-2) | (b2-c-27) |
| (I-83) | (Ia-3) | (b2-c-27) |
| (I-84) | (Ia-4) | (b2-c-27) |
| (I-85) | (Ia-5) | (b2-c-27) |
| (I-86) | (Ia-6) | (b2-c-27) |
| (I-87) | (Ia-7) | (b2-c-27) |
| (I-88) | (Ia-8) | (b2-c-27) |
| (I-89) | (Ia-9) | (b2-c-27) |
| (I-90) | (Ia-10) | (b2-c-27) |
| (I-91) | (Ia-11) | (b2-c-27) |
| (I-92) | (Ia-12) | (b2-c-27) |
| (I-93) | (Ia-13) | (b2-c-27) |
| (I-94) | (Ia-14) | (b2-c-27) |
| (I-95) | (Ia-15) | (b2-c-27) |
| (I-96) | (Ia-16) | (b2-c-27) |
| (I-97) | (Ia-17) | (b2-c-27) |
| (I-98) | (Ia-18) | (b2-c-27) |
| (I-99) | (Ia-19) | (b2-c-27) |
| (I-100) | (Ia-20) | (b2-c-27) |
| (I-101) | (Ia-1) | (b2-c-30) |
| (I-102) | (Ia-2) | (b2-c-30) |
| (I-103) | (Ia-3) | (b2-c-30) |
| (I-104) | (Ia-4) | (b2-c-30) |
| (I-105) | (Ia-5) | (b2-c-30) |
| (I-106) | (Ia-6) | (b2-c-30) |
| (I-107) | (Ia-7) | (b2-c-30) |
| (I-108) | (Ia-8) | (b2-c-30) |
| (I-109) | (Ia-9) | (b2-c-30) |
| (I-110) | (Ia-10) | (b2-c-30) |
| (I-111) | (Ia-11) | (b2-c-30) |
| (I-112) | (Ia-12) | (b2-c-30) |
| (I-113) | (Ia-13) | (b2-c-30) |
| (I-114) | (Ia-14) | (b2-c-30) |
| (I-115) | (Ia-15) | (b2-c-30) |
| (I-116) | (Ia-16) | (b2-c-30) |
| (I-117) | (Ia-17) | (b2-c-30) |
| (I-118) | (Ia-18) | (b2-c-30) |
| (I-119) | (Ia-19) | (b2-c-30) |
| (I-120) | (Ia-20) | (b2-c-30) |

TABLE 4

| Salt (I) | anion (I) | Cation (I) |
|---|---|---|
| (I-121) | (Ia-1) | (b2-c-31) |
| (I-122) | (Ia-2) | (b2-c-31) |
| (I-123) | (Ia-3) | (b2-c-31) |
| (I-124) | (Ia-4) | (b2-c-31) |
| (I-125) | (Ia-5) | (b2-c-31) |
| (I-126) | (Ia-6) | (b2-c-31) |
| (I-127) | (Ia-7) | (b2-c-31) |
| (I-128) | (Ia-8) | (b2-c-31) |
| (I-129) | (Ia-9) | (b2-c-31) |
| (I-130) | (Ia-10) | (b2-c-31) |
| (I-131) | (Ia-11) | (b2-c-31) |
| (I-132) | (Ia-12) | (b2-c-31) |
| (I-133) | (Ia-13) | (b2-c-31) |
| (I-134) | (Ia-14) | (b2-c-31) |
| (I-135) | (Ia-15) | (b2-c-31) |
| (I-136) | (Ia-16) | (b2-c-31) |
| (I-137) | (Ia-17) | (b2-c-31) |
| (I-138) | (Ia-18) | (b2-c-31) |
| (I-139) | (Ia-19) | (b2-c-31) |
| (I-140) | (Ia-20) | (b2-c-31) |

Among these specific examples, the salt (I) is preferably salt (I-1), salt (I-2), salt (I-3), salt (I-4), salt (I-5), salt (I-6), salt (I-7), salt (I-9), salt (I-11), salt (I-15), salt (I-16), salt (I-17), salt (I-18), salt (I-21), salt (I-22), salt (I-23), salt (I-24), salt (I-25), salt (I-26), salt (I-27), salt (I-29), salt (I-31), salt (I-35), salt (I-36), salt (I-37), salt (I-38), salt (I-41), salt (I-42), salt (I-43), salt (I-44), salt (I-45), salt (I-46), salt (I-47), salt (I-49), salt (I-51), salt (I-55), salt (I-56), salt (I-57), salt (I-58), salt (I-61), salt (I-62), salt (I-63), salt (I-64), salt (I-65), salt (I-66), salt (I-67), salt (I-69), salt (I-71), salt (I-75), salt (I-76), salt (I-77), salt (I-78), salt (I-81), salt (I-82), salt (I-83), salt (I-84), salt (I-85), salt (I-86), salt (I-87), salt (I-89), salt (I-91), salt (I-95), salt (I-96), salt (I-97), salt (I-98), salt (I-101), salt (I-102), salt (I-103), salt (I-104), salt (I-105), salt (I-106), salt (I-107), salt (I-109), salt (I-111), salt (I-115), salt (I-116), salt (I-117), salt (I-118), salt (I-121), salt (I-122), salt (I-123), salt (I-124), salt (I-125), salt (I-126), salt (I-127), salt (I-129), salt (I-131), salt (I-135), salt (I-136), salt (I-137) or salt (I-138).

The process for producing the salt (I) will be illustrated.

When the salt (I) is represented by formula (I1), that is formula (I) in which $X^1$ represents *—CO—O— where * represents a binding position to $C(Q^1)(Q^2)$ or $C(R^1)(R^2)$, the salt can be produced by reacting a salt represented by the formula (I1-a) with the compound represented by formula (I1-b) in a solvent such as chloroform or acetonitrile:

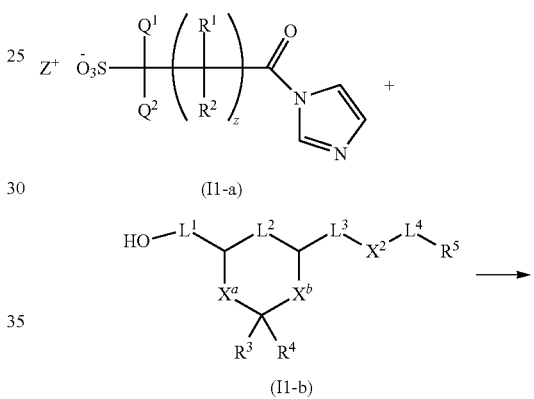

(I1-a)

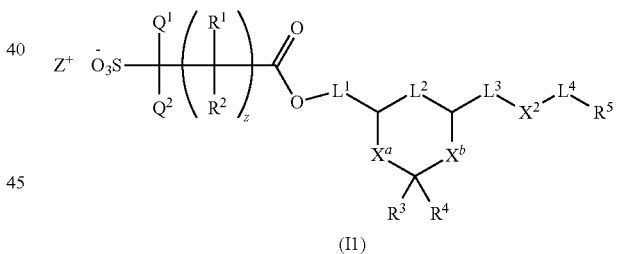

(I1-b)

(I1)

wherein $Q^1$, $Q^2$, $X^a$, $X^b$, $L^1$, $L^2$, $L^3$, $L^4$, $R^1$, $R^2$, $R^3$, $R^4$, $R^5$, z and $Z^+$ are the same as defined above.

The above-mentioned reaction is usually conducted at about 5 to 80° C. typically for 0.5 to 24 hours.

Specific examples of the compound represented by the formula (I1-b) include the following ones. These compounds are available in the market.

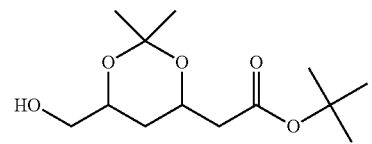

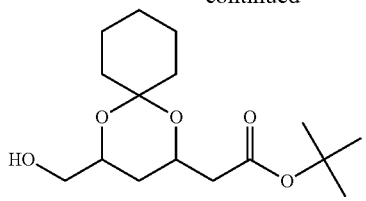

The compound represented by the formula (I1-a) can be produced by reacting a salt represented by the formula (I1-c) with the compound represented by formula (I1-d), that is carbonyldiimidazole, in a solvent such as chloroform or acetonitrile:

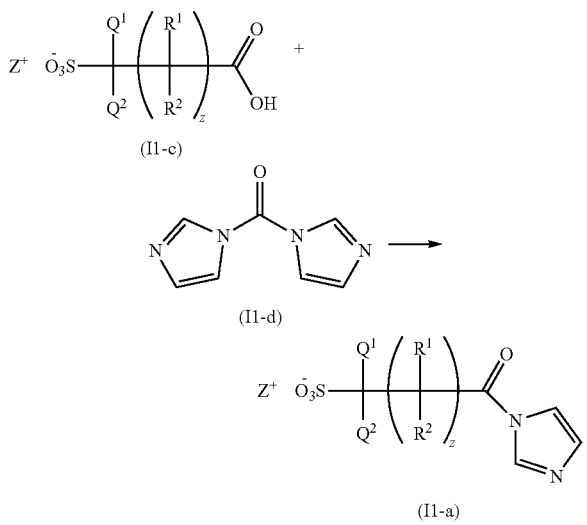

wherein $Q^1$, $Q^2$, $R^1$, $R^2$, z and $Z^+$ are the same as defined above.

The above-mentioned reaction is usually conducted at about 5 to 80° C. typically for 0.5 to 24 hours.

Specific examples of the salt represented by the formula (I1-c) include the following one. The salt represented by the formula (I1-c) can be produced in the same manner as a method described in JP2008-127367A.

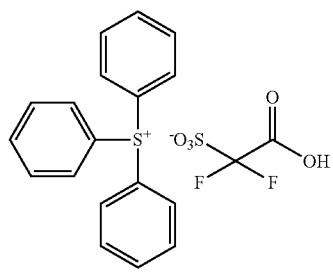

When the salt (I) is represented by formula (I2), that is formula (I) in which L represents *-$L^{I4}$-Ad-$L^{I5}$-O—CO—O-$L^{I6}$- where $L^{I4}$, $L^{I5}$ and $L^{I6}$ each independently represent a single bond or C1-C6 alkanediyl group, Ad represents an adamantanediyl group, * is a binding position to $X^1$, the salt can be produced by reacting a salt represented by the formula (I2-a) with the compound represented by formula (I1-b) in a solvent such as chloroform or acetonitrile:

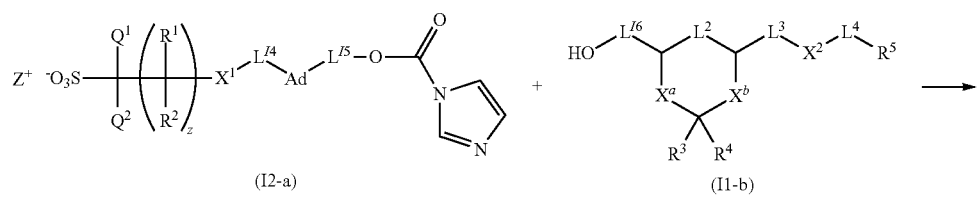

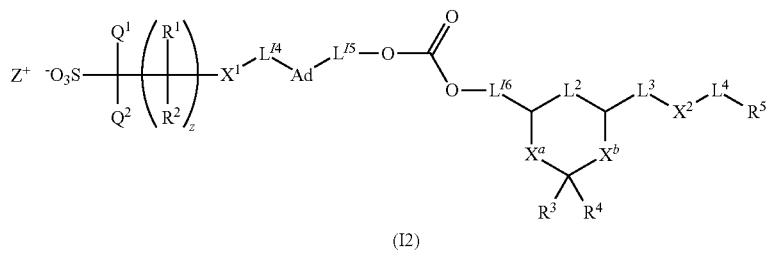

wherein $Q^1$, $Q^2$, $X^a$, $X^b$, $L^2$, $L^3$, $L^4$, $R^1$, $R^2$, $R^3$, $R^4$, $R^5$, z and $Z^+$ are the same as defined above.

The above-mentioned reaction is usually conducted at about 5 to 80° C. typically for 0.5 to 24 hours.

Specific examples of the salt represented by the formula (I2-a) include the following one. The salt represented by the formula (I2-a) can be produced in the same manner as a method described in JP2012-72109A.

The above-mentioned reaction is usually conducted at about 5 to 80° C. typically for 0.5 to 24 hours.

Specific examples of the salt represented by the formula (I3-a) include the following one. The salt represented by the formula (I3-a) can be produced in the same manner as a method described in JP2012-193170A.

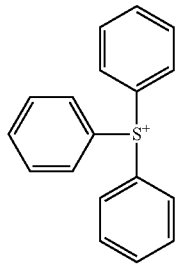

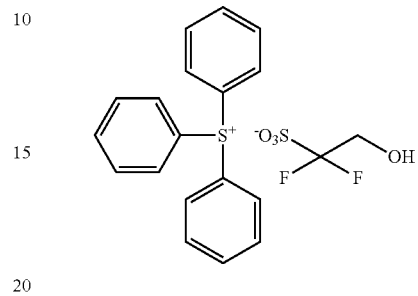

Specific examples of the compound represented by the formula (I3-b) include the following one. The compound represented by the formula (I3-b) is available on the market.

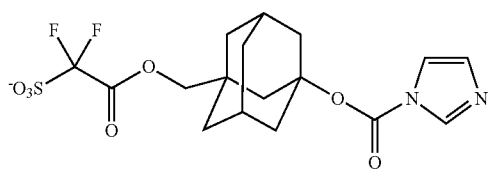

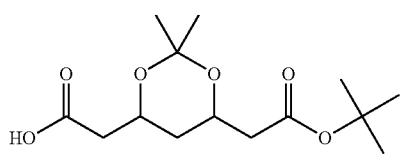 [SMILES: CC(C)(C)OC(=O)CC1CC(CC(=O)O)OC(C)(C)O1]

When the salt (I) is represented by formula (I3), that is formula (I) in which $X^1$ represents *—O—CO— where * represents a binding position to $C(Q^1)(Q^2)$ or $C(R^1)(R^2)$, the salt can be produced by reacting the compound represented by formula (I3-b) with carbonylimidazole in a solvent such as chloroform or acetonitrile, followed by reacting the obtained one with a salt represented by the formula (I3-a) in a solvent such as chloroform or acetonitrile:

When the salt (I) is represented by formula (I4), that is formula (I) in which $X^1$ represents —O—CO—O—, the salt can be produced by reacting a salt represented by the formula (I3-a) with carbonylimidazole in a solvent such as chloroform or acetonitrile, followed by reacting the obtained

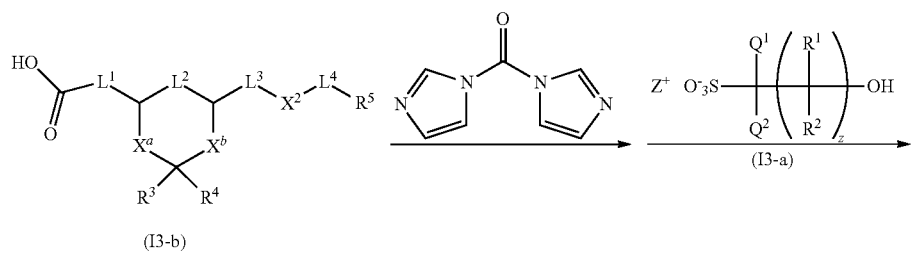

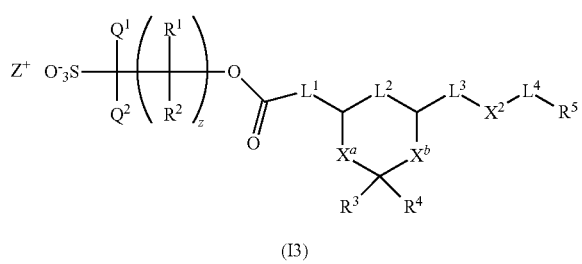

wherein Q 1, $Q^2$, $X^a$ $X^b$, $L^1$, $L^2$, $L^3$, $L^4$, $R^1$, $R^2$, $R^3$, $R^4$, $R^5$, z and $Z^+$ are the same as defined above.

one with the compound represented by formula (I1-b) in a solvent such as chloroform or acetonitrile:

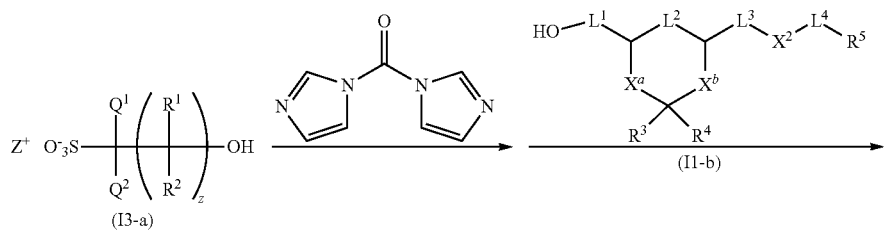

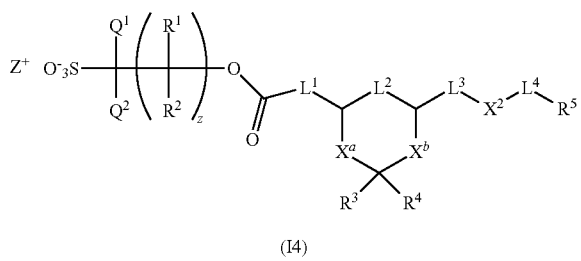

wherein $Q^1$, $Q^2$, $X^a$, $X^b$, $L^1$, $L^2$, $L^3$, $L^4$, $R^1$, $R^2$, $R^3$, $R^4$, $R^5$, z and $Z^+$ are the same as defined above.

The above-mentioned reaction is usually conducted at about 5 to 80° C. typically for 0.5 to 24 hours.

When the salt (I) is represented by formula (I5), that is formula (I) in which $X^1$ represents —O—, the salt can be produced by reacting a salt represented by the formula (I3-a) with the compound represented by formula (I1-b) in the presence of a base such as potassium hydroxide, in a solvent such as chloroform, acetonitrile, tetrahydropiran, or dimethylformuamide:

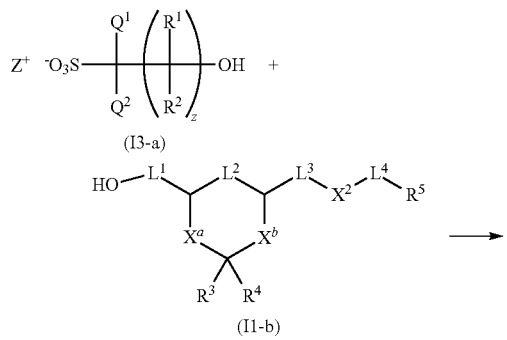

-continued

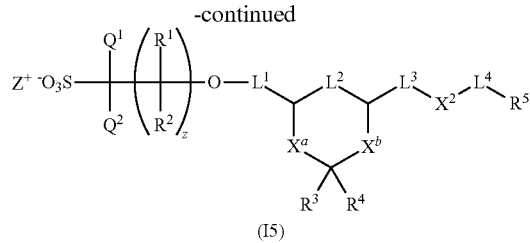

wherein $Q^1$, $Q^2$, $X^a$, $X^b$, $L^1$, $L^2$, $L^3$, $L^4$, $R^1$, $R^2$, $R^3$, $R^4$, $R^5$, z and $Z^+$ are the same as defined above.

The above-mentioned reaction is usually conducted at about 5 to 80° C. typically for 0.5 to 24 hours.

When the salt (I) is represented by formula (I6), that is formula (I) in which $L^1$ represents *-$L^{l4}$-Ad-$L^{l5}$-CO—O-$L^{l6}$- where $L^{l4}$, $L^{l5}$ and $L^{l6}$ each independently represent a single bond or C1-C6 alkanediyl group, Ad represents an adamantanediyl group, * is a binding position to $X^1$, the salt can be produced by reacting a salt represented by the formula (I6-a) with carbonylbiimidazole in a solvent such as chloroform or acetonitrile, followed by reacting the obtained one with a compound represented by formula (I1-b):

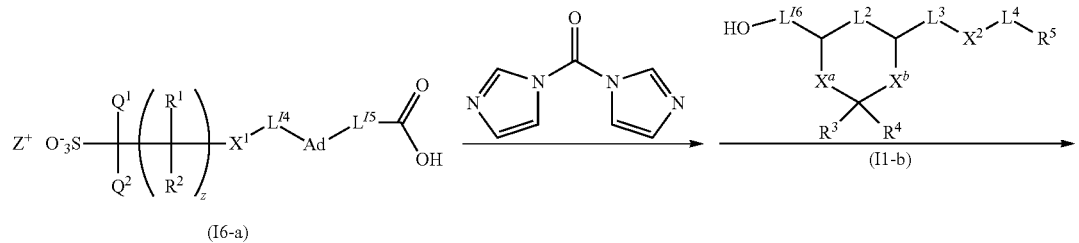

-continued

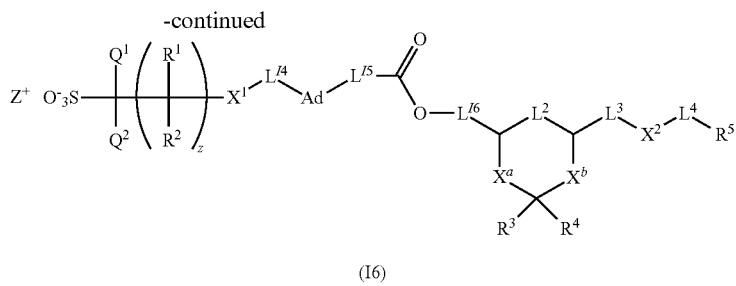

(I6)

wherein $Q^1$, $Q^2$, $X^a$, $X^b$, $L^2$, $L^3$, $L^4$, $R^1$, $R^2$, $R^3$, $R^4$, $R^5$, z and $Z^+$ are the same as defined above.

The above-mentioned reaction is usually conducted at about 5 to 80° C. typically for 0.5 to 24 hours.

Specific examples of the salt represented by the formula (I6-a) include the following ones. The salt represented by the formula (I6-a) can be produced in the same manner as a method described in JP2011-046694A.

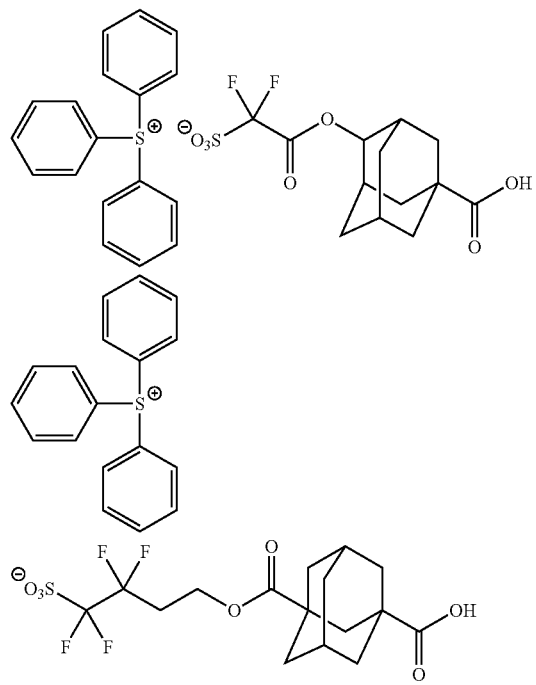

<Acid Generator>

The acid generator of the disclosure comprises the salt (I). The acid generator may contain two or more kinds of the salt (I). The acid generator may contain one or more known acid generator in addition to the salt (I).

In the photoresist composition, an acid generates from the acid generator by light for lithography. The acid catalytically acts against an acid-labile group in the resin to cleave the acid-labile group.

The acid generator known in the art may be a nonionic acid generator or an ionic acid generator. Examples of the nonionic acid generator include an organo-halogen compound, a sulfonate compound such as a 2-nitrobenzylsulfonate, an aromatic sulfonate, an oxime sulfonate, an N-sulfonyloxyimide, a sulfonyloxyketone and diazonaphthoquinone 4-sulfonate, and a sulfone compound such as a disulfone, a ketosulfone and a sulfonyldiazomethane. Examples of the ionic acid generator include an onium salt compound such as a diazonium salt, a phosphonium salt, a sulfonium salt and an iodonium salt. Examples of the anion of the onium salt include a sulfonic acid anion, a sulfonylimide anion and a sulfonylmethide anion.

Specific examples of the acid generator known in the art include acid generators described in JP63-26653A, JP55-164824A, JP62-69263 A, JP63-146038A, JP63-163452A, JP62-153853A, JP63-146029A, U.S. Pat. Nos. 3,779,778, 3,849,137, DE Patent No. 3914407 and EP Patent No. 126,712. Other examples of that include acid generators described in JP2013-68914A, JP2013-3155A and JP2013-11905A.

The acid generator for the photoresist composition is preferably a fluorine-containing acid generator, and more preferably a fluorine-containing organic sulfonate acid generator.

Preferable examples of the acid generator include a salt represented by the formula (B1):

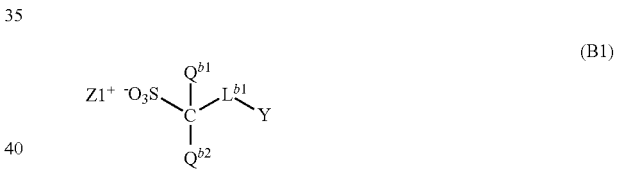

(B1)

wherein $Q^{b1}$ and $Q^{b2}$ each independently represent a fluorine atom or a C1-C6 perfluoroalkyl group, $L^{b1}$ represents a single bond or a C1-C24 divalent saturated hydrocarbon group in which a methylene group can be replaced by —O— or —CO— and in which a hydrogen atom can be replaced by a fluorine atom or a hydroxy group, and Y represents a methyl group which can have a substituent or a C3-C18 monovalent alicyclic hydrocarbon group which can have a substituent and in which a methylene group can be replaced by —O—, —CO— or —SO$_2$—, and $Z1^+$ represents an organic cation.

Hereinafter, the salt represented by the formula (B1) is sometimes referred to as "Salt (B1)".

For $Q^{b1}$ and $Q^{b2}$, examples of the perfluoroalkyl group include examples of those for $Q^1$ and $Q^2$, and a trifluoromethyl group is preferred. $Q^{b1}$ and $Q^{b2}$ each independently preferably represent a fluorine atom or a trifluoromethyl group, and $Q^{b1}$ and $Q^{b2}$ are more preferably fluorine atoms.

For $L^{b1}$, examples of the saturated hydrocarbon group in which a methylene group has been replaced by an oxygen atom or a carbonyl group include those represented by formulae (b1-1), (b1-2) and (b1-3).

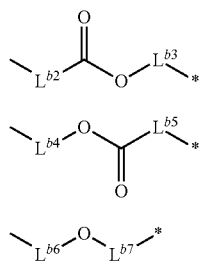

(b1-1)

(b1-2)

(b1-3)

In formula (b1-1), $L^{b2}$ represents a single bond or a C1-C22 divalent saturated hydrocarbon group where a hydrogen atom may be replaced by a fluorine atom, and $L^{b3}$ represents a single bond or a C1-C22 divalent saturated hydrocarbon group where a hydrogen atom may be replaced by a hydroxyl group or a fluorine atom and where a methylene group may be replaced by an oxygen atom or carbonyl group, provided that total number of the carbon atoms of $L^{b2}$ and $L^{b3}$ is up to 22.

In formula (b1-2), $L^{b4}$ represents a C1-C22 divalent saturated hydrocarbon group where a hydrogen atom may be replaced by a fluorine atom, and $L^{b5}$ represents a single bond or a C1-C22 divalent saturated hydrocarbon group where a hydrogen atom may be replaced by a hydroxyl group or a fluorine atom and where a methylene group may be replaced by an oxygen atom or carbonyl group, provided that the total carbon atoms of $L^{b4}$ and $L^{b5}$ is up to 22.

In formula (b1-3), $L^{b6}$ represents a single bond or a C1-C23 divalent saturated hydrocarbon group where a hydrogen atom may be replaced by a fluorine atom, and $L^{b7}$ represents a single bond or a C1-C22 divalent saturated hydrocarbon group where a hydrogen atom may be replaced by a hydroxyl group or a fluorine atom and where a methylene group may be replaced by an oxygen atom or carbonyl group, with the proviso that total carbon number of $L^{b6}$ and $L^{b7}$ is up to 23 and with the proviso that formula (b1-3) excludes a group having a structure represented by -$L^{b6}$-O-CO-.

In these formulae, * represents a binding position to Y.

In formulae (b1-1), (b1-2) and (b1-3), the divalent saturated hydrocarbon group includes linear chain alkanediyl groups, branched chain alkanediyl groups, monocyclic or polycyclic divalent saturated hydrocarbon groups, and a group combining two or more of the above-mentioned groups.

$L^{b2}$ is preferably a single bond.

$L^{b3}$ is preferably a C1-C4 divalent saturated hydrocarbon group.

$L^{b4}$ is preferably a C1-C8 divalent saturated hydrocarbon group where a hydrogen atom may be replaced by a fluorine atom.

$L^{b5}$ is preferably a single bond or a C1-C8 divalent saturated hydrocarbon group.

$L^{b6}$ is preferably a single bond or a C1-C4 divalent saturated hydrocarbon group where a hydrogen atom may be replaced by a fluorine atom.

$L^{b7}$ is preferably a single bond or a C1-C7 divalent saturated hydrocarbon group where a hydrogen atom may be replaced by a hydroxyl group or a fluorine atom and where a methylene group may be replaced by an oxygen atom or carbonyl group.

Among them, those of formulae (b1-1) and (b1-3) are preferred.

Examples of the group represented by formula (b1-1) include those represented by formulae (b1-4), (b1-5), (b1-6), (b1-7) and (b1-8)

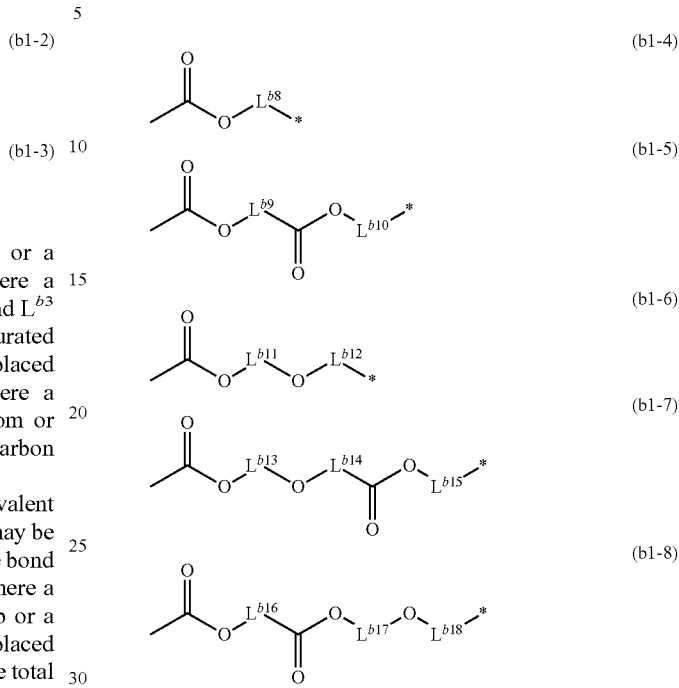

In formula (b1-4), $L^{b8}$ represents a single bond or a C1-C22 divalent saturated hydrocarbon group where a hydrogen atom may be replaced by a fluorine atom or a hydroxyl group.

In formula (b1-5), $L^{b9}$ represents a C1-C20 divalent saturated hydrocarbon group, and $L^{b10}$ represents a single bond or a C1-C19 divalent saturated hydrocarbon group where a hydrogen atom may be replaced by a hydroxyl group or a fluorine atom, provided that the total carbon atoms of $L^{b10}$ and $L^{b9}$ is up to 20.

In formula (b1-6), $L^{b11}$ represents a C1-C21 divalent saturated hydrocarbon group, and $L^{b12}$ represents a single bond or a C1-C20 divalent saturated hydrocarbon group where a hydrogen atom may be replaced by a hydroxyl group or a fluorine atom, with the proviso that total carbon number of L and $L^{b2}$ is up to 21.

In formula (b1-7), $L^{b13}$ represents a C1-C19 divalent saturated hydrocarbon group, $L^{b14}$ represents a single bond or a C1-C18 divalent saturated hydrocarbon group, and $L^{b15}$ represents a single bond or a C1-C18 divalent saturated hydrocarbon group where a hydrogen atom may be replaced by a hydroxyl group or a fluorine atom, with the proviso that total carbon number of $L^{b13}$, $L^{b14}$ and $L^{b15}$ is up to 19.

In formula (b1-8), $L^{b}16$ represents a C1-C18 divalent saturated hydrocarbon group, $L^{b7}$ represents a C1-C18 divalent saturated hydrocarbon group, and $L^{b18}$ represents a single bond or a C1-C17 divalent saturated hydrocarbon group where a hydrogen atom may be replaced by a hydroxyl group or a fluorine atom, with the proviso that total carbon number of $L^{b16}$, $L^{b17}$ and $L^{b18}$ is up to 19.

In these formulae, * represents a binding position, * represents a binding position to Y.

In these formulae, the divalent saturated hydrocarbon group includes linear chain alkanediyl groups, branched chain alkanediyl groups, monocyclic or polycyclic divalent saturated hydrocarbon groups, and a group combining two or more of the above-mentioned groups.

Specific examples of the divalent saturated hydrocarbon group include those as referred to for $L^{b1}$.

$L^{b8}$ is preferably a C1-C4 alkanediyl group.

$L^{b9}$ is preferably a C1-C8 divalent saturated hydrocarbon group.

$L^{b11}$ is preferably a single bond or a C1-C19 divalent saturated hydrocarbon group, and more preferably a single bond or a C1-C8 divalent saturated hydrocarbon group.

$L^{b11}$ is preferably a C1-C8 divalent saturated hydrocarbon group.

$L^{b12}$ is preferably a single bond or a C1-C8 divalent saturated hydrocarbon group.

$L^{b13}$ is preferably a C1-C12 divalent saturated hydrocarbon group.

$L^{b14}$ is preferably a single bond or a C1-C6 divalent saturated hydrocarbon group.

$L^{b15}$ is preferably a single bond or a C1-C18 divalent saturated hydrocarbon group, and more preferably a single bond or a C1-C8 divalent saturated hydrocarbon group.

$L^{b16}$ is preferably a C1-C12 divalent saturated hydrocarbon group.

$L^{b17}$ is preferably a C1-C6 divalent saturated hydrocarbon group.

$L^{b18}$ is preferably a single bond or a C1-C17 divalent saturated hydrocarbon group, and more preferably a single bond or a C1-C4 divalent saturated hydrocarbon group.

Examples of the group represented by formula (b1-3) include those represented by formulae (b1-9), (b1-10) and (b1-11).

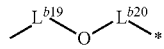
(b1-9)

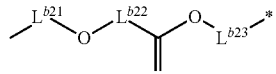
(b1-10)

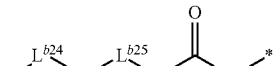
(b1-11)

In formula (b1-9), $L^{b19}$ represents a single bond or a C1-C23 divalent saturated hydrocarbon group where a hydrogen atom may be replaced by a fluorine atom, and $L^{b20}$ represents a single bond or a C1-C23 divalent saturated hydrocarbon group where a hydrogen atom may be replaced by a hydroxyl group or a fluorine atom and where a methylene group may be replaced by an oxygen atom or carbonyl group, provided that the total carbon atoms of $L^{b19}$ and $L^{b}20$ is up to 23.

In formula (b1-10), $L^{b21}$ represents a single bond or a C1-C21 divalent saturated hydrocarbon group where a hydrogen atom may be replaced by a fluorine atom, $L^{b22}$ represents a single bond or a C1-C21 divalent saturated hydrocarbon group and $L^{b23}$ represents a single bond or a C1-C21 divalent saturated hydrocarbon group where a hydrogen atom may be replaced by a hydroxyl group or a fluorine atom and where a methylene group may be replaced by an oxygen atom or a carbonyl group, provided that the total carbon atoms of $L^{b21}$, $L^{b22}$ and $L^{b23}$ is up to 21.

In formula (b1-11), $L^{b24}$ represents a C1-C21 divalent saturated hydrocarbon group where a hydrogen atom may be replaced by a fluorine atom, $L^{b25}$ represents a C1-C21 divalent saturated hydrocarbon group, and $L^{b26}$ represents a single bond or a C1-C20 divalent saturated hydrocarbon group where a hydrogen atom may be replaced by a hydroxyl group or a fluorine atom and where a methylene group may be replaced by an oxygen atom or a carbonyl group, provided that the total carbon atoms of $L^{b24}$, $L^{b25}$ and L is up to 21.

In these formulae,* represents a binding position to Y.

In these formulae, the divalent saturated hydrocarbon group includes linear chain alkanediyl groups, branched chain alkanediyl groups, monocyclic or polycyclic divalent saturated hydrocarbon groups, and a group combining two or more of the above-mentioned groups.

Specific examples of the divalent saturated hydrocarbon group include those as referred to for $L^{b1}$.

Examples of the divalent saturated hydrocarbon group where a methylene group has been replaced by an oxygen atom or a carbonyl group include what has an acyloxy group. In what has an acyloxy group, a hydrogen atom may be replaced by a hydroxyl group and a methylene group may be replaced by an oxygen atom or a carbonyl group.

Examples of what has an acyloxy group include an acetyloxy group, a propyonyloxy group, a butyryloxy group, a cyclohexylcarbonyloxy group and an adamantylcarbonyloxy group.

When a hydrogen atom has be replaced by a hydroxyl group or a methylene group has be replaced by an oxygen atom or a carbonyl group in what has an acyloxy group, examples of such a group include an oxoadamantylcarbonyloxy group, a hydroxyadamantylcarbonyloxy group, an oxocyclohexylcarbonyloxy group, and a hydroxycyclohexylcarbonyloxy group.

Examples of the group represented by formula (b1-4) include the following ones.

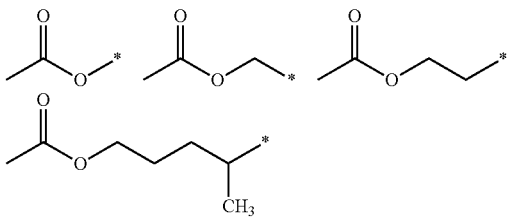

Examples of the group represented by formula (b1-5) include the following ones.

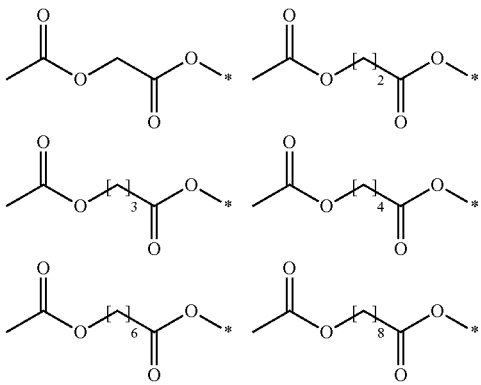

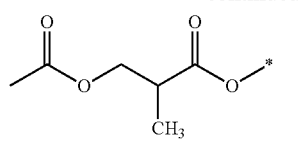
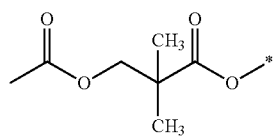
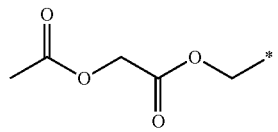
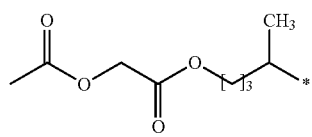
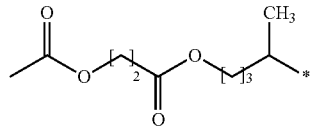
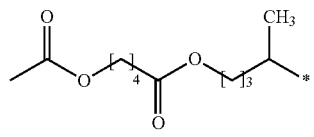
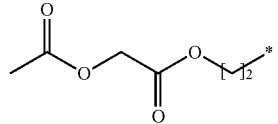
Examples of the group represented by formula (b1-6) include the following ones.
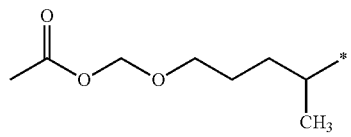
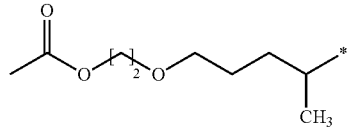
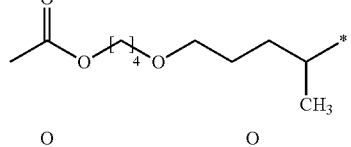
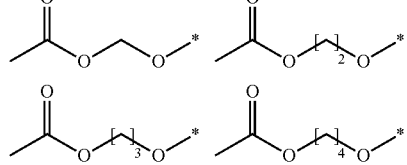
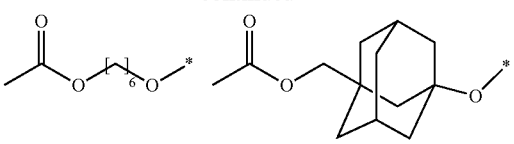
Examples of the group represented by formula (b1-7) include the following ones.
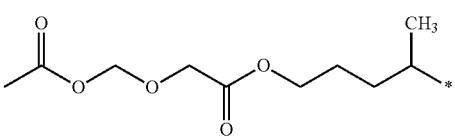
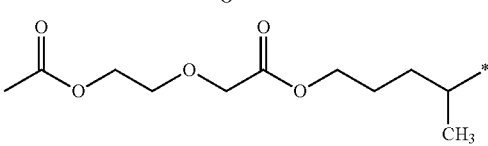
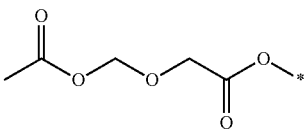
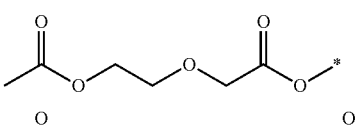
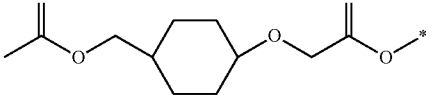
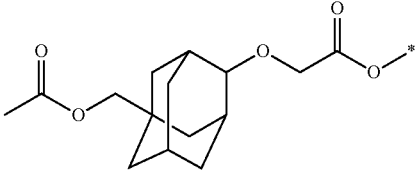
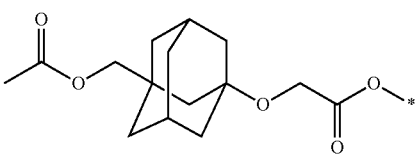
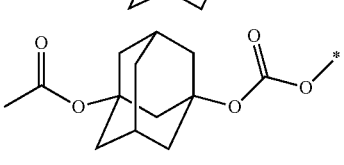

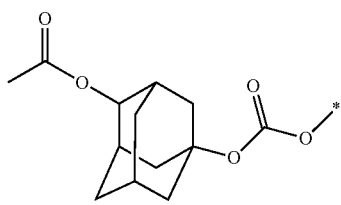
Examples of the group represented by formula (b1-8) include the following ones.
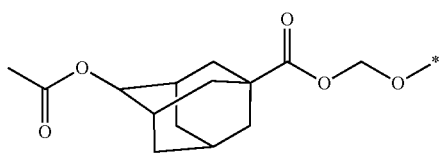
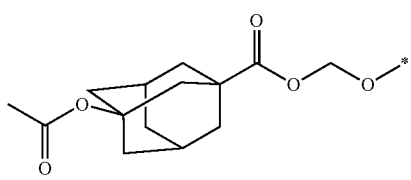
Examples of the group represented by formula (b1-2) include the following ones.
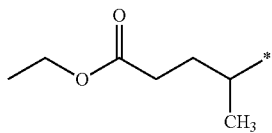
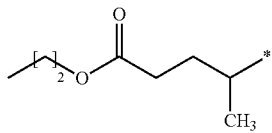
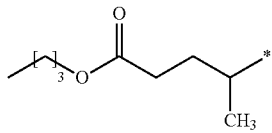
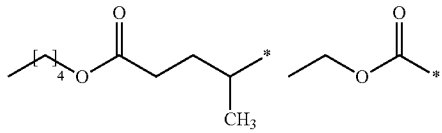
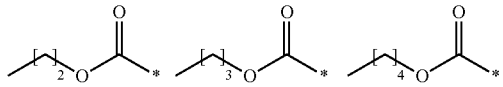
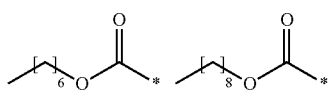
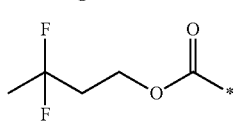
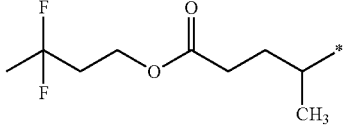
Examples of the group represented by formula (b1-9) include the following ones.
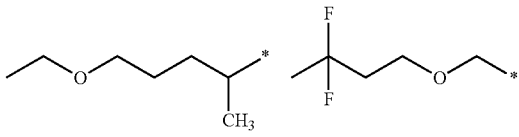
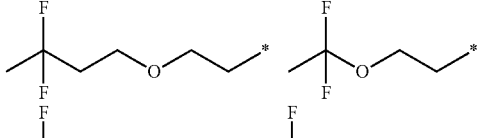
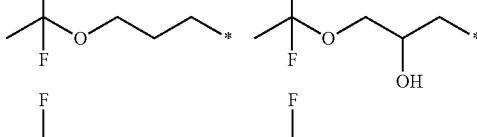
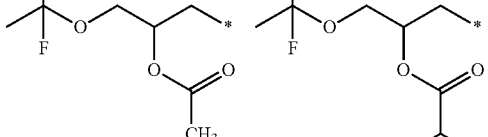
Examples of the group represented by formula (b1-10) include the following ones.
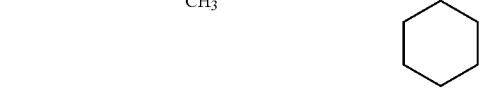
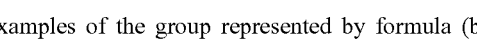
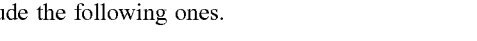
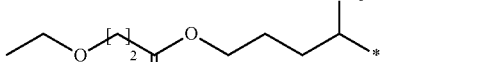
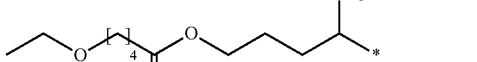
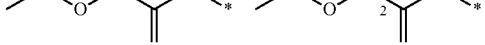
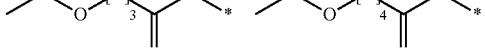
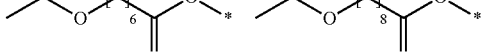

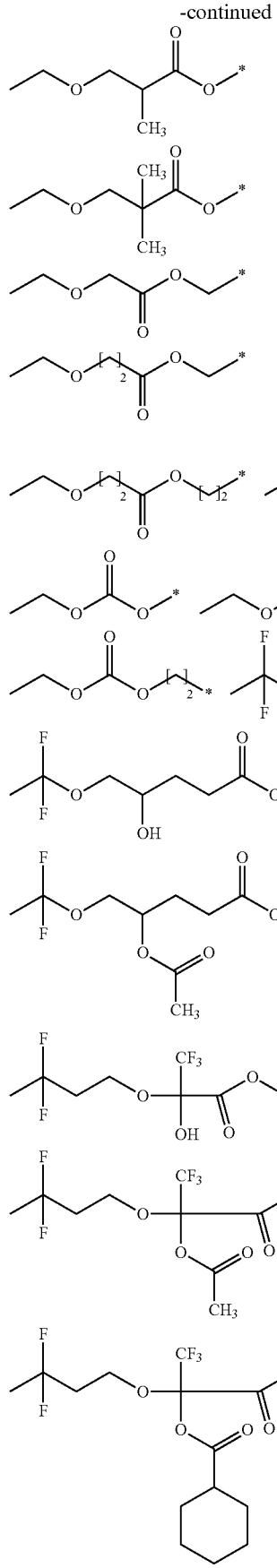
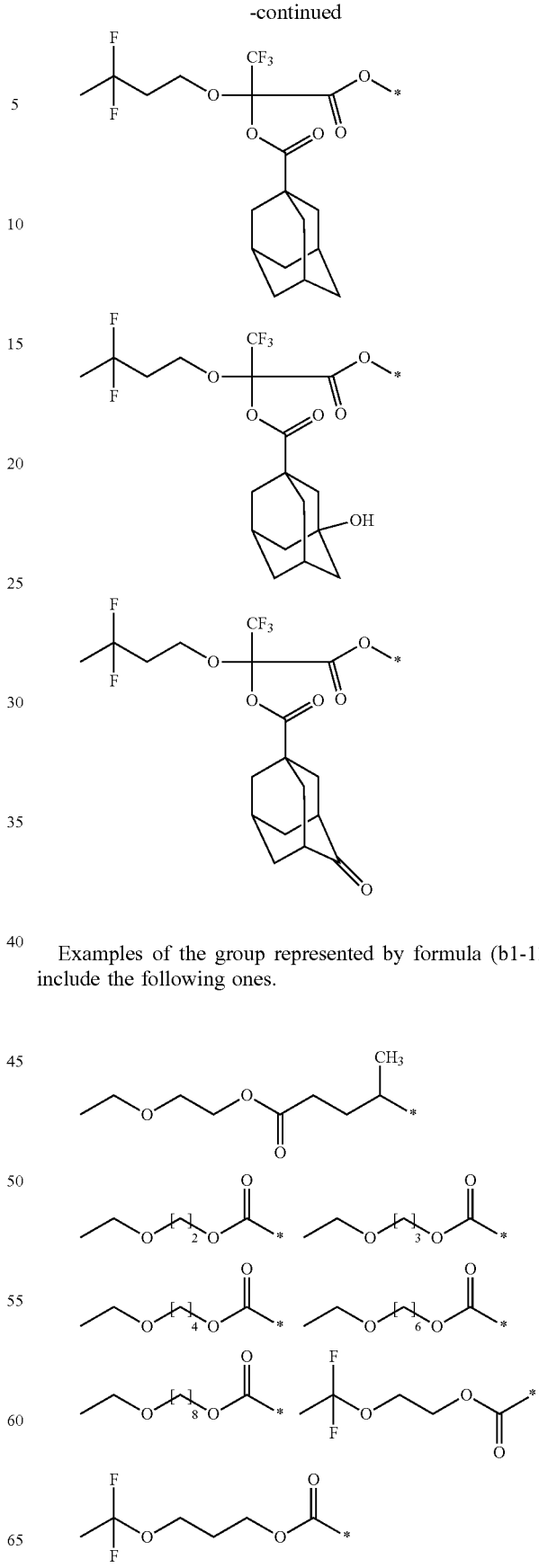
Examples of the group represented by formula (b1-11) include the following ones.

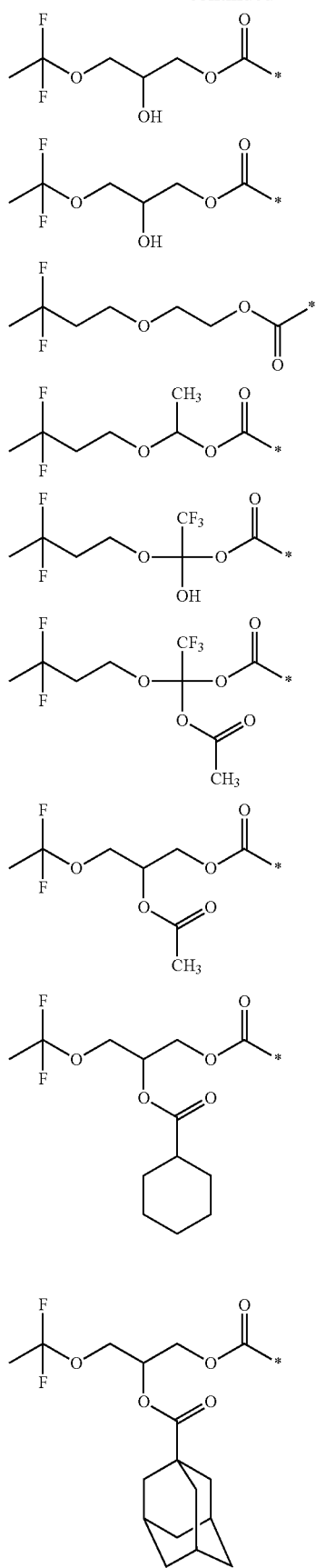

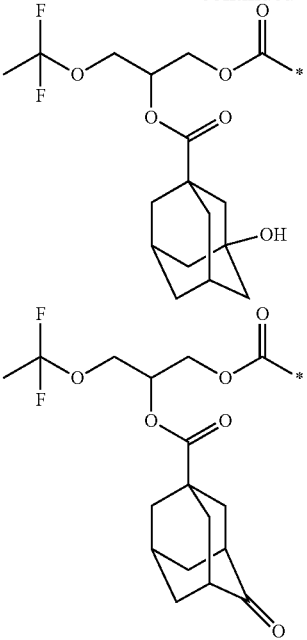

$L^{b1}$ is preferably one represented by formula (b1-4), more preferably *1-CO—O— $(CH_2)_t$— where "t" represents an integer of 0 to 6, *1 represents a binding position to —C($Q^1$)($Q^2$)-.

The monovalent alicyclic hydrocarbon group for Y may be a monocyclic one or polycyclic one such as a spiro ring.

Preferred examples of the alicyclic hydrocarbon group represented by Y include those represented by the formulae (Y1) to (Y11) and (Y36) to (Y38). Preferred examples of the alicyclic hydrocarbon group which is represented by Y and in which a methylene group has been replaced by —O—, —SO$_2$— or —CO— include those represented by the formulae (Y12) to (Y35) and Y(39) and Y(40).

 (Y1)

 (Y2)

 (Y3)

 (Y4)

 (Y5)

 (Y6)

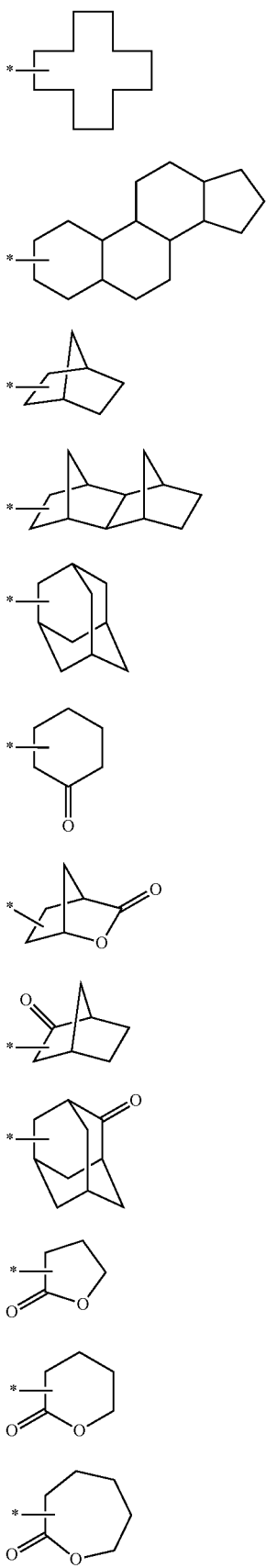
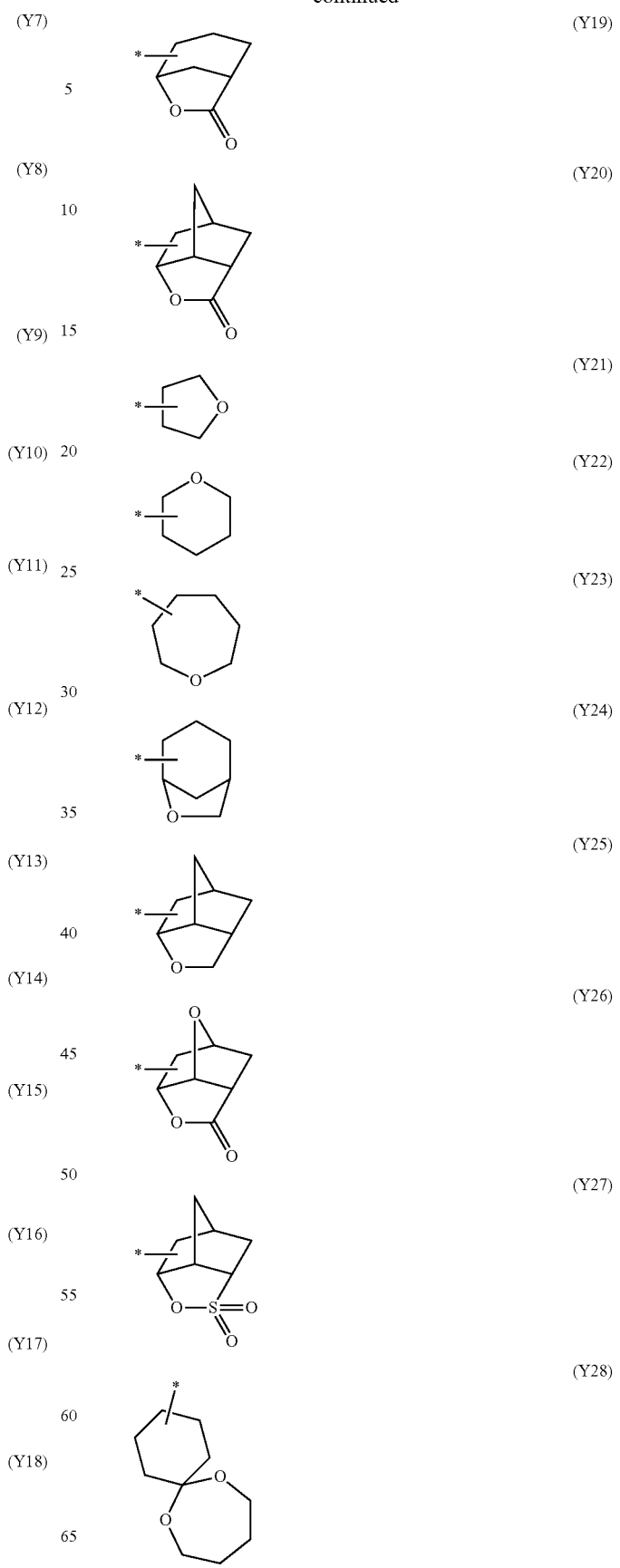

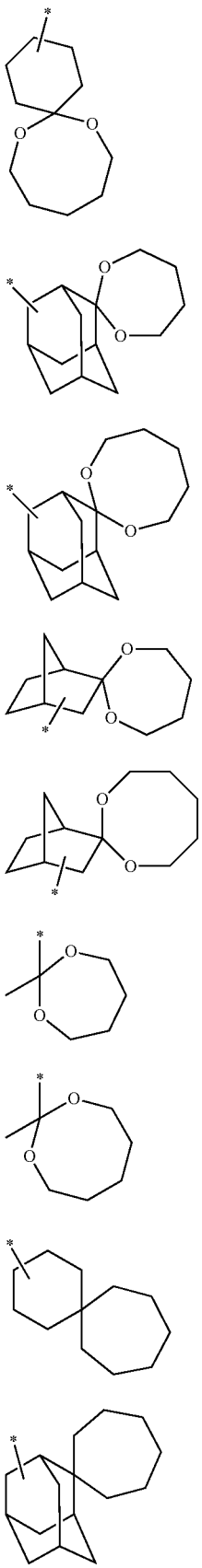

(Y29)
(Y30)
(Y31)
(Y32)
(Y33)
(Y34)
(Y35)
(Y36)
(Y37)

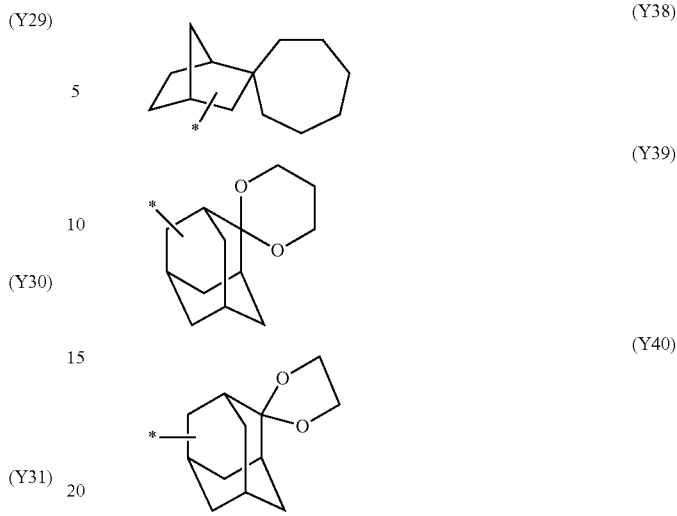

(Y38)
(Y39)
(Y40)

Among the groups represented by the formulae, preferred are those represented by formulae (Y1) to (Y20), (Y30), (Y31), (Y39) and (Y40); more preferred are those represented by the formulae (Y11), (Y15), (Y16), (Y19), (Y20), (Y30), (Y31), (Y39) and (Y40); and still more preferred are those represented by the formulae (Y11), (Y15), (Y30), (Y39) and (Y40).

Substituents on the methyl group for Y include a halogen atom, a hydroxyl group, a C3-C16 alicyclic hydrocarbon group, a C6-C18 aromatic hydrocarbon group, a glycidyloxy group, and —$(CH_2)_{j2}$—O—CO—$R^{b1'}$— in which $R^{b1'}$ is a C1-C16 alkyl group and j2 is an integer of 0 to 4.

Substituents on the alicyclic hydrocarbon groups for Y include a halogen atom, a hydroxyl group, a C1-C12 alkyl group, a C1-C12 hydroxy-containing alkyl group, a C1-C12 alkoxy group, a C3-C16 alicyclic hydrocarbon group, a C6-C18 aromatic hydrocarbon group, a C7-C21 aralkyl group, a C2-C4 acyl group, a glycidyloxy group, and —$(CH_2)_{j2}$—O—CO—$R^{b1'}$— in which $R^{b1'}$ is a C1-C16 alkyl group and j2 is an integer of 0 to 4.

Examples of the halogen atom include a fluorine atom, a chlorine atom, a bromine atom and an iodine atom.

Examples of the alicyclic hydrocarbon group include a cyclopentyl group, a cyclohexyl group, a cycloheptyl group and a cyclooctyl group, a norbornyl group and an adamantyl group.

Examples of the aromatic hydrocarbon group include an aryl group such as a phenyl group, a naphthyl group, an anthryl group, a p-methylphenyl group, a p-tert-butylphenyl group, a p-adamantylphenyl group, a tolyl group, a xylyl group, a cumyl group, a mesityl group, a biphenyl group, a phenanthryl group, a 2,6-diethylphenyl group and a 2-methyl-6-ethylphenyl group.

Examples of the alkyl group include a methyl group, an ethyl group, a propyl group, an isopropyl group, a butyl group, a sec-butyl group, a tert-butyl group, a pentyl group, a hexyl group, a heptyl group, a 2-ethylhexyl group and a dodecyl group.

Examples of hydroxyl-containing alkyl group include a hydroxymethyl group and a hydroxyethyl group.

Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the aralkyl group include a benzyl group, phenylpropyl group, a phenethyl group, a naphthylmethyl group, or a naphthylethyl group.
Examples of the acyl group include an acetyl group, a propyonyl group and a butyryl group.
Examples of Y include the groups as follow.
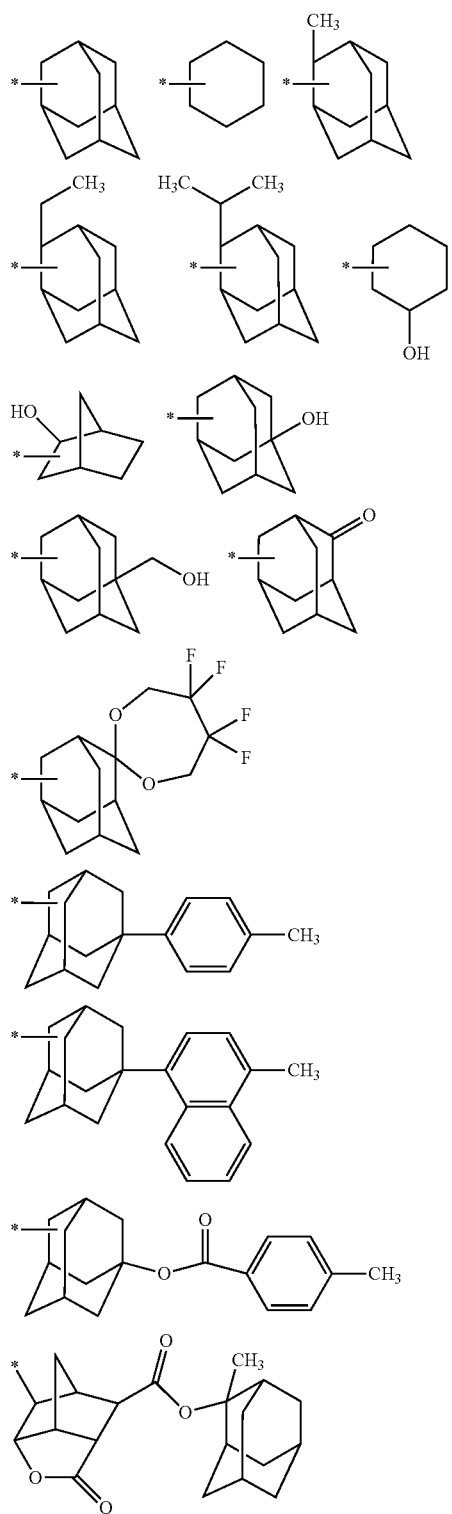
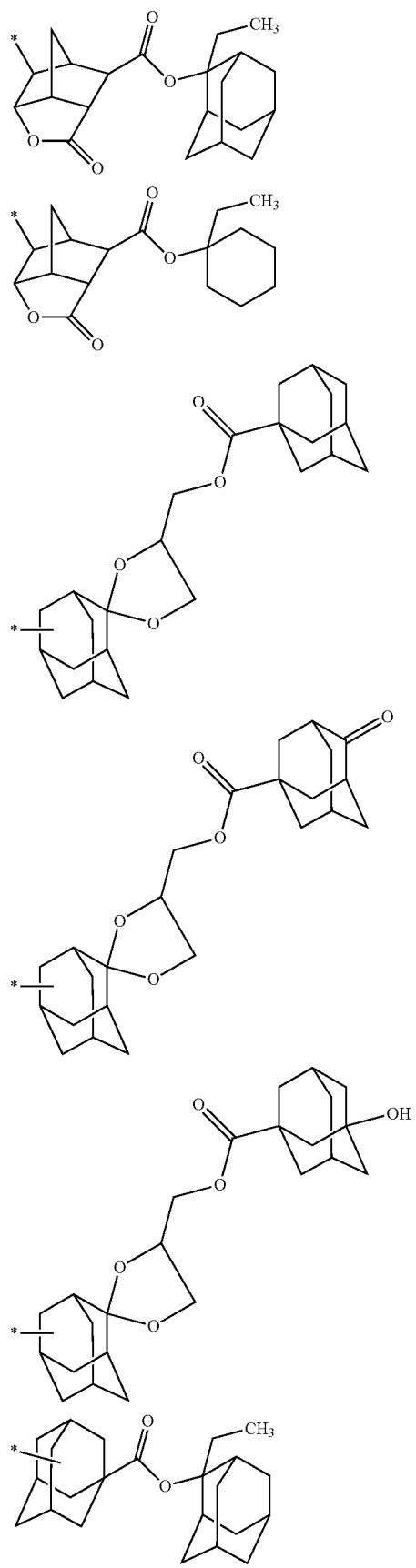

57
-continued
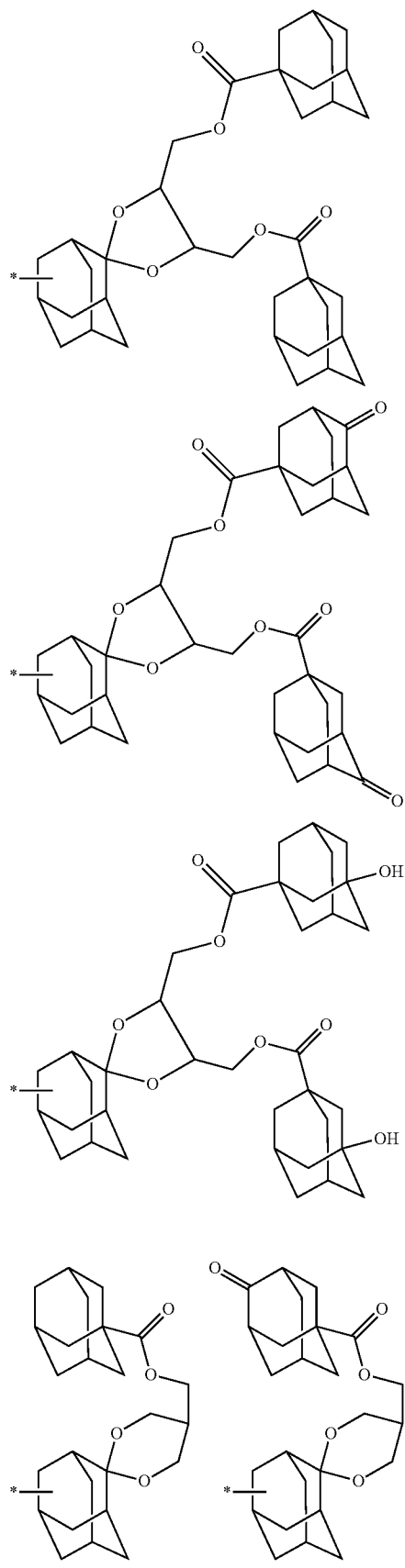
58
-continued
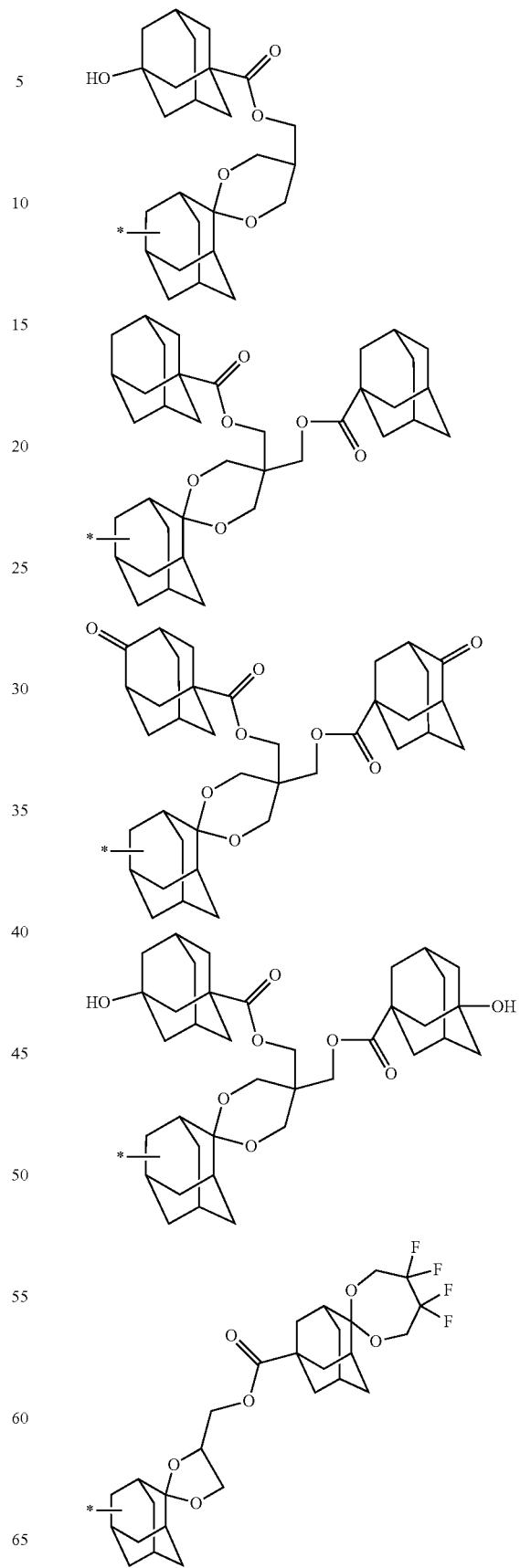

-continued

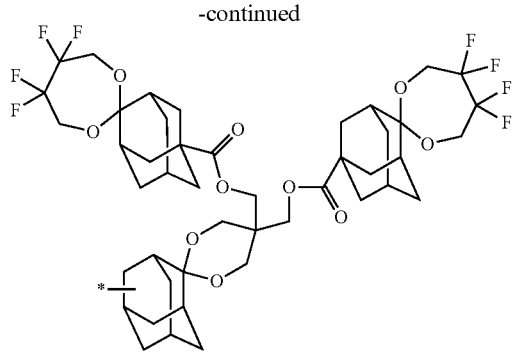

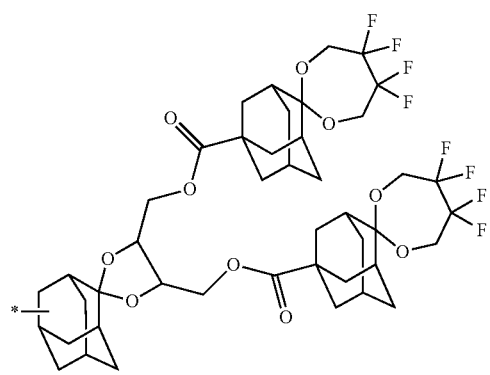

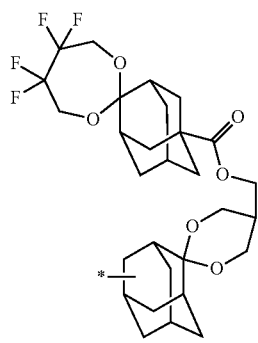

-continued

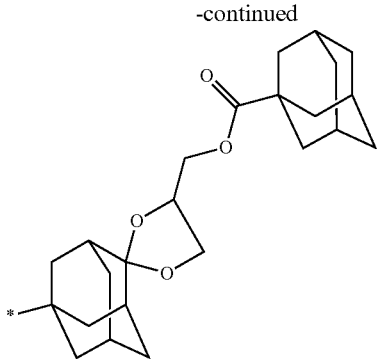

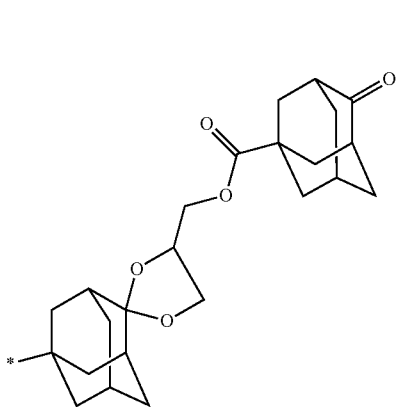

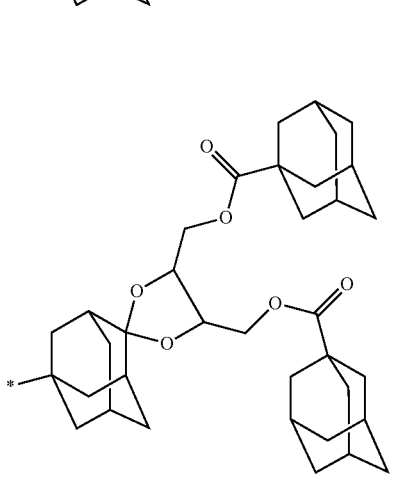

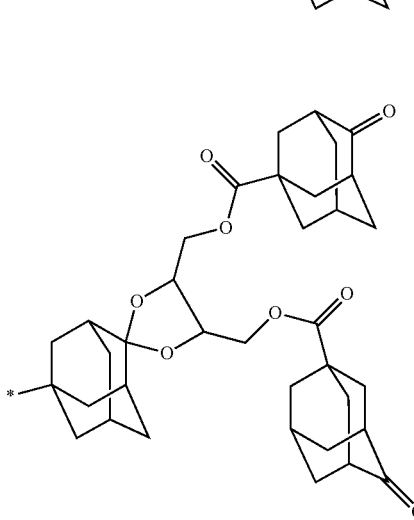

Y represents preferably a C3-C18 alicyclic hydrocarbon group which may have a substituent and in which a methylene group has been replaced by —O—, —SO$_2$— or —CO—, more preferably an amadantyl group which may have a substituent and in which a methylene group has been replaced by —O—, —SO$_2$— or —CO—, and still more preferably an amadantyl group, a hydroxyamadantyl group, an oxoamadantyl group, or the following group.

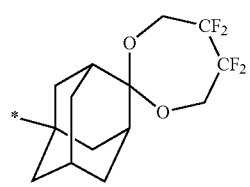

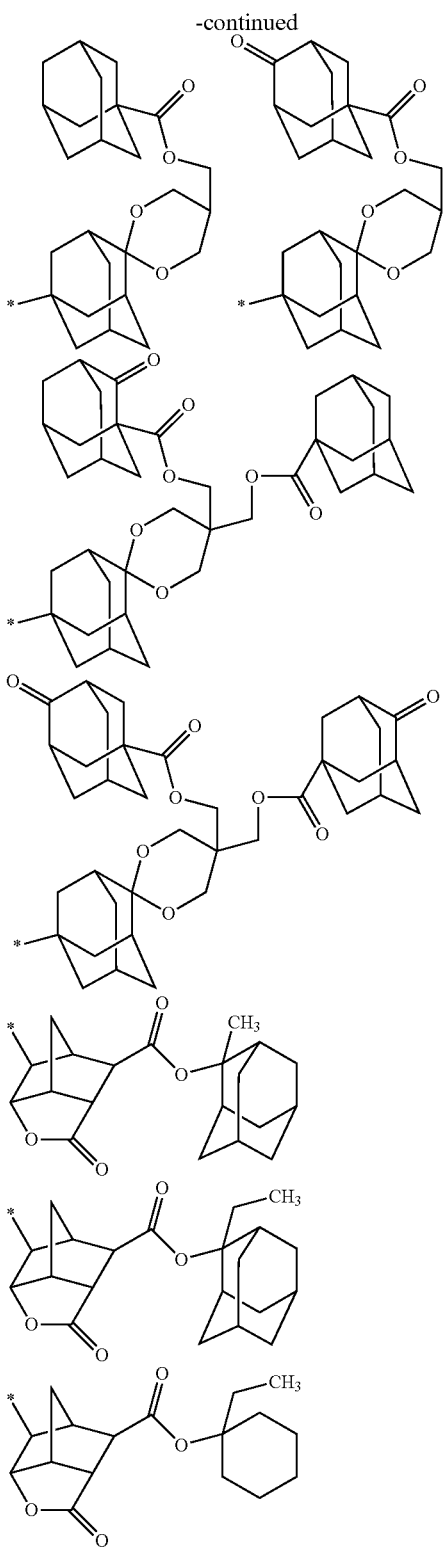
where * represents a binding position.
Preferred examples of the sulfonic acid anion of the salt represented by formula (B1) include salts represented by the formulae (B1-A-1) to (B1-A-55), preferably the formulae (B1-A-1) to (B1-A-4), (B1-A-9), (B1-A-10), (B1-A-24) to (B1-A-33), (B1-A-36) to (B1-A-40) and (B1-A-47) to (B1-A-55).
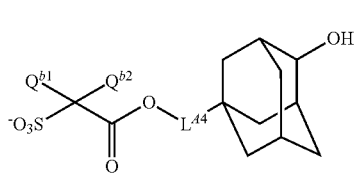
(B1-A-1)
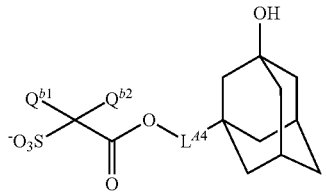
(B1-A-2)
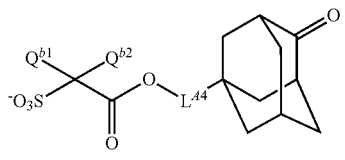
(B1-A-3)
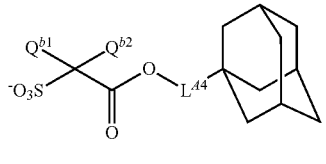
(B1-A-4)
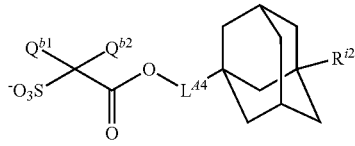
(B1-A-5)
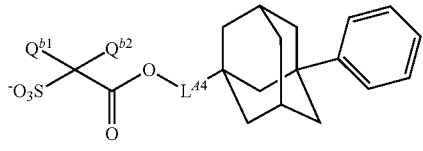
(B1-A-6)
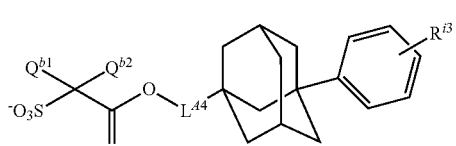
(B1-A-7)
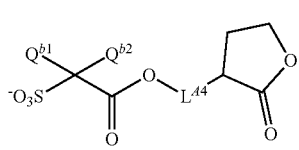
(B1-A-8)
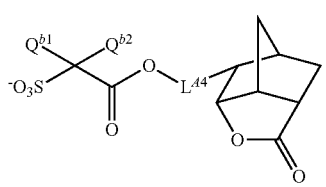
(B1-A-9)

-continued
(B1-A-10)
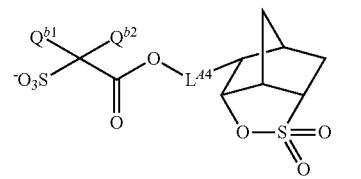
(B1-A-11)
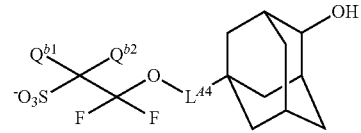
(B1-A-12)
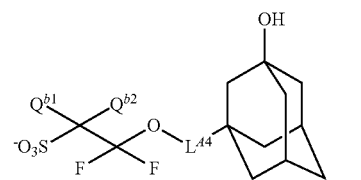
(B1-A-13)
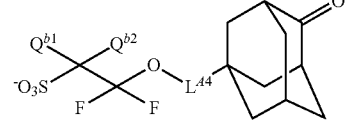
(B1-A-14)
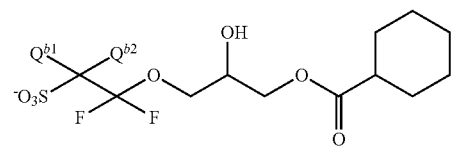
(B1-A-15)
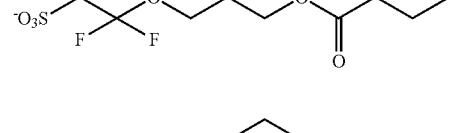
(B1-A-16)
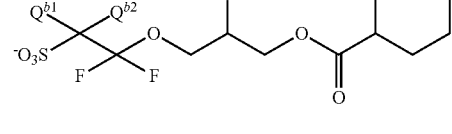
(B1-A-17)
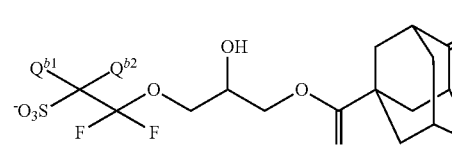
(B1-A-18)
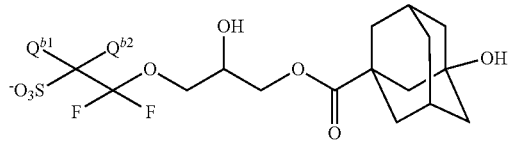
(B1-A-19)
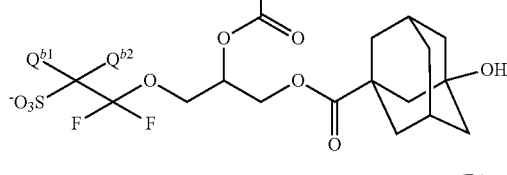
(B1-A-20)
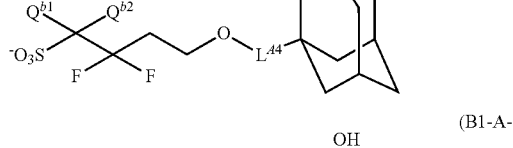
(B1-A-21)
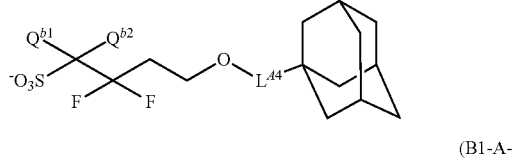
(B1-A-22)
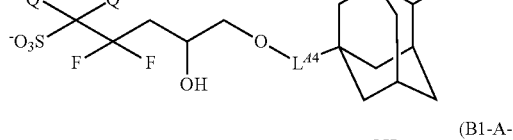
(B1-A-23)
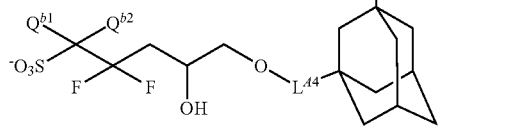
(B1-A-24)
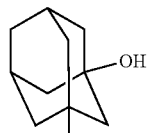
(B1-A-25)
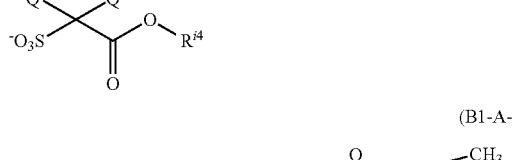

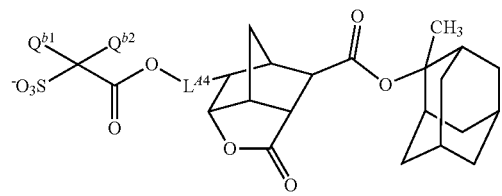
(B1-A-26)
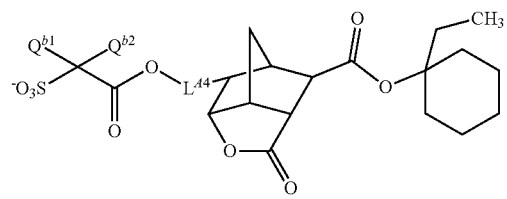
(B1-A-27)
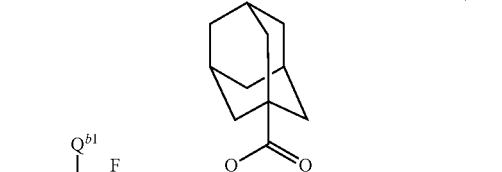
(B1-A-28)
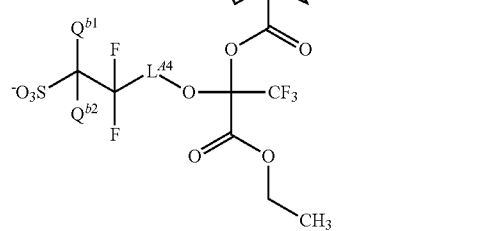
(B1-A-29)
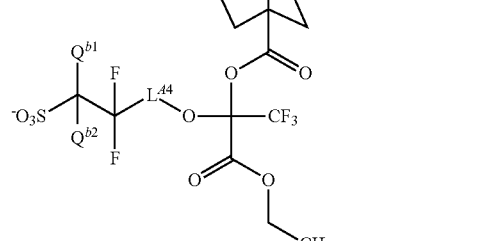
(B1-A-30)
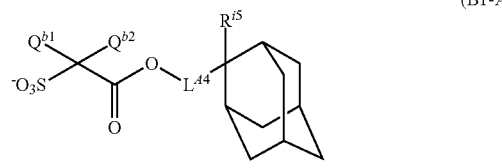
(B1-A-31)
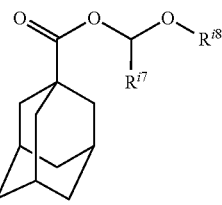
(B1-A-32)
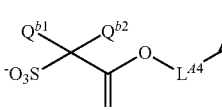
(B1-A-33)
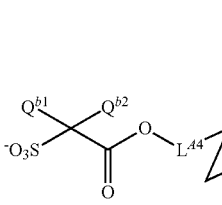
(B1-A-34)
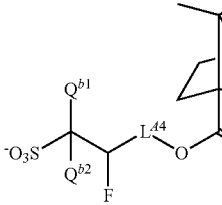
(B1-A-35)
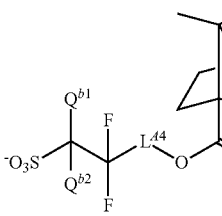
(B1-A-36)
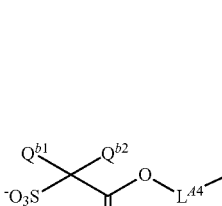
(B1-A-37)
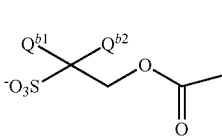
(B1-A-38)

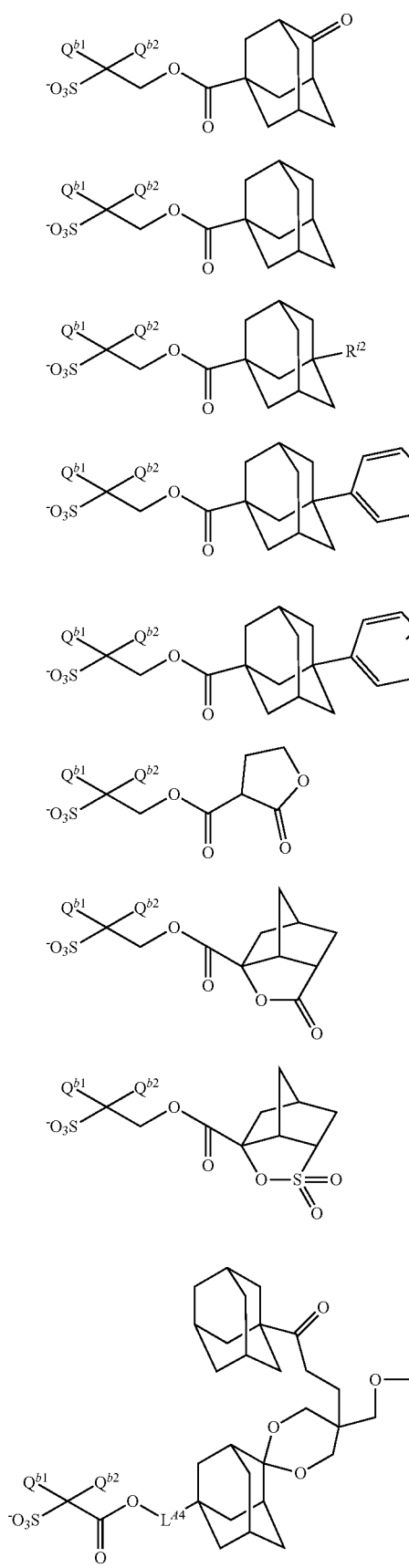
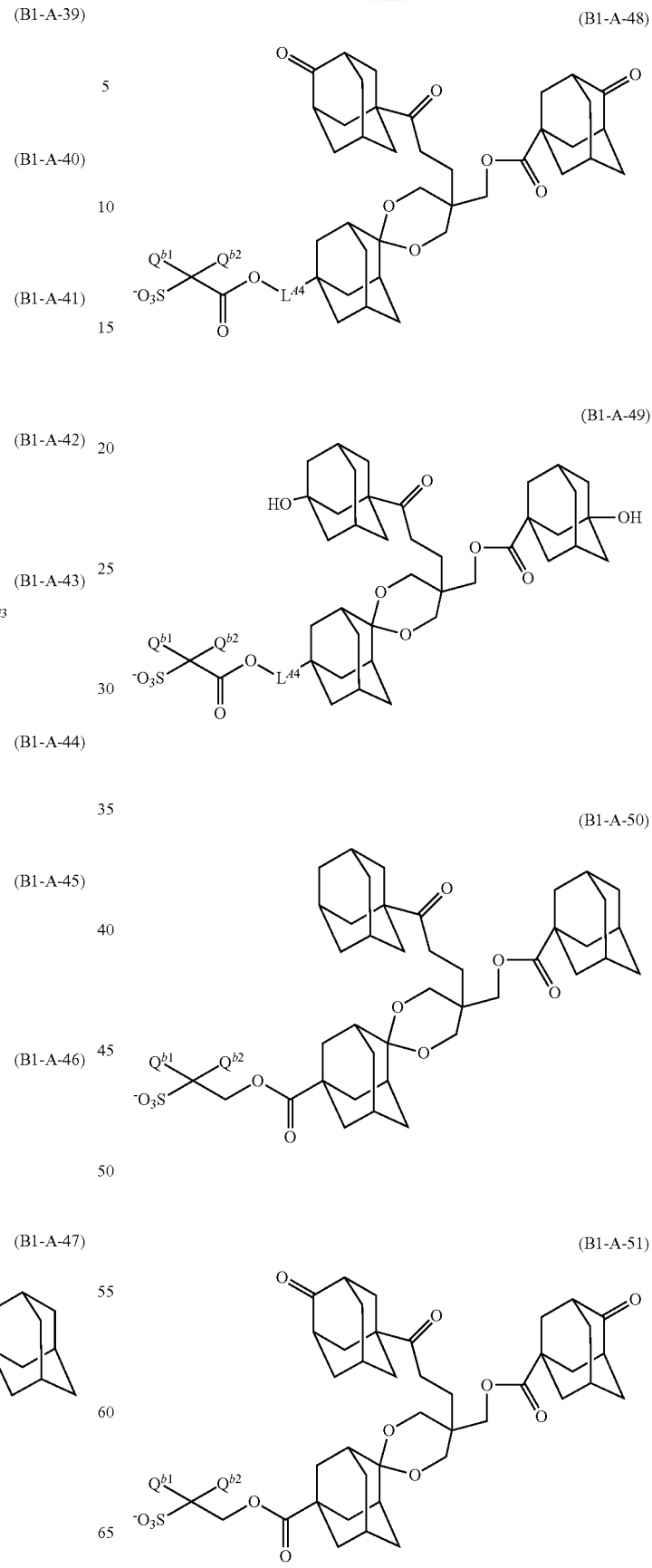

Specific examples of the sulfonic acid anion of the salt represented by formula (B1) include the following anions.

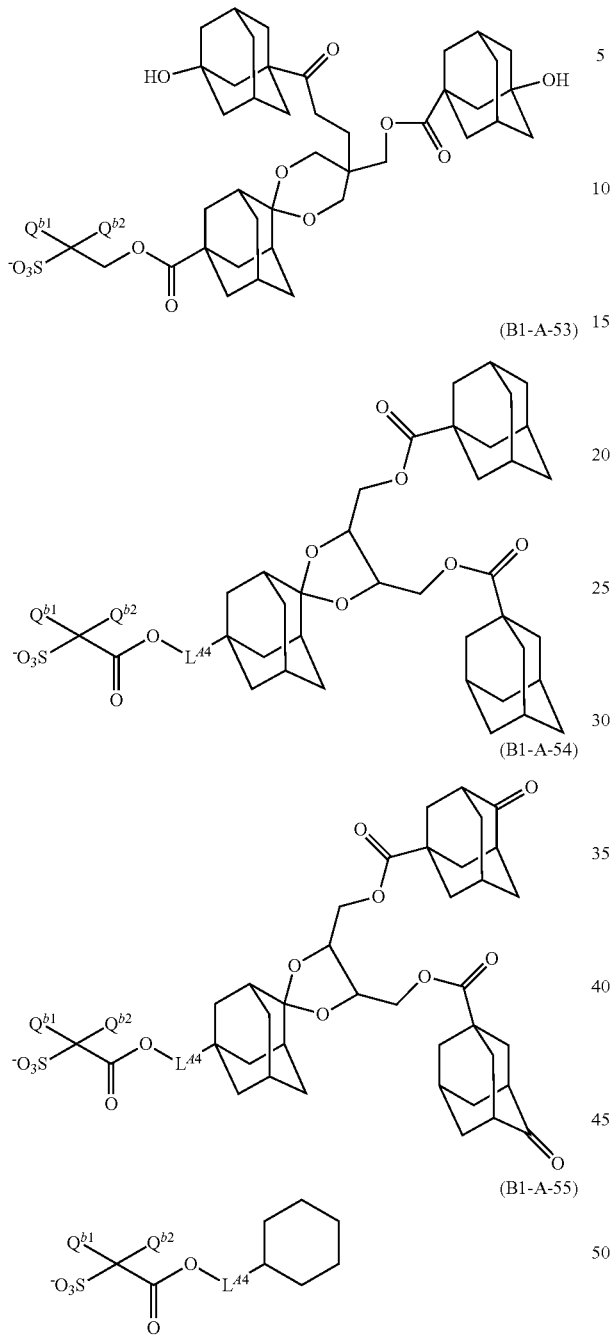

(B1a-1)

(B1a-2)

(B1a-3)

(B1a-4)

(B1a-5)

(B1a-6)

(B1a-7)

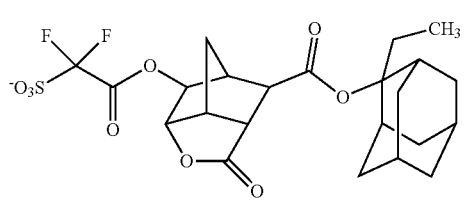
(B1a-8)

In these formulae, the symbols $Q^{b1}$ and $Q^{b2}$ are defined as above, $R^{i2}$, $R^{i3}$, $R^{i4}$, $R^{i5}$, $R^{i6}$ and $R^{i7}$ each independently represent a C1-C4 alkyl group, preferably a methyl group or an ethyl group, $R^{i8}$ represents a C1-C12 aliphatic hydrocarbon group [preferably a C1-C4 alkyl group], a C5-C12 monovalent alicyclic hydrocarbon group, or a combined group of them, preferably a methyl group, an ethyl group, a cyclohexyl group or an adamantyl group, and $L^{A4}$ represents a single bond or a C1-C4 alkanediyl group.

Examples of the sulfonic acid anion of the salt represented by formula (B1) include those described in JP2010-2046465A1.

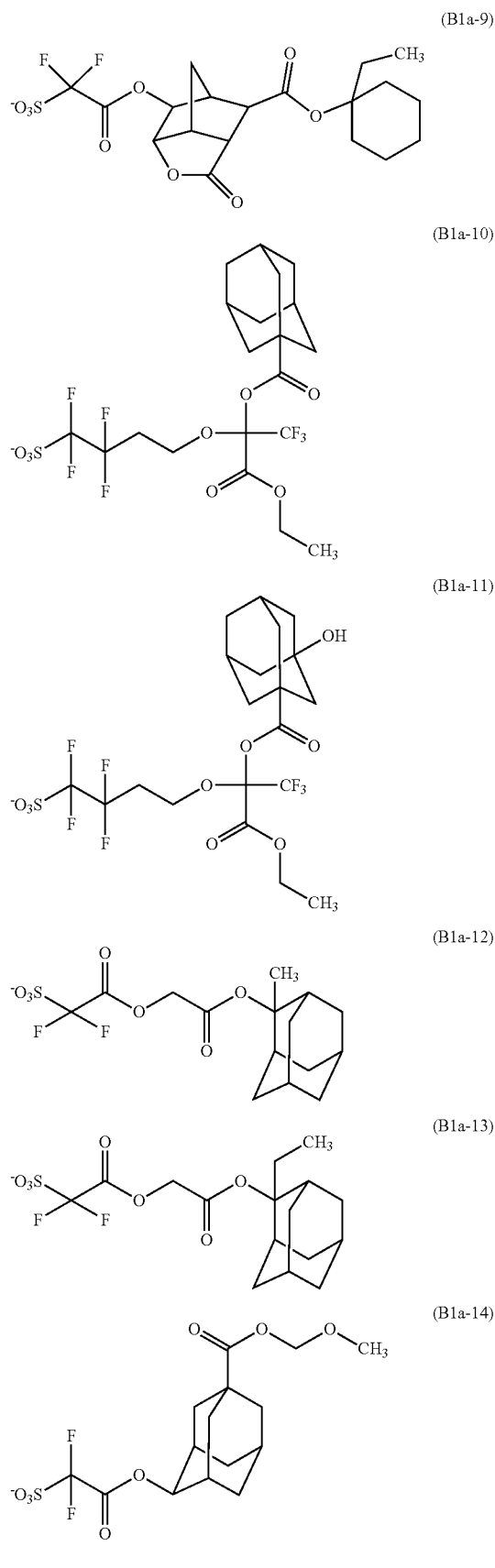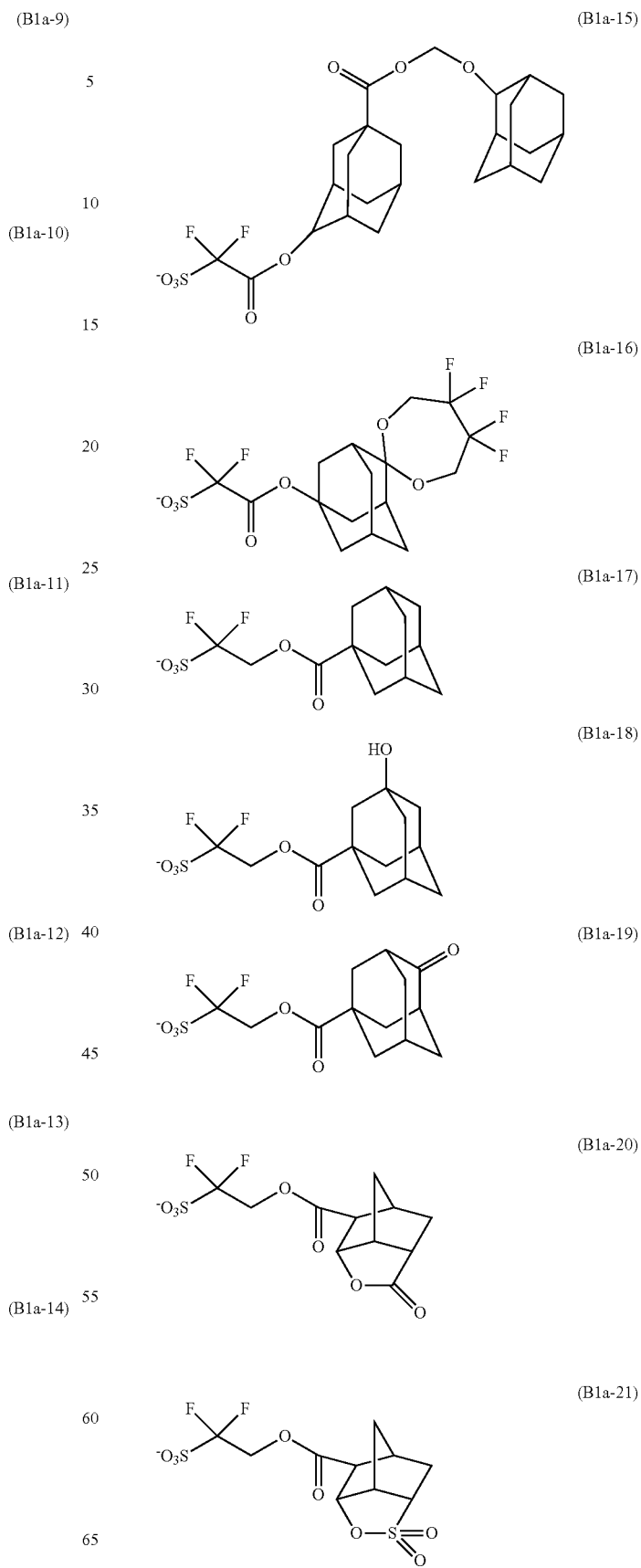

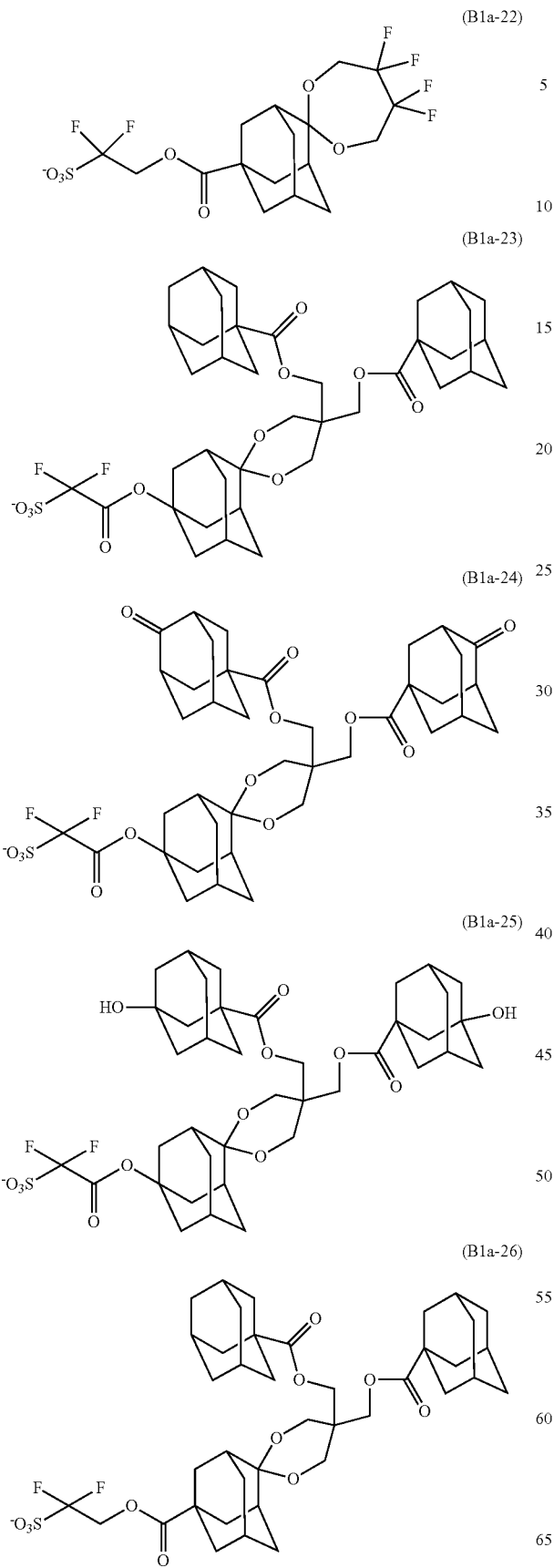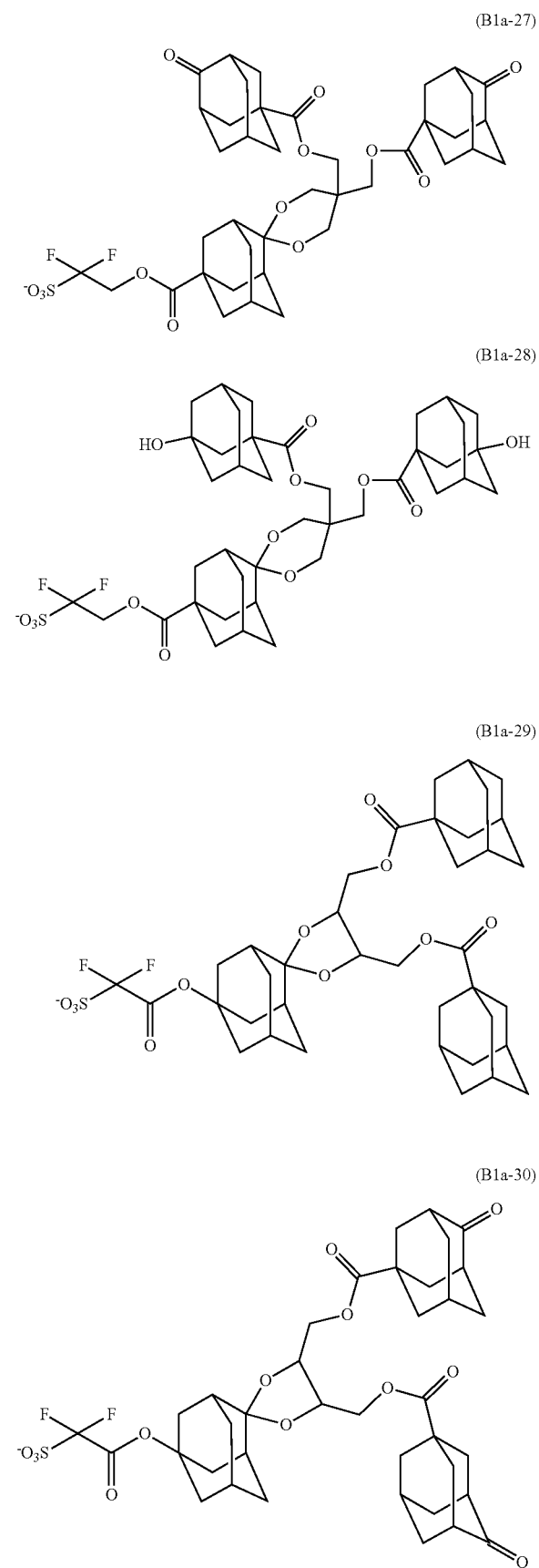

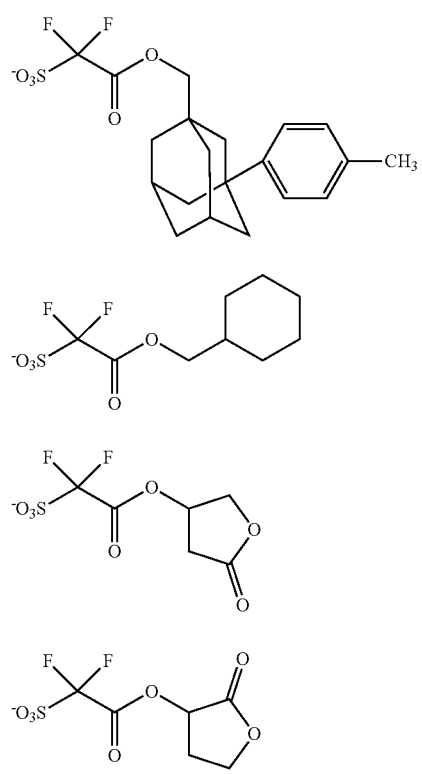

(B1a-31)
(B1a-32)
(B1a-33)
(B1a-34)

Among them, preferred are those represented by formulae (B1a-1) to (B1a-3), (B1a-7) to (B1a-16), (B1a-18), (B1a-19) and (B1a-22) to (B1a-30).

Examples of the organic counter ion represented by Z⁺ include an onium cation such as a sulfonium cation, an iodonium cation, an ammonium cation, a benzothiazolium cation and a phosphonium cation, and a sulfonium cation and an iodonium cation are preferred, and a sulfonium cation, specifically arylsulfonium cation, is more preferred.

Specific examples of the salt represented by formula (B1) include the following salts represented by formulae (B1-1) to (B1-48).

Among them, those which comprise an arylsulfonium cation are preferred, the salts represented by formulae (B1-1) to (B1-3), (B1-5) to (B1-7), (B1-11) to (B1-14), (B1-17), (B1-20) to (B1-26), (B1-29), (B1-31) to (B1-48) are more preferred.

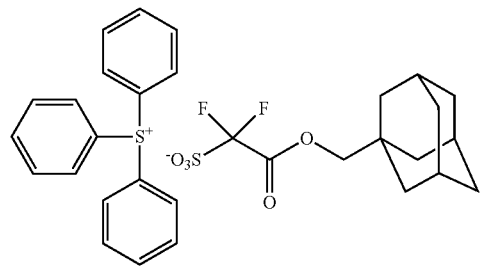

(B1-1)

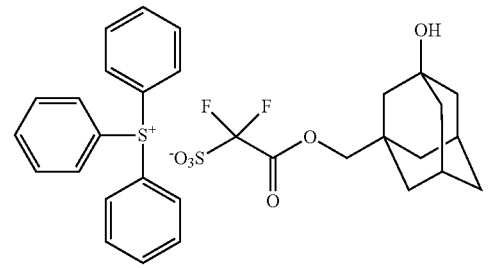

(B1-2)

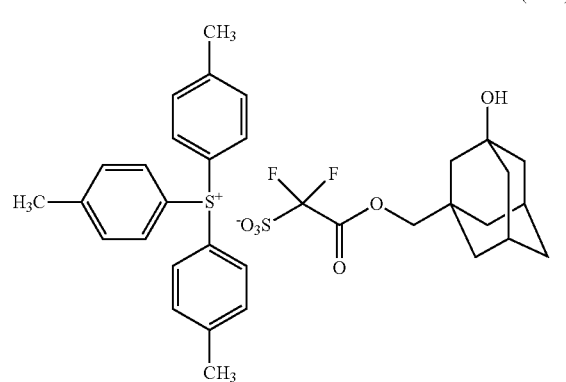

(B1-3)

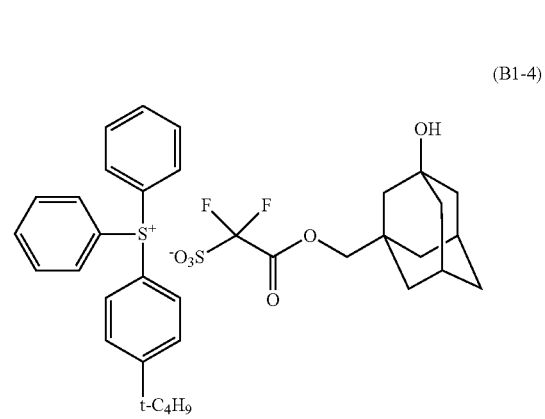

(B1-4)

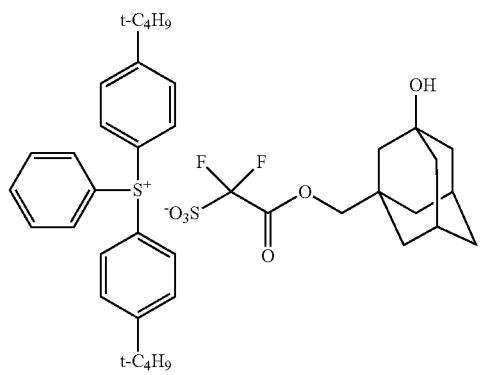

(B1-5)

(B1-6) 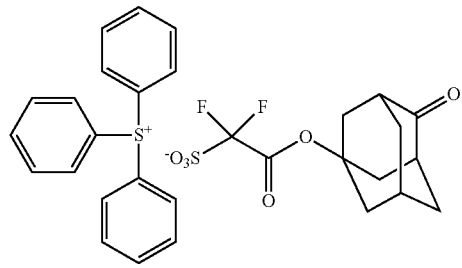
(B1-7) 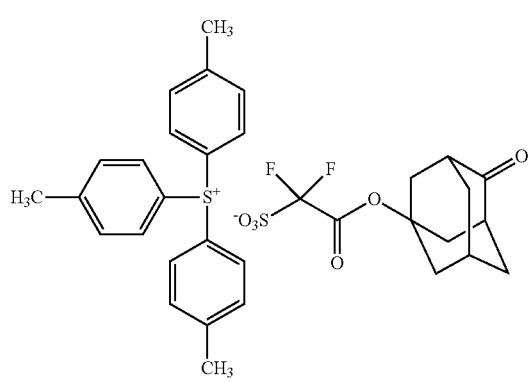
(B1-8) 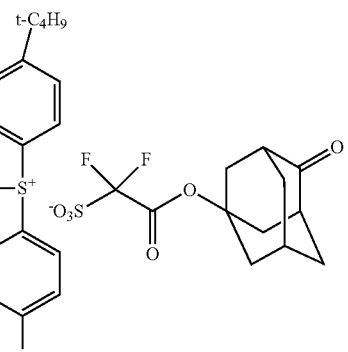
(B1-9) 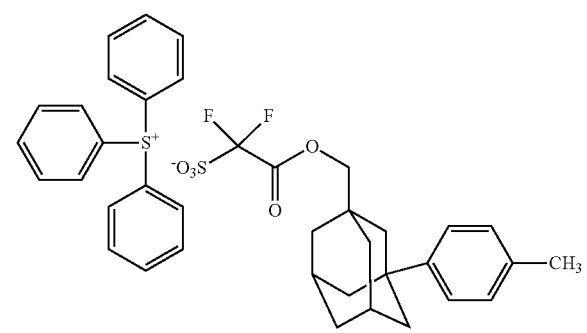
(B1-10) 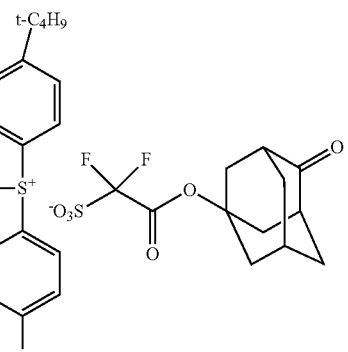
(B1-11) 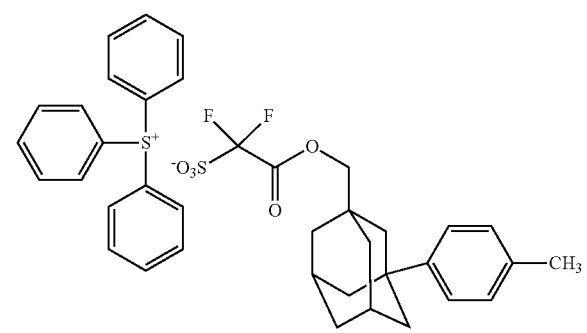
(B1-12) 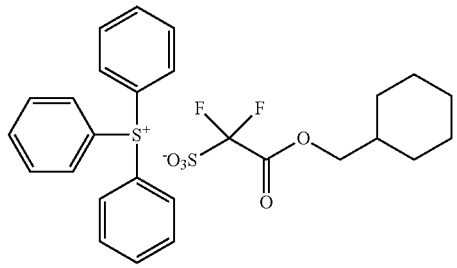
(B1-13) 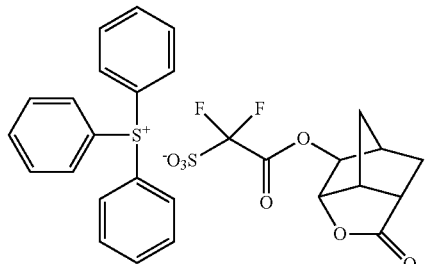
(B1-14) 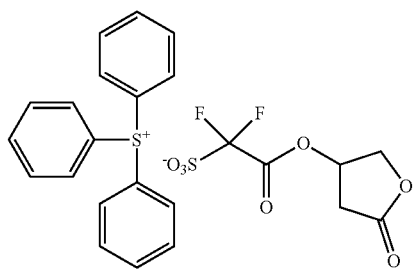

(B1-15)
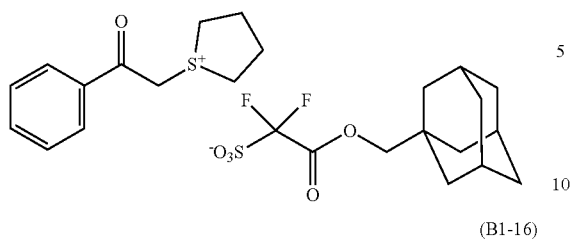
(B1-16)
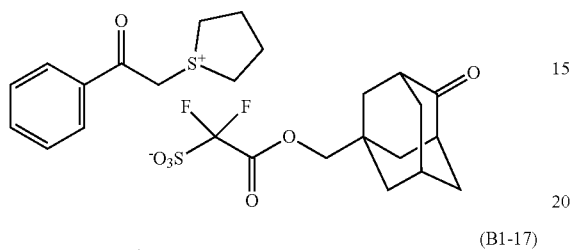
(B1-17)
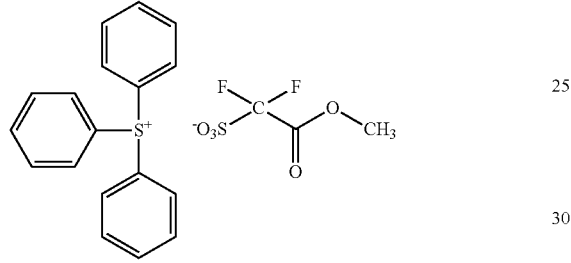
(B1-18)
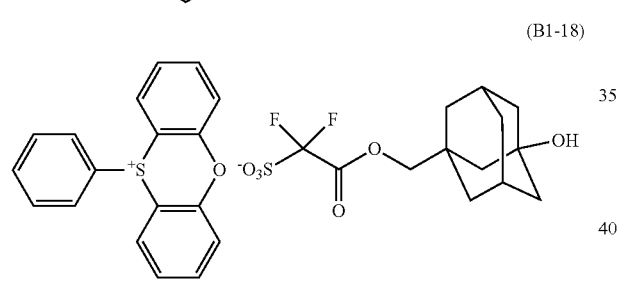
(B1-19)
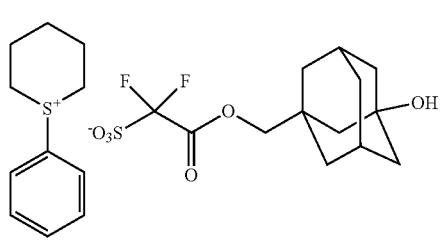
(B1-20)
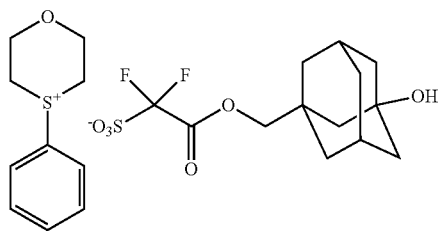
(B1-21)
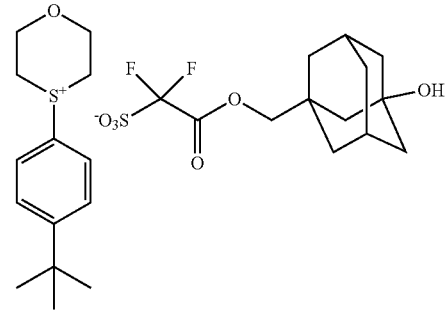
(B1-22)
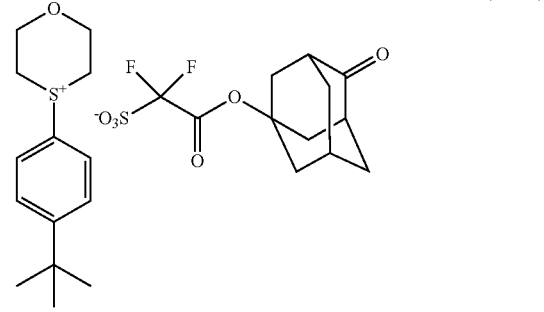
(B1-23)
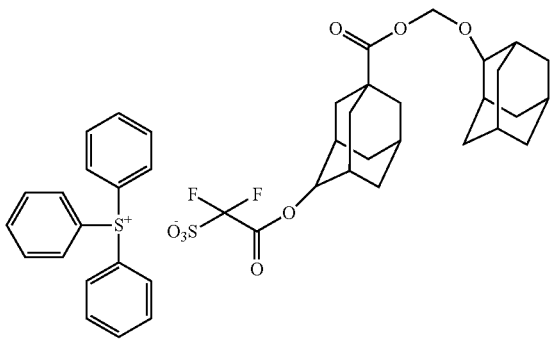
(B1-24)
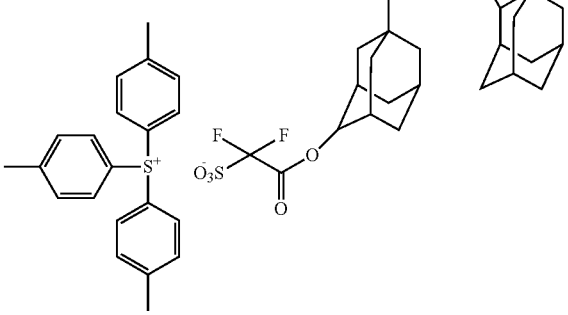
(B1-25)
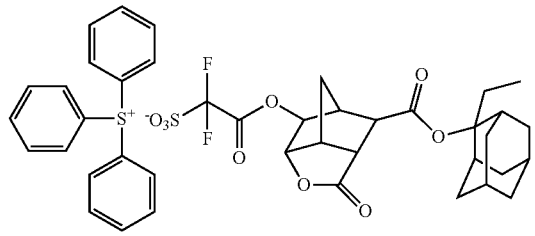

-continued
(B1-26)
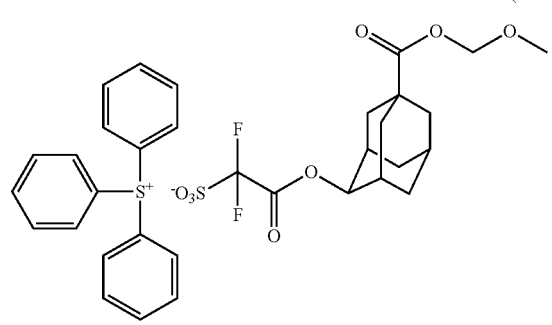
(B1-27)
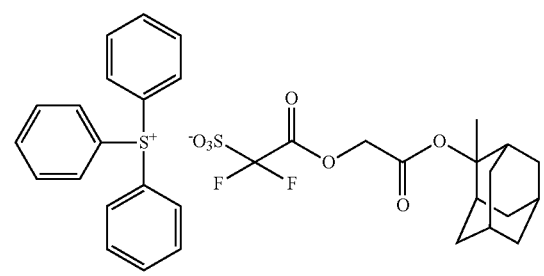
(B1-28)
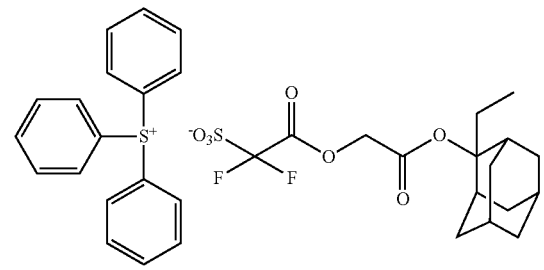
(B1-29)
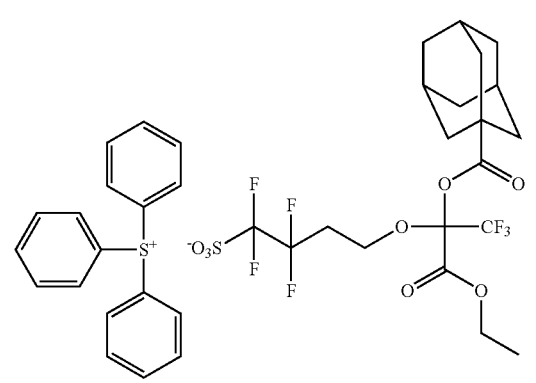
(B1-30)
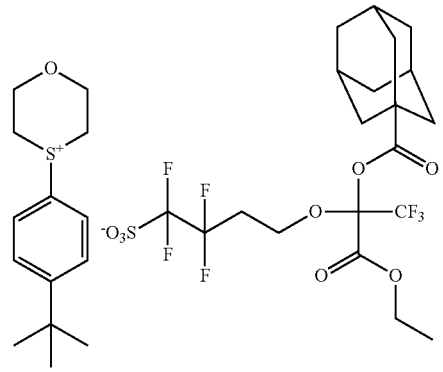
(B1-31)
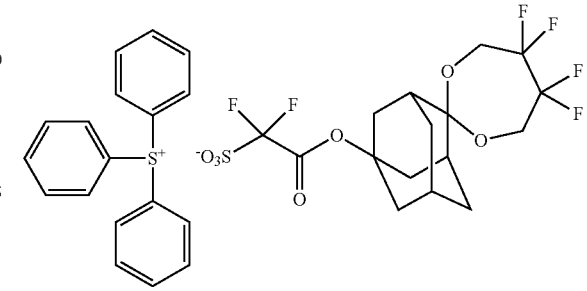
(B1-32)
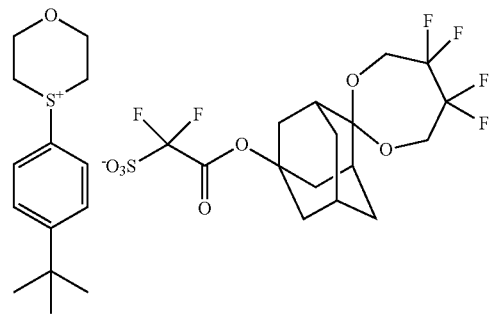
(B1-33)
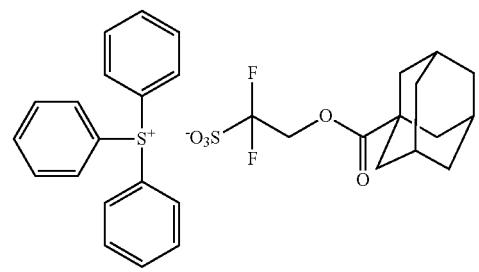
(B1-34)
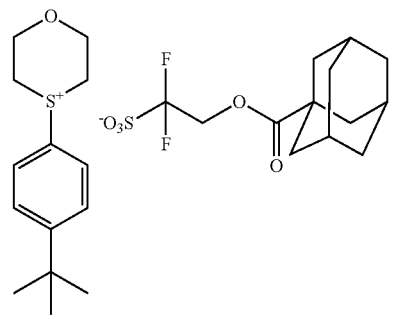

(B1-35)
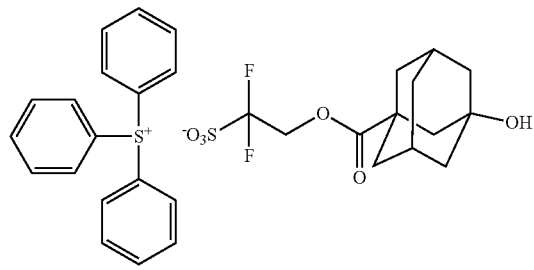
(B1-36)
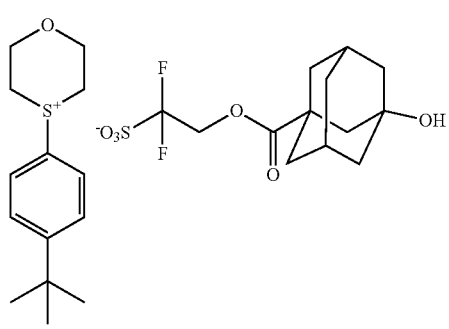
(B1-37)
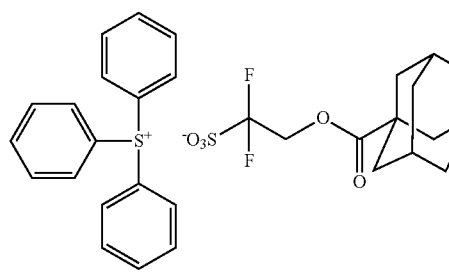
(B1-38)
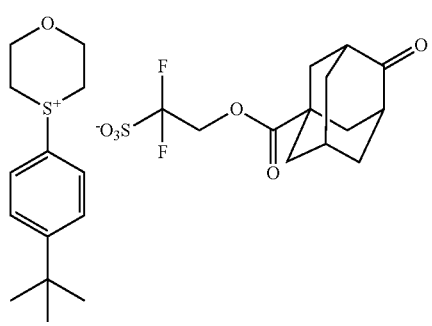
(B1-39)
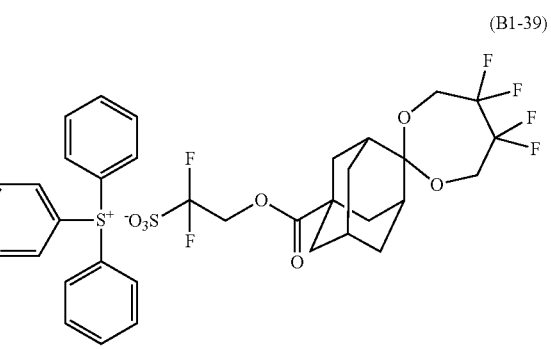
(B1-40)
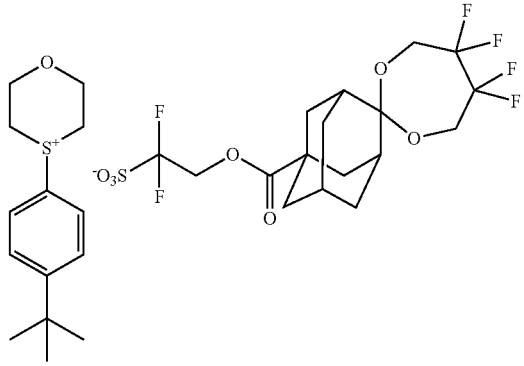
(B1-41)
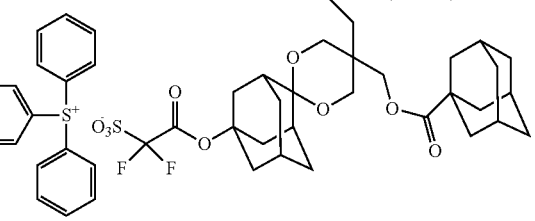
(B1-42)
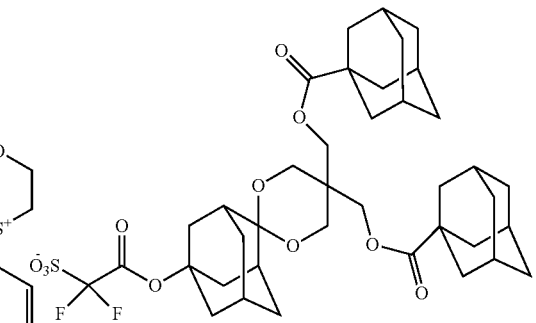
(B1-43)
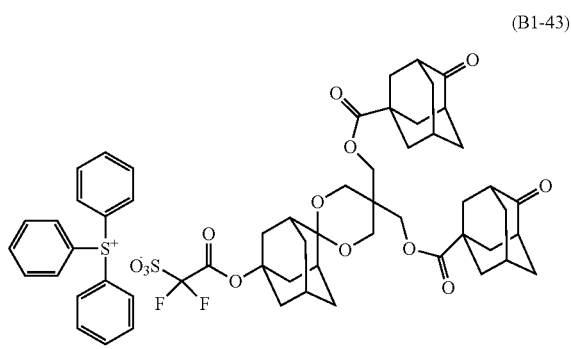

-continued (B1-44)
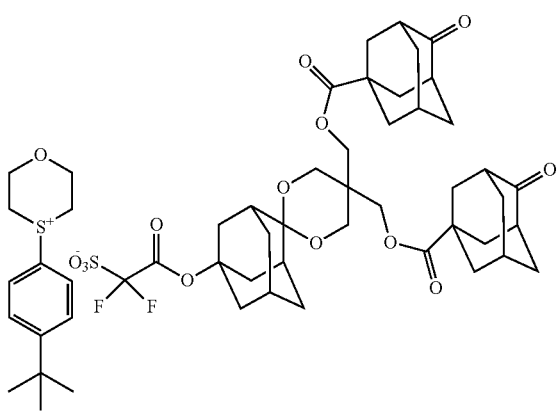

(B1-45)
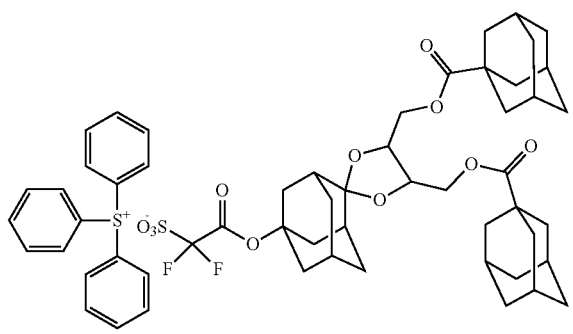

(B1-46)
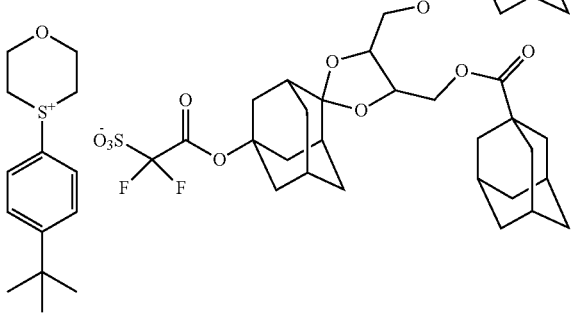

(B1-47)
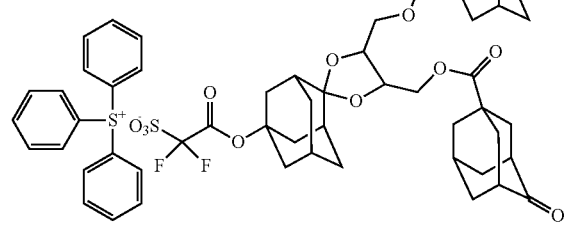

-continued (B1-48)
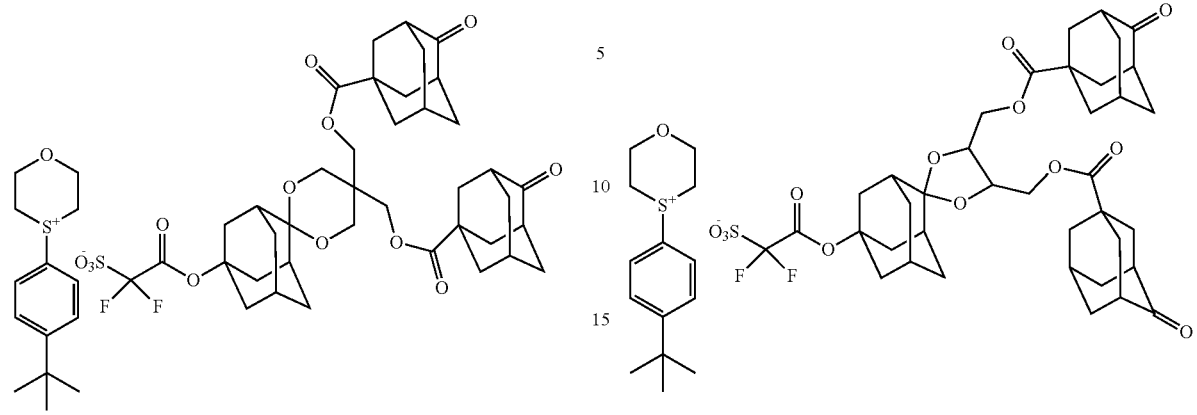

When the acid generator contains another salt than the salt (I), the weight ratio of salt (I) and the other salts is usually 1:99 to 99:1, preferably 2:98 to 98:2, more preferably 5:95 to 95:5, still more preferably 10:90 to 90:10, and further more preferably 15:85 to 85:15.

The photoresist composition of the disclosure comprises the acid generator containing the salt (I) and a resin having an acid-labile group which resin is referred to as "Resin (A)".

The photoresist composition may further contain anther salt than the salt (I) as an acid generator, a quencher, or solvent.

The content of the acid generator is preferably 1 to 40 parts by mass, more preferably 3 to 35 parts by mass, per 100 parts of Resin (A).

Resin (A) usually has a structural unit having an acid-labile group. Hereinafter, the structural unit is sometimes referred to as "structural unit (a1)".

Preferably Resin (A) further has another structural unit than the structural unit (a1), i.e. a structural unit having no acid-labile group, which is sometimes referred to as "structural unit(s)".

Herein, "an acid-labile group" means a group which has a hydrophilic group, such as a hydroxy group or a carboxy group, resulting from removing a leaving group therefrom by the action of an acid.

<Structural Unit (a1)>

The structural unit (a1) is derived from a compound having an acid-labile group which compound is sometimes referred to as "Monomer (a1)".

For Resin (A), the acid-labile groups represented by formulae (1) and (2) are preferred.

(1)
$$*-\left(\underset{\text{O}}{\overset{\text{O}}{\underset{\|}{C}}}-O\right)_{na}-\underset{R^{a3}}{\overset{R^{a1}}{\underset{|}{C}}}-R^{a2}$$

In formula (1), $R^{a1}$, $R^{a2}$ and $R^{a3}$ independently each represent a C1-C8 alkyl group, a C3-C20 alicyclic hydrocarbon group or a group consisting of them, and $R^{a1}$ and $R^{a2}$ can be bonded each other to form a C3-C20 alicyclic hydrocarbon group together with the carbon atom to which $R^{a1}$ and $R^{a2}$ are bonded, na represents an integer of 0 or 1, and * represents a binding position.

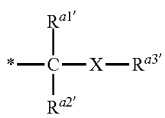

(2)

In formula (2), $R^{a1'}$ and $R^{a2'}$ independently each represent a hydrogen atom or a C1-C12 hydrocarbon group, and $R^{a3'}$ represents a C1-C20 hydrocarbon group, and $R^{a2'}$ and $R^{a3'}$ can be bonded each other to form a C3-C20 heterocyclic group together with X and the carbon atom to which $R^{a1}$ and $R^{a2}$ are bonded, and one or more —$CH_2$— in the hydrocarbon group and the heterocyclic group can be replaced by —O— or —S—, X represents an oxygen atom or a sulfur atom, and * represents a binding position.

For $R^{a1}$, $R^{a2}$ and $R^{a3}$, specific examples of the alkyl group include a methyl group, an ethyl group, a propyl group, an isopropyl group, a butyl group, a pentyl group, a hexyl group, a heptyl group and an octyl group.

The alicyclic hydrocarbon group may be monocyclic or polycyclic. Examples of the alicyclic hydrocarbon group include a monocyclic alicyclic hydrocarbon group such as a C3-C20 cycloalkyl group (e.g. a cyclopentyl group, a cyclohexyl group, a cycloheptyl group and a cyclooctyl group) and a polycyclic alicyclic hydrocarbon group such as a decahydronaphthyl group, an adamantyl group, a norbornyl group, and the followings:

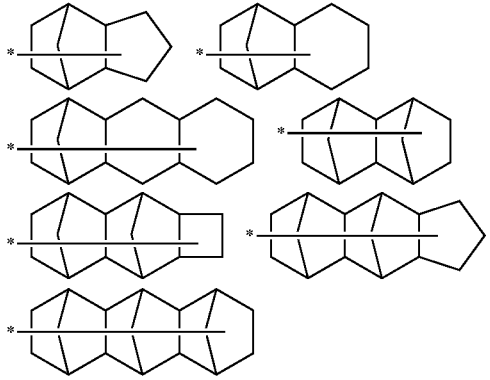

in which * represents a binding position.

The alicyclic hydrocarbon group preferably has 3 to 16 carbon atoms.

Examples of the group consisting of alkyl and alicyclic hydrocarbon group include a methylcyclohexyl group, a dimethylcyclohexyl group, a methylnorbornyl group, an adamantylmethyl group, and a norbornylethyl group.

The "na" is preferably 0.

When the divalent hydrocarbon group is formed by bonding $R^{a1}$ and $R^{a2}$ each other, examples of the moiety —$C(R^{a1})(R^{a2})(R^{a3})$— include the following groups and the divalent hydrocarbon group preferably has 3 to 16 carbon atoms.

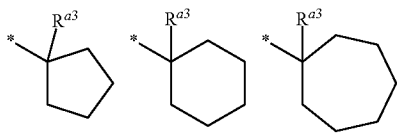

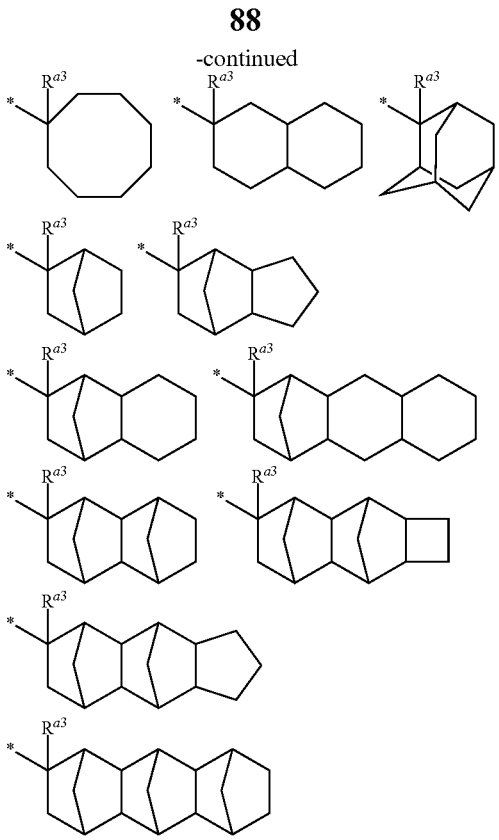

wherein $R^{a3}$ is the same as defined above and * represents a binding position.

The group represented by formula (1) wherein $R^{a1}$, $R^{a2}$ and $R^{a3}$ independently each represent a C1-C8 alkyl group such as a tert-butyl group, the group represented by formula (1) wherein $R^{a1}$ and $R^{a2}$ are bonded each other to form an adamantyl ring and $R^{a3}$ is a C1-C8 alkyl group such as a 2-alkyl-2-adamantyl group, and the group represented by formula (1) wherein $R^{a1}$ and $R^{a2}$ are C1-C8 alkyl groups and $R^{a3}$ is an adamantyl group such as a 1-(1-adamantyl)-1-alkylalkoxycarbonyl group are preferred.

For formula (2), examples of the hydrocarbon group include an alkyl group, an alicyclic hydrocarbon group, an aromatic hydrocarbon group and a group consisting of two or more of them.

Examples of the aliphatic hydrocarbon group and the alicyclic hydrocarbon group include the same as described above. Examples of the aromatic hydrocarbon group include an aryl group such as a phenyl group, a naphthyl group, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

Examples of the heterocyclic group formed by bonding $R^{a2'}$ and $R^{a3'}$ together with X and the carbon atom to which $R^{a2'}$ and $R^{a3'}$ are bonded include the following ones.

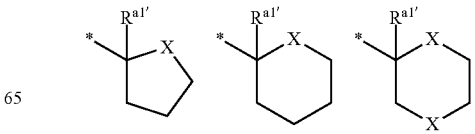

-continued
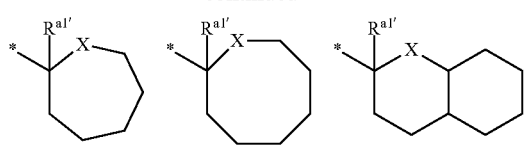
wherein * represents a binding position.
In formula (2), at least one of $R^{a1'}$ and $R^{a2'}$ is preferably a hydrogen atom.
Specific examples of the group represented by formula (1) include the following.
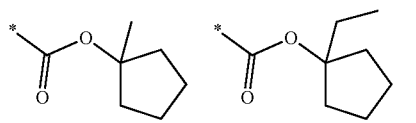
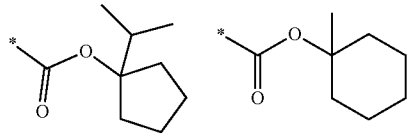
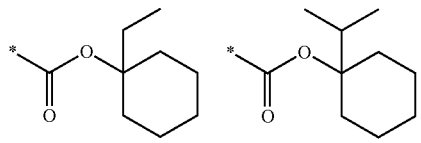
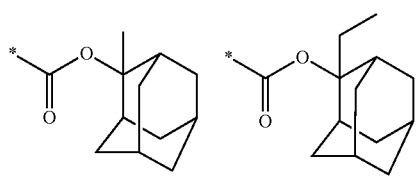
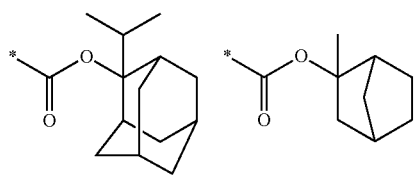
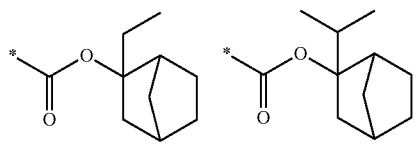
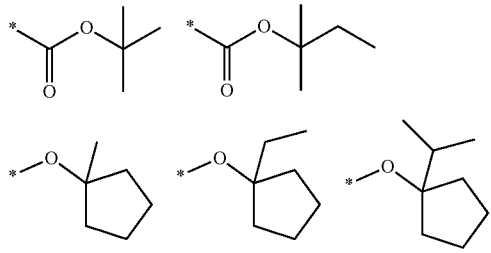
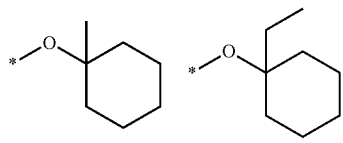
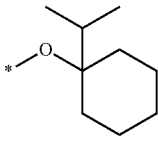
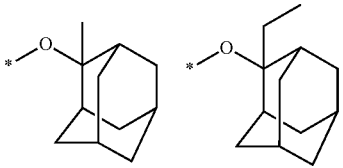
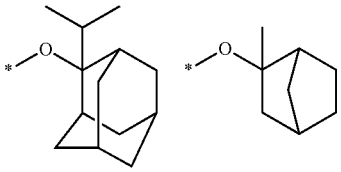
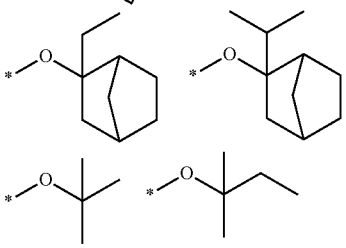
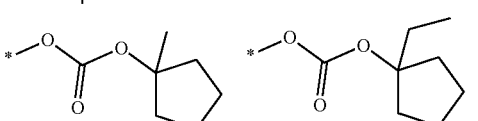
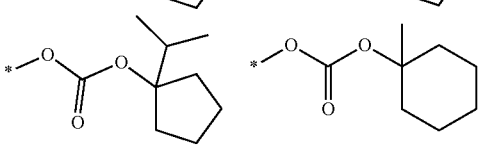
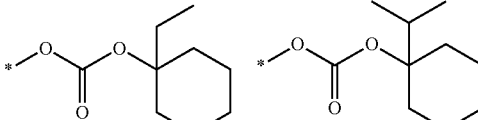
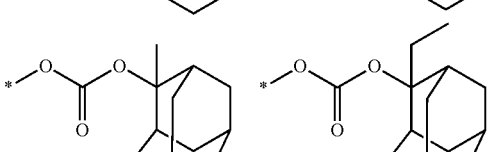
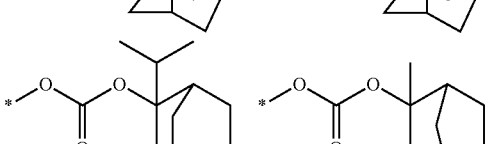
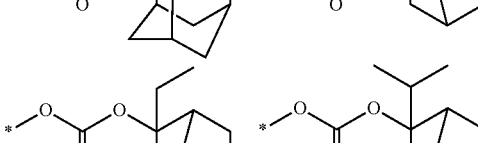
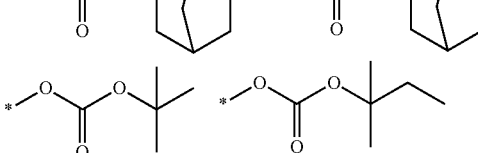

Specific examples of the group represented by formula (2) include the following.

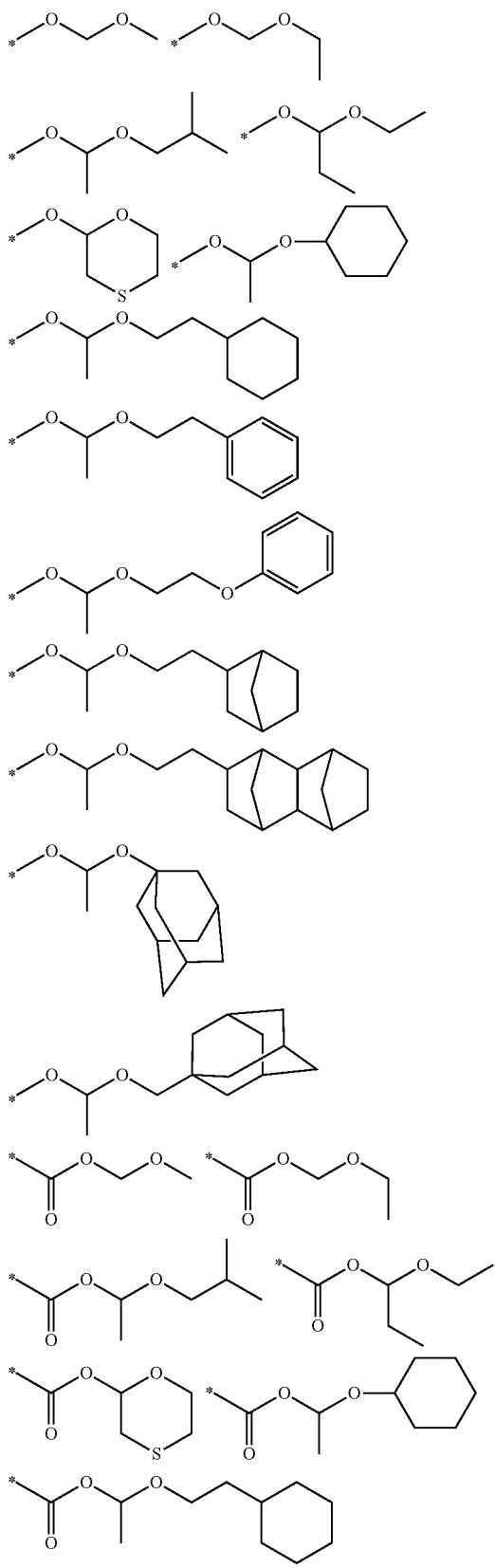

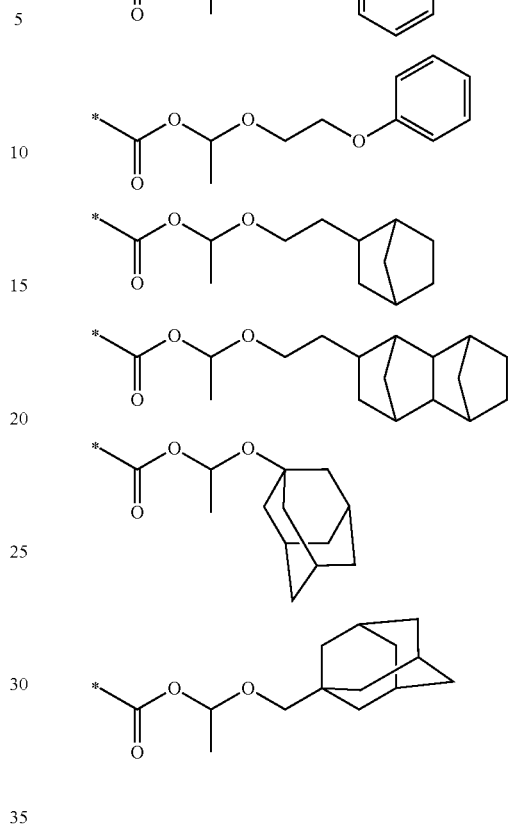

Monomer (a1) is preferably a monomer having an acid-labile group in its side chain and an ethylenic unsaturated group, more preferably a (meth)acrylate monomer having an acid-labile group in its side chain, and still more preferably a (meth)acrylate monomer having the group represented by formula (1) or (2).

The (meth)acrylate monomer having an acid-labile group in its side chain is preferably those which comprise a C5-C20 alicyclic hydrocarbon group. The resin which comprises a structural unit derived from such monomers can provide improved resolution for a photoresist pattern to be prepared therefrom.

The structural unit derived from a (meth)acrylate monomer having the group represented by formula (1) is preferably one of structural units represented by formulae (a1-0), (a1-1) and (a1-2).

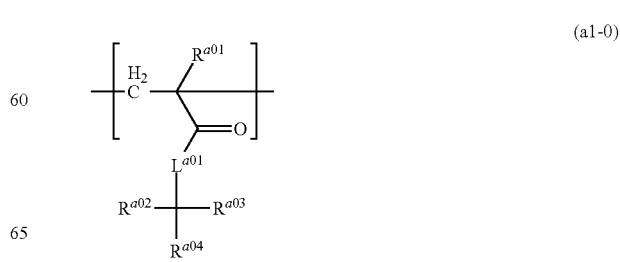

(a1-0)

-continued

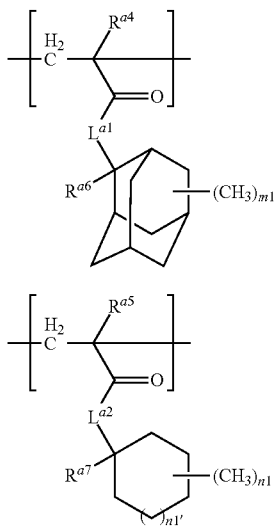

(a1-1)

(a1-2)

In each formula, $L^{a01}$, $L^{a1}$ and $L^{a2}$ each independently represent —O— or *—O—$(CH_2)_{k1}$—CO—O— in which k1 represents an integer of 1 to 7 and * represents a binding position to —CO—, $R^{a01}$, $R^{a4}$ and $R^{a5}$ each independently represent a hydrogen atom or a methyl group, $R^{a02}$, $R^{a03}$, $R^{a04}$, $R^{a6}$ and $R^{a7}$ each independently represent a C1-C8 alkyl group, a C3-C18 alicyclic hydrocarbon group, or a group formed by combining them, m1 represents an integer of 0 to 14, n1 represents an integer of 0 to 10, and n1' represents an integer of 0 to 3.

Hereinafter, the structural units represented by formulae (a1-0), (a1-1) and (a1-2) are respectively referred to as "structural unit (a1-0)", "structural unit (a1-1)" and "structural unit (a1-2)".

Resin (A) may comprise two or more of such structural units.

$L^{a01}$ is preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably *—O—.

$R^{a01}$ is preferably a methyl group.

For $R^{a02}$, $R^{a03}$ and $R^{a04}$, examples of the alkyl group, the alicyclic hydrocarbon group and the group formed by combining them include the same as referred for $R^{a1}$, $R^{a2}$ and $R^{a3}$.

The alkyl group preferably has 1 to 6 carbon atoms.

The alicyclic hydrocarbon group preferably has 3 to 8 carbon atoms and more preferably 3 to 6 carbon atoms. The alicyclic hydrocarbon group is preferably a saturated aliphatic cyclic hydrocarbon group.

The group formed by combining them preferably has 18 carbon atoms or less in total, examples of which include a methylcyclohexyl group, a dimethylcyclohexyl group, and a methylnorbornyl group.

Each of $R^{a02}$ and $R^{a03}$ is preferably a C1-C6 alkyl group, more preferably a methyl group and an ethyl group.

$R^{a04}$ is preferably a C1-C6 alkyl group and a C5-C12 alicyclic hydrocarbon group, more preferably a methyl group, an ethyl group, a cyclohexyl group, and an adamantyl group.

Each of $L^{a1}$ and $L^{a2}$ is preferably *—O— or *—O—$(CH_2)_{f1}$—CO—O— in which * represents a binding position to —CO—, and f1 is the same as defined above, and is more preferably *—O— or *—O—$CH_2$—CO—O—, and is especially preferably *—O—.

Each of $R^{a4}$ and $R^{a5}$ is preferably a methyl group.

For $R^{a6}$ and $R^{a7}$, examples of the alkyl group include a methyl group, an ethyl group, a propyl group, an isopropyl group, a butyl group, a tert-butyl group, a pentyl group, a heptyl group, a 2-ethylheptyl group and an octyl group.

For $R^{a6}$ and $R^{a7}$, examples of the alicyclic hydrocarbon group include a monocyclic alicyclic hydrocarbon group such as a cyclohexyl group, a methylcyclohexyl group, a dimethylcyclohexyl group, a cycloheptyl group and a methylcycloheptyl group, and a polycyclic alicyclic hydrocarbon group such as a decahydronaphthyl group, an adamantyl group, a norbornyl group, a methylnorbornyl group and the following.

For $R^{a6}$ and $R^{a7}$, examples of the group consisting of an alkyl group and an alicyclic hydrocarbon group include an aralkyl group such as a benzyl group, and a phenethyl group.

The alkyl group represented by $R^{a6}$ and $R^{a7}$ is preferably a C1-C6 alkyl group.

The alicyclic hydrocarbon group represented by $R^{a6}$ and $R^{a7}$ is preferably a C3-C8 alicyclic hydrocarbon group, more preferably a C3-C6 alicyclic hydrocarbon group.

The "m1" is preferably an integer of 0 to 3, and is more preferably 0 or 1.

The "n1" is preferably an integer of 0 to 3, and is more preferably 0 or 1.

The "n1'" is preferably 0 or 1.

Examples of the structural unit (a1-0) include those represented by formulae (a1-0-1) to (a1-0-12), preferably those represented by formulae (a1-0-1) to (a1-0-10).

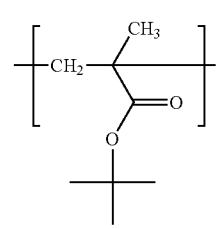

(a1-0-1)

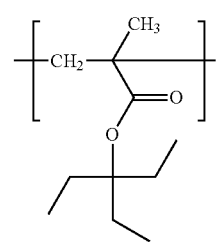

(a1-0-2)

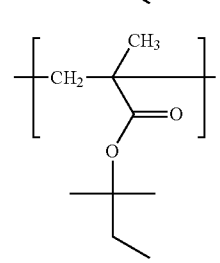

(a1-0-3)

(a1-0-4) 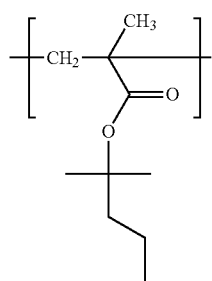

(a1-0-5) 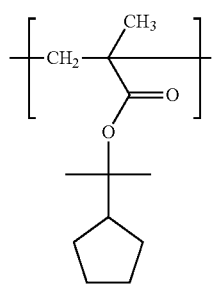

(a1-0-6) 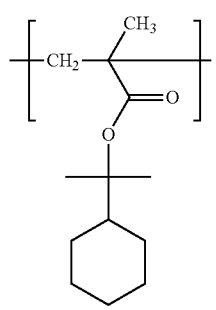

(a1-0-7) 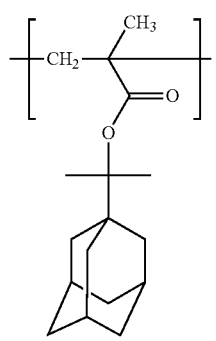

(a1-0-8) 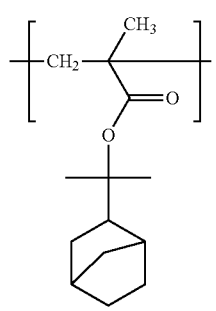

(a1-0-9) 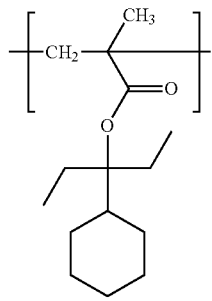

(a1-0-10) 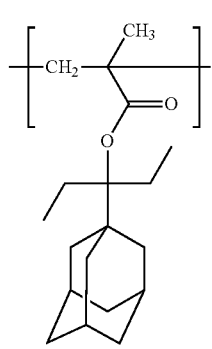

(a1-0-11) 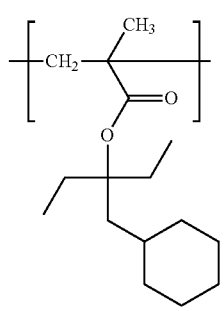

(a1-0-12) 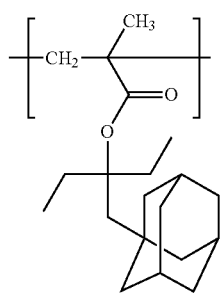

Examples of the structural unit (a1-0) further include such groups that a methyl group has been replaced by a hydrogen atom in any one of formulae (a1-0-1) to (a1-0-12).

Examples of the monomer from which the structural unit (a1-1) is derived include the monomers described in JP2010-204646A1, and the following monomers represented by the formulae (a1-1-1) to (a1-1-4) and such groups that a methyl group has been replaced by a hydrogen atom in any one of formulae (a1-1-1) to (a1-1-4), preferably the following monomers represented by the formulae (a1-1-1) to (a1-1-4).

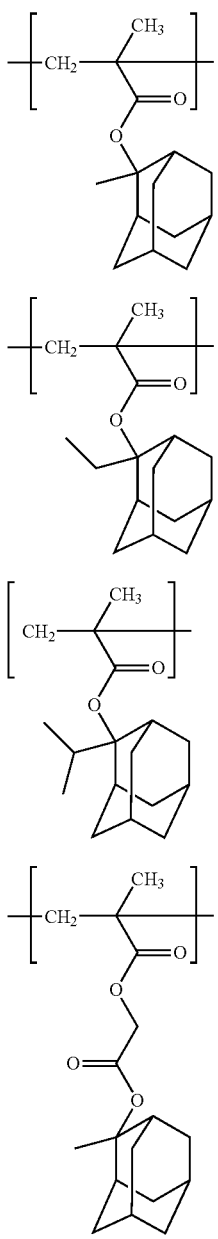

(a1-1-1)

(a1-1-2)

(a1-1-3)

(a1-1-4)

Examples of the monomer from which the structural unit (a1-2) is derived include 1-ethylcyclopentan-1-yl acrylate, 1-ethylcyclopentan-1-yl methacrylate, 1-ethylcyclohexan-1-yl acrylate, 1-ethylcyclohexan-1-yl methacrylate, 1-ethylcycloheptan-1-yl acrylate, 1-ethylcycloheptan-1-yl methacrylate, 1-methylcyclopentan-1-yl acrylate, 1-methylcyclopentan-1-yl methacrylate, 1-isopropylcyclopentan-1-yl acrylate and 1-isopropylcyclopentan-1-yl methacrylate, preferably the monomers represented by formulae (a1-2-1) to (a1-2-6) and those represented by the formulae in which a methyl group corresponding to $R^5$ has been replaced by a hydrogen atom, more preferably the monomers represented by formulae (a1-2-2), (a1-2-5) and (a1-2-6).

When the resin comprises one or more of the structural units represented by formulae (a1-0), (a1-1) and (a1-2), the total content of the structural units is usually 10 to 95% by mole, preferably 15 to 90% by mole and more preferably 15 to 90% by mole, still more preferably 20 to 85% by mole, further more preferably 25 to 70% by mole, and still further more preferably 30 to 65% by mole, based on 100% by mole of all the structural units of the resin.

Examples of the structural unit (a1) having the group represented by formula (2) include a structural unit represented by formula (a1-4). The structural unit is sometimes referred to as "structural unit (a1-4)".

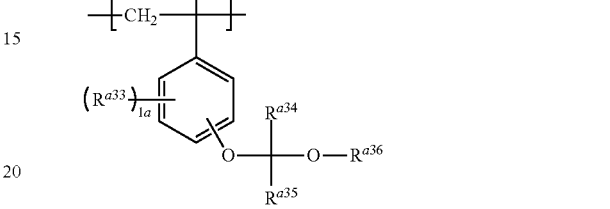

(a1-4)

In the formula, $R^{a32}$ represents a hydrogen atom, a halogen atom or a C1-C6 alkyl group that may have a halogen atom, $R^{a33}$ in each occurrence independently represent a halogen atom, a hydroxy group, a C1-C6 alkyl group, a C1-C6 alkoxy group, a C2-C4 acyl group, a C2-C4 acyloxy group, an acryloyloxy group or methacryloyloxy group, "1a" represents an integer 0 to 4, $R^{a34}$ and $R^{a35}$ each independently represent a hydrogen atom or a C1-C12 hydrocarbon group; and $R^{a36}$ represents a C1-C20 hydrocarbon group, or $R^{a35}$ and $R^{a36}$ may be bonded together with a C—O bonded thereto to form a divalent C3-C20 heterocyclic group, and a methylene group contained in the hydrocarbon group or the divalent heterocyclic group may be replaced by an oxygen atom or a sulfur atom.

Examples of the alkyl group of $R^{a32}$ and $R^{a33}$ include methyl, ethyl, propyl, isopropyl, butyl, pentyl and hexyl groups. The alkyl group is preferably a C1-C4 alkyl group, and more preferably a methyl group or an ethyl group, and still more preferably a methyl group.

Examples of the halogen atom of $R^{a32}$ and $R^{a33}$ include a fluorine, chlorine, bromine and iodine atoms.

Examples of the alkyl group that may have a halogen atom include trifluoromethyl, difluoromethyl, methyl, perfluoroethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, n-pentyl, n-hexyl and n-perfluorohexyl groups.

Examples of an alkoxy group include methoxy, ethoxy, propoxy, butoxy, pentyloxy and hexyloxy groups. The alkoxy group is preferably a C1-C4 alkoxy group, more preferably a methoxy group or an ethoxy group, and still more preferably a methoxy group.

Examples of the acyl group include acetyl, propionyl and butyryl groups. Examples of the acyloxy group include acetyloxy, propionyloxy and butyryloxy groups. Examples of the hydrocarbon group for $R^{a34}$ and $R^{a35}$ are the same examples as described in $R^{a1'}$ to $R^{a2'}$ in the formula (2).

Examples of hydrocarbon group for $R^{a36}$ include a C1-C18 alkyl group, a C3-C18 alicyclic hydrocarbon group, a C6-C18 aromatic hydrocarbon group or a group formed by combining thereof.

In the formula (a1-4), $R^{a32}$ is preferably a hydrogen atom.

$R^{a33}$ is preferably a C1-C4 alkoxy group, more preferably a methoxy group or an ethoxy group, and still more preferably a methoxy group.

"1a" is preferably 0 or 1, and more preferably 0. $R^{a34}$ is preferably a hydrogen atom. $R^{a35}$ is preferably a C1-C12 hydrocarbon group, and more preferably a methyl group or an ethyl group.

The hydrocarbon group for $R^{a36}$ is preferably a C1-C18 alkyl group, a C3-C18 alicyclic hydrocarbon group, a C6-C18 aromatic hydrocarbon group or a combination thereof, and more preferably a C1-C18 alkyl group, a C3-C18 alicyclic hydrocarbon group or a C7-C18 aralkyl group. The alkyl group and the alicyclic hydrocarbon group for $R^{a36}$ are preferably unsubstituted. When the aromatic hydrocarbon group of $R^{a36}$ has a substituent, the substituent is preferably a C6-C10 aryloxy group.

Examples of the structural unit (a1-4) include those derived from the monomers described in JP2010-204646A1. Among them, the structural unit is preferably the following ones represented by formula (a1-4-1) to formula (a1-4-8), and more preferably the structural units represented by formula (a1-4-1) to formula (a1-4-5).

(a1-4-1)

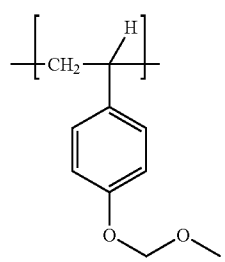

(a1-4-2)

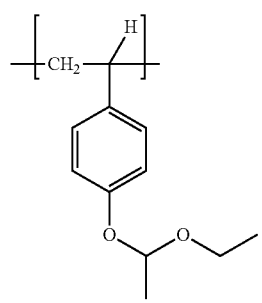

(a1-4-3)

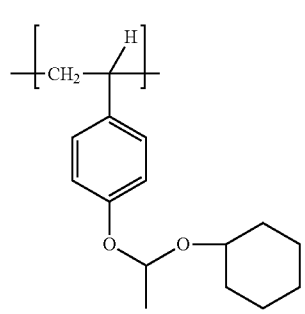

(a1-4-4)

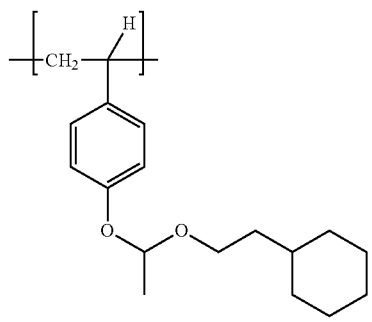

(a1-4-5)

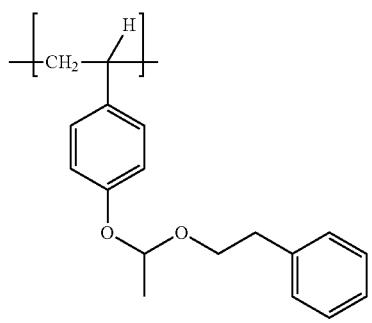

(a1-4-6)

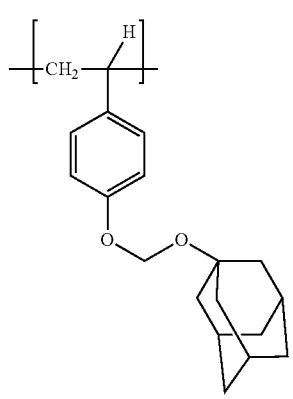

(a1-4-7)

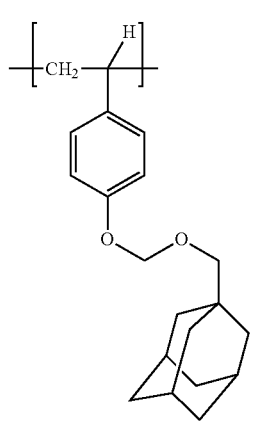

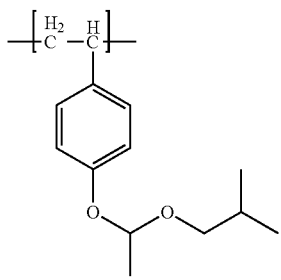
(a1-4-8)

When the resin (A) has the structural unit (a1-4), the proportion thereof is preferably 10% by mole to 95% by mole, more preferably 15% by mole to 90% by mole, still more preferably 20% by mole to 85% by mole, further more preferably 20% by mole to 70% by mole, and still furthermore preferably 20% by mole to 60% by mole, based on the all the structural units of the resin (A) (100% by mole) Examples of the structural unit having an acid-labile group represented by formula (2) include one represented by formula (a1-5)

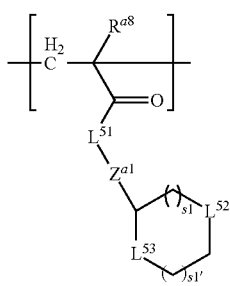
(a1-5)

In formula (a1-5), $R^{a8}$ represents a hydrogen atom, a halogen atom, or a C1-C6 alkyl group which may have a halogen atom,
$Z^{a1}$ represents a single bond or *—$(CH_2)_{h3}$—CO— $L^{54}$- in which h3 represents an integer of 1 to 4 and * represents a binding position to $L^{54}$,
$L^{51}$, $L^{52}$, $L^{53}$ and $L^{54}$ each independently represent an oxygen atom or a sulfur atom,
s1 represents an integer of 1 to 3, and s1' represents an integer of 0 to 3.

Herein, the structural unit represented by formula (a1-5) is sometimes referred to as "structural unit (a1-5)".

Examples of halogen atoms include a fluorine atom and chlorine atom, preferably a fluorine atom.

Examples of the alkyl group which may have a halogen atom include a methyl group, an ethyl group, n-propyl group, an isopropyl group, n-butyl group, sec-butyl group, tert-butyl group, a pentyl group, a hexyl group, a heptyl group, a 2-ethylhexyl group, an octyl group, a fluoromethyl group, and a trifluoromethyl group.

In the formula (a1-5), $R^{a8}$ preferably represents a hydrogen atom, a methyl group, or trifluoromethyl group.

$L^{51}$ represents preferably an oxygen atom.

It is preferred that one of $L^{52}$ and $L^{53}$ represents an oxygen atom, while the other represents a sulfur atom.

s1 preferably represents 1. s1' represents an integer of 0 to 2. $Z^{a1}$ preferably represents a single bond or *—$CH_2$—CO—O— wherein * represents a binding position to $L^{51}$.

Examples of the monomer from which the structural unit (a1-5) is derived include one mentioned in JP2010-61117A1 and the following ones:

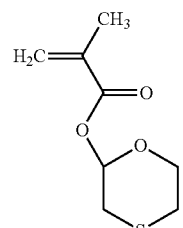
(a1-5-1)

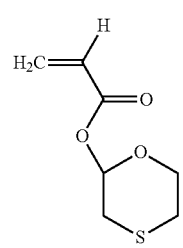
(a1-5-2)

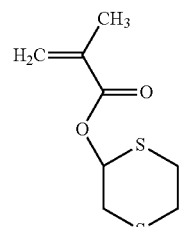
(a1-5-3)

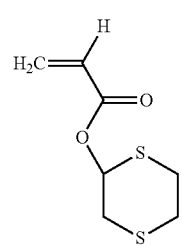
(a1-5-4)

When Resin (A) has a structural unit (a1-5), its content is usually 1 to 50% by mole, preferably 3 to 45% by mole and more preferably 5 to 40% by mole, and still more preferably 5 to 30% by mole, based on 100% by mole based on 100% by mole of all the structural units of the resin.

Other examples of the structural unit (A1) include the following ones.

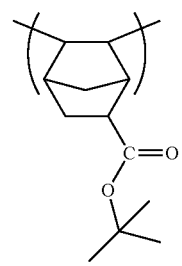
(a1-3-1)

(a1-3-2)

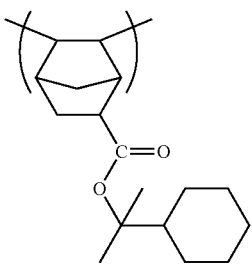

(a1-3-3)

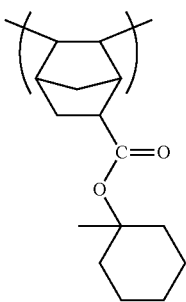

(a1-3-4)

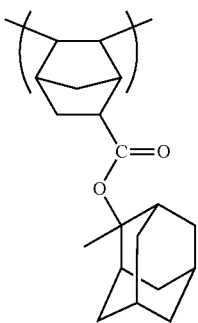

(a1-3-5)

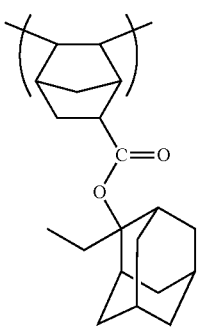

(a1-3-6)

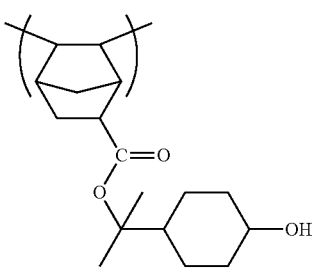

(a1-3-7)

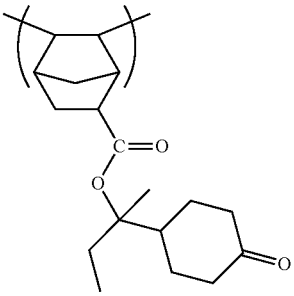

When Resin (A) has any one of these structural units, its content is usually 10 to 95% by mole, preferably 15 to 90% by mole, more preferably 20 to 85% by mole, still more preferably 20 to 70% by mole, and further more preferably 20 to 60% by mole, based on 100% by mole of all the structural units of the resin.

The structural unit(s) is derived from a monomer having no acid-labile group.

The structural unit(s) preferably has a hydroxy group or a lactone ring.

Hereinafter, the structural unit(s) having a hydroxy group is referred to as "structural unit (a2)", and the structural unit (s) having a lactone ring is referred to as "structural unit (a3)".

The hydroxy group which the structural unit (a2) has may be an alcoholic hydroxy group or a phenolic hydroxy group. When KrF excimer laser (wavelength: 248 nm) lithography system, or a high energy laser such as electron beam and extreme ultraviolet is used as an exposure system, the resin which comprises the structural unit (a2) having a phenolic hydroxy group is preferred. When ArF excimer laser (wavelength: 193 nm) is used as an exposure system, the resin which comprises the structural unit (a2) having an alcoholic hydroxy group is preferred and the resin which comprises the structural unit (a2-1) described later is more preferred.

Resin (A) may have two or more of the structural units (a2).

Examples of the structural unit (a2) having a phenolic hydroxy group include one represented by formula (a2-A):

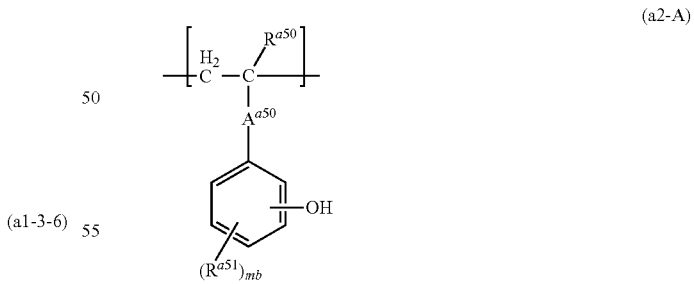

(a2-A)

In formula (a2-A), $R^{a50}$ represents a hydrogen atom, a halogen atom, a C1-C6 alkyl group or a C1-C6 halogenated alkyl group, $A^{a50}$ represents a single bond or *—$X^{a51}$-($A^{a52}$-$X^{a52}$)$_{nb}$—, where * represents a binding position to the carbon atom bonded to $R^{a50}$, $A^{a52}$ represents a C1-C6 alkanediyl group, $X^{a51}$ and $X^{a52}$ represents —O—, —CO—O—, or —O—CO—, and nb represents an integer of 0 or 1, $R^{a51}$ is independently in each occurrence a halogen atom, a hydroxy group, a C1-C6 alkyl group, a C1-C6 alkoxy group, a C2-C4 acyl group, a C2-C4 acyloxy group, an acryloyl group or a methacryloyl group, and mb represents an integer of 0 to 4.

In the formula (a2-0), examples of the halogen atom include a fluorine atom, a chlorine atom, a bromine atom or iodine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferred and a C1-C2 alkyl group is more preferred and a methyl group is especially preferred.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferred and a C1-C2 alkoxy group is more preferred and a methoxy group is especially preferred.

Examples of the C2-C4 acyl group include an acetyl group, a propyonyl group and a butyryl group, and examples of the C2-C4 acyloxy group include an acetyloxy group, a propyonyloxy group and a butyryloxy group.

$R^{a51}$ is preferably a methyl group.

$R^{a50}$ is preferably a hydrogen atom and a C1-C4 alkyl group, more preferably a hydrogen atom, a methyl group and an ethyl group, and still more preferably a hydrogen atom and a methyl group.

As to $A^{a50}$, examples of *—$X^{a51}$-($A^{a52}$-$X^{a52}$)$_{nb}$— include *—O—, *—CO—O—, *—O—CO—, *—CO—O-$A^{a52}$-CO—O—, *—O—CO-$A^{a52}$-O—, *—O-$A^{a52}$-CO—O—, *—CO—O-$A^{a52}$-O—CO—, *—O—CO-$A^{a52}$-O—CO—, preferably *—CO—O—, *—CO—O-$A^{a52}$-CO—O— and *—O-$A^{a52}$-CO—O—.

As to $A^{a52}$, examples of the alkanediyl group include an ethylene group, a propane-1,3-diyl group, a propane-1,2-diyl group, a butane-1,4-diyl group, a pentane-1,5-diyl group, a hexane-1,6-diyl group, a butane-1,3-diyl group, a 2-methylpropane-1,3-diyl group, a 2-methylpropane-1,2-diyl group, a pentane-1,4-diyl group and a 2-methylbutane-1,4-diyl group.

$A^{a50}$ is preferably a single bond, *—CO—O— or *—CO—O-$A^{a52}$-O—CO—, more preferably a single bond, *—CO—O— or *—CO—O—CH$_2$—O—CO—, and still more preferably a single bond or *—CO—O—.

In the formula (a2-A), ma is preferably 0, 1 or 2, and is more preferably 0 or 1, and especially preferably 0.

In formula (a2-A), a hydroxyl group on the phenyl group is positioned preferably on o-position or p-position, and more preferably on p-position.

Examples of the structural unit (a2) include those derived from the monomers described in JP2010-204634A1 and JP2012-12577A1. Preferred examples of the structural unit (a2) include the structural units represented by formulae (a2-2-1) to (a2-2-4) and those represented by formulae in which a methyl group corresponding to $R^{a50}$ has been replaced by a hydrogen atom.

Among them, the structural units represented by formulae (a2-2-1) and (a2-1-3) and those represented by formulae in which a methyl group corresponding to $R^{a50}$ has been replaced by a hydrogen atom are more preferred.

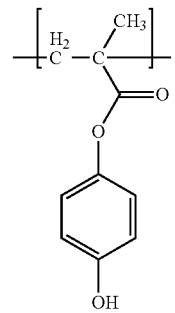

(a2-2-1)

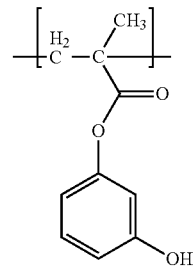

(a2-2-2)

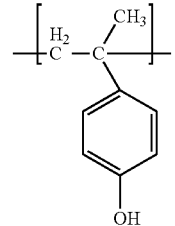

(a2-2-3)

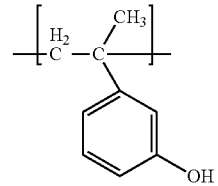

(a2-2-4)

When Resin (A) has the structural unit represented by formula (a2-A), its content is usually 5 to 95% by mole and preferably 10 to 80% by mole, more preferably 15 to 80% by mole, still more preferably 10 to 70% by mole, further more preferably 15 to 65% by mole, and still further more preferably 20 to 65% by mole, based on sum of the structural units of the resin.

Examples of the structural unit (a2) having an alcoholic hydroxy group include one represented by formula (a2-1):

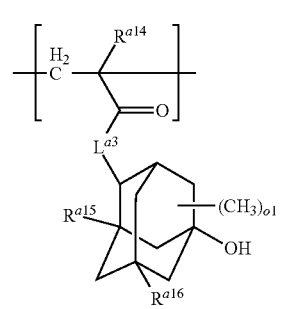

(a2-1)

wherein $R^{a14}$ represents a hydrogen atom or a methyl group, $R^{a15}$ and $R^{a16}$ each independently represent a hydrogen atom, a methyl group or a hydroxy group, $L^{a3}$ represents *—O— or *—O—$(CH_2)_{k2}$—CO—O— in which * represents a binding position to —CO—, and k2 represents an integer of 1 to 7, and o1 represents an integer of 0 to 10.

Hereinafter, the structural unit represented by formula (a2-1) is referred to as "structural unit (a2-1)".

In the formula (a2-1), $R^{a14}$ is preferably a methyl group. $R^{a15}$ is preferably a hydrogen atom. $R^{a16}$ is preferably a hydrogen atom or a hydroxy group. $L^{a3}$ is preferably *—O— or *—O—$(CH_2)_{f2}$—CO—O— in which * represents a binding position to —CO—, and f2 represents an integer of 1 to 4, is more preferably *—O— and *—O—$CH_2$—CO—O—, and is still more preferably *—O—, and o1 is preferably 0, 1, 2 or 3 and is more preferably 0 or 1.

Examples of monomers from which the structural unit (a2-1) is derived include compounds mentioned in JP2010-204646A.

Preferred examples of the structural unit (a2-1) include those represented by formulae (a2-1-1) to (a2-1-6).

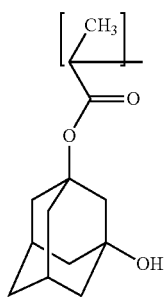
(a2-1-1)

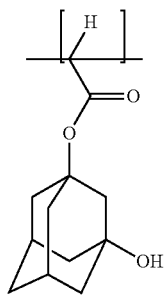
(a2-1-2)

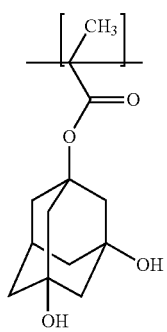
(a2-1-3)

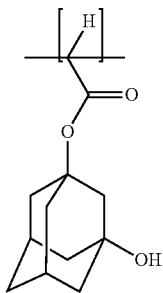
(a2-1-4)

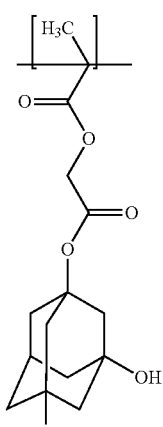
(a2-1-5)

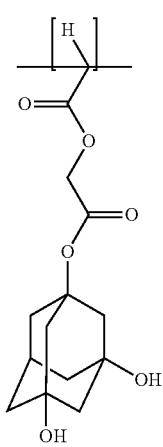
(a2-1-6)

Among them, more preferred are the structural units represented by formulae (a2-1-1), (a2-1-2), (a2-1-3) and (a2-1-4), still more preferred are the structural units represented by formulae (a2-1-1) and (a2-1-3).

When Resin (A) has the structural unit (a2-1), its content is usually 1 to 45% by mole, preferably 1 to 40% by mole, and more preferably 1 to 35% by mole, still more preferably 2 to 20% by mole, further still more preferably 2 to 10% by mole, based on sum of the structural units of the resin.

Examples of the lactone ring for the structural unit (a3) include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferred examples of the structural unit (a3) include those represented by formulae (a3-1), (a3-2), (a3-3) and (a3-4).

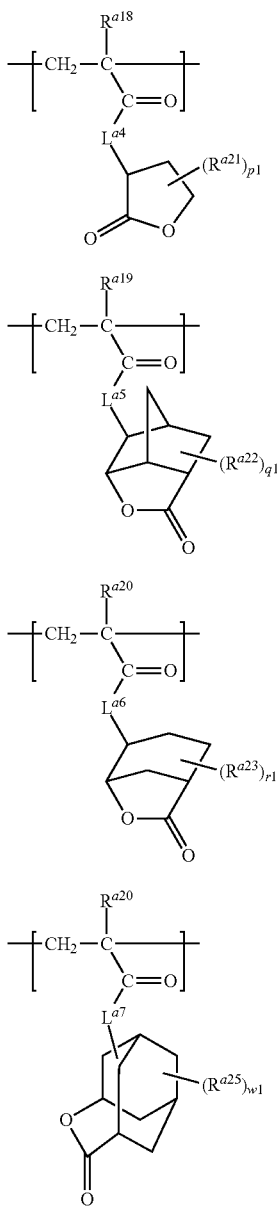

(a3-1)

(a3-2)

(a3-3)

(a3-4)

In formulae, $L^{a4}$, $L^{a5}$ and $L^{a6}$ each independently represent *—O— or *—O—$(CH_2)_{k3}$—CO—O— in which * represents a binding position to a carbonyl group and k3 represents an integer of 1 to 7, $R^{a18}$, $R^{a19}$ and $R^{a20}$ each independently represent a hydrogen atom or a methyl group, $R^{a21}$ represents a C1-C4 monovalent aliphatic hydrocarbon group, $R^{a24}$ each independently represent a hydrogen atom, a halogen atom, or a C1-C6 alkyl group which may have a halogen atom, $R^{a22}$, $R^{a23}$ and $R^{a25}$ each independently represent a carbonyl group, a cyano group, or a C1-C4 aliphatic hydrocarbon group, $L^{a7}$ represents an oxygen atom, *¹—O-$L^{a8}$-O—, *¹—O-$L^{a8}$-CO—O—, *¹-O-$L^{a8}$-CO—O-$L^{a9}$-CO—O— or *—O-$L^{a8}$-CO—O-$L^{a9}$-O— in which $L^{a8}$ and $L^{a9}$ each independently represent C1-C6 divalent alkanediyl group, *¹ represents a binding position to a carbonyl group, p1 represents an integer of 0 to 5, q1 and r1 independently each represent an integer of 0 to 3, and W1 represents an integer of 0 to 8.

Examples of the aliphatic hydrocarbon group represented by $R^{a21}$, $R^{a22}$, $R^{a23}$ and $R^{a25}$ include alkyl groups such as a methyl group, an ethyl group, a propyl group, or a butyl group.

Examples of the alkyl group represented by $R^{a24}$ include a methyl group, an ethyl group, a propyl group, a butyl group, a pentyl group, and a hexyl group, preferably a C1-C4 alkyl group, and more preferably a methyl group and an ethyl group.

Examples of halogen atom represented by $R^{a24}$ include a fluorine atom, a chlorine atom, a bromine atom and an iodine atom.

As to $R^{a24}$, examples of the alkyl group which has an halogen atom include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group, a perfluorohexyl group, a trichloromethyl group, a tribromomethyl group, and a triiodomethyl group.

As to $L^{a8}$ and $L^{a9}$, examples of the alkanediyl group include a methylene group, an ethylene group, a propane-1,3-diyl group, a butane-1,4-diyl group, a pentane-1,5-diyl group and a hexane-1,6-diyl group, a butane-1,3-diyl group, 2-methylpropane-1,3-diyl group, a 2-methylpropane-1,2-diyl group, a pentane-1,4-diyl group and a 2-methylbutane-1,4-diyl group.

Preferably, $L^{a4}$, $L^{a5}$ and $L^{a6}$ each independently represent *—O— or *—O—$(CH_2)$ dl-CO—O— in which * represents a binding position to —CO— and dl represents an integer of 1 to 4. More preferably, $L^{a4}$, $L^{a5}$ and $L^{a6}$ are *—O— and *—O—$CH_2$—CO—O—, and still more preferably $L^{a4}$, $L^{a5}$ and $L^{a6}$ are *—O—.

$R^{a1}$, $R^{a19}$ and $R^{a20}$ are preferably methyl groups. $R^{a21}$ is preferably a methyl group. Preferably, $R^{a22}$ and $R^{a23}$ are independently in each occurrence a carboxyl group, a cyano group or a methyl group.

Preferably, p1, q1 and r1 each independently represent an integer of 0 to 2, and more preferably p1, q1 and r1 each independently represent 0 or 1.

$R^{a24}$ is preferably a hydrogen atom or a C1-C4 alkyl group, more preferably a hydrogen atom, a methyl group or an ethyl group, and still more preferably a hydrogen atom or a methyl group.

$L^{a7}$ represents preferably an oxygen atom or *¹—O-$L^{a8}$-CO—O—, more preferably an oxygen atom, *¹—O—$CH_2$—CO—O— or *¹—O—$C_2H_4$—CO—O—.

The formula (a3-4)' is preferably one.

(a3-4)'

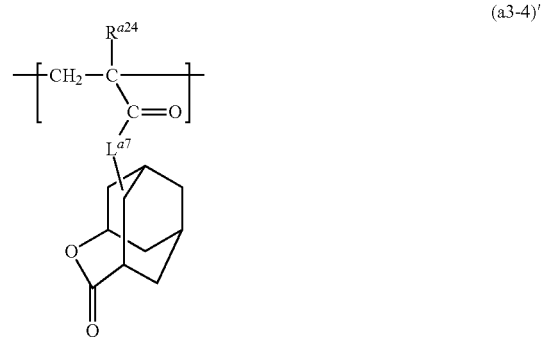

In the formula, $R^{a24}$ and $L^{a7}$ are as defined above, respectively.
Examples of the monomer from which the structural unit (a3) is derived include those mentioned in US2010/203446A1, US2002/098441A1 and US2013/143157A1.
Examples of the structural unit (a3) include the following ones.
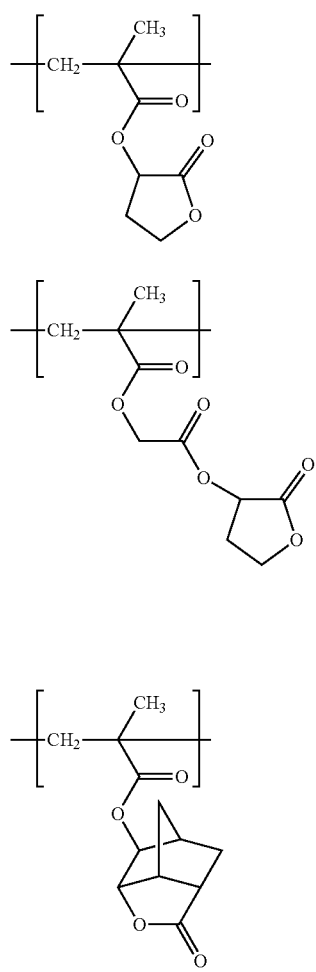
(a3-1-1)
(a3-1-2)
(a3-2-1)
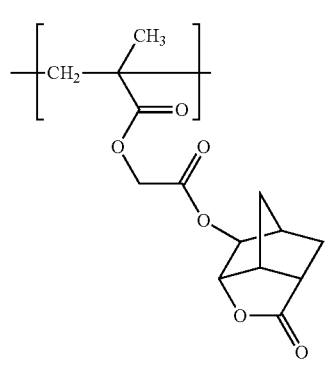
(a3-2-2)
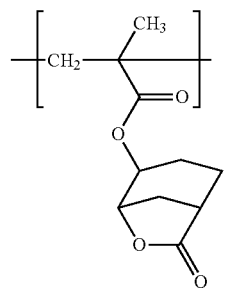
(a3-3-1)
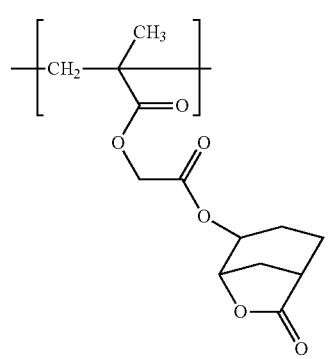
(a3-3-2)
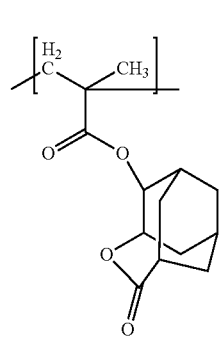
(a3-4-1)
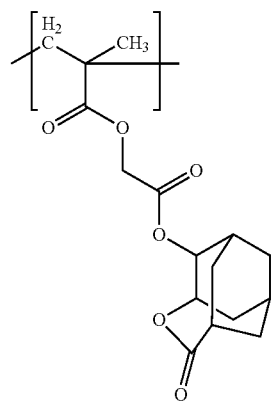
(a3-4-2)

(a3-4-3)
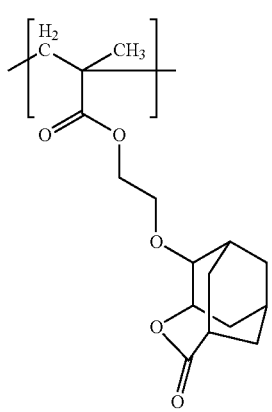
(a3-4-4)
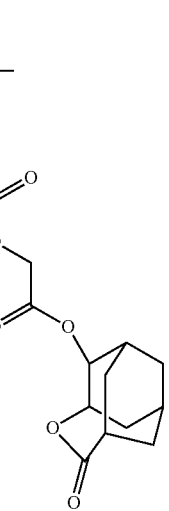
(a3-4-5)
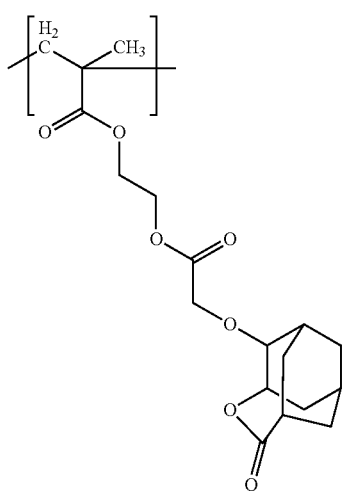
(a3-4-6)
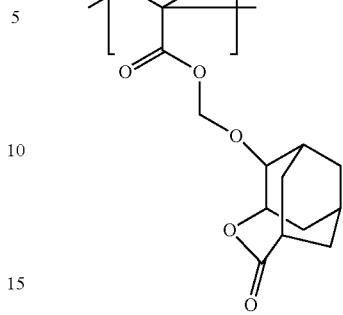
(a3-4-7)
(a3-4-8)
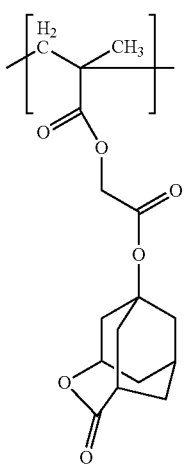
(a3-4-9)
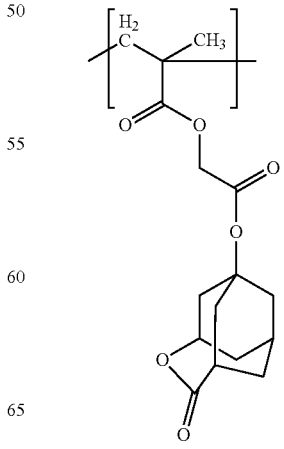

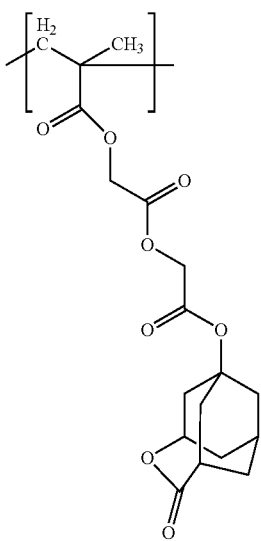

(a3-4-10)

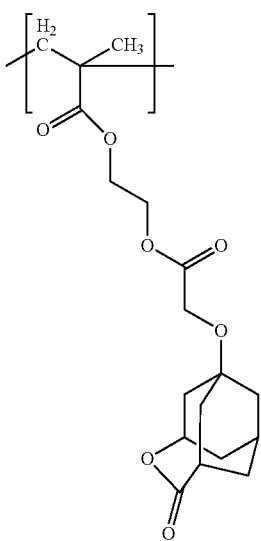

(a3-4-11)

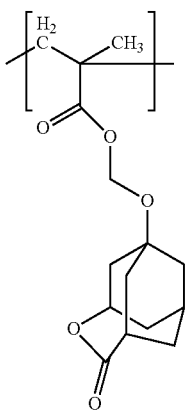

(a3-4-12)

Other examples of the structural unit (a3) include those represented by formulae (a3-1) to (a3-4) in which the methyl group corresponding to $R^{a18}$, $R^{a19}$, $R^{a20}$ and $R^{a24}$ of formula (a3-4) has been replaced by a hydrogen atom.

When Resin (A) has the structural unit (a3), its content thereof is preferably 5 to 70% by mole, and more preferably 10 to 65% by mole and more preferably 10 to 60% by mole, based on sum of the structural units of the resin.

When Resin (A) has the structural unit (a3-1), (a3-2), (a3-3) or (a3-4), its content thereof is preferably 5 to 60% by mole, and more preferably 5 to 50% by mole and more preferably 10 to 50% by mole, based on sum of the structural units of the resin.

Other examples of the structural unit(s) include a structural unit having a fluorine atom and a structural unit which has a hydrocarbon not being removed therefrom by action of an acid.

Hereinafter, the structural unit(s) having a halogen atom is referred to as "structural unit (a4)".

Halogen atoms for the structural unit (a4) may be a fluorine atom, a chlorine atom, a bromine atom, or an iodine atom. The structural unit (a4) has preferably a fluorine atom.

Examples of the structural unit (a4) include the following one.

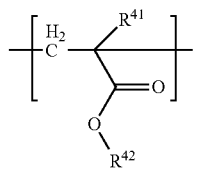

(a4)

In the formula, $R^{41}$ represents a hydrogen atom or a methyl group, $R^{42}$ represents a C1-C24 saturated hydrocarbon group having a fluorine atom in which hydrocarbon group a methylene group can be replaced by an oxygen atom or a carbonyl group.

Examples of the saturated hydrocarbon group include C1-C4 alkanediyl group, i.e., a chain alkyl group such as a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group; and a monocyclic or polycyclic alicyclic hydrocarbon group such as a cycloalkyl group such as a cyclopentyl group, a cyclohexyl group, a cycloheptyl group, and a cyclooctyl group, and a polycyclic alicyclic hydrocarbon group such as a decahydronaphthyl group, an adamantyl group, a norbornyl group and the following groups:

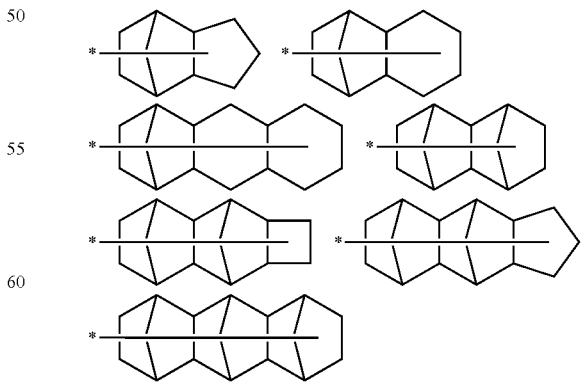

Typical examples of the structural unit (a4) include structural units represented by formulae (a4-0) and (a4-1).

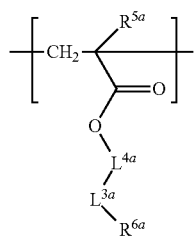
(a4-0)

In the formula (a4-0), $R^{5a}$ represents a hydrogen atom or a methyl group, $L^{4a}$ represents a single bond or a C1-C4 divalent aliphatic saturated aliphatic hydrocarbon group, $L^{3a}$ represents a C1-C8 perfluoroalkanediyl group, or a C3-C12 perfluorocycloalkanediyl group, and $R^{6a}$ represents a hydrogen atom or a fluorine atom.

For $L^{4a}$, examples of the chain or alicyclic hydrocarbon group include a linear alkanediyl group such as a methylene group, an ethylene group, a propane-1,3-diyl group, and butane-1,4-diyl group, and a branched alkanediyl group such as an ethane-1,1-diyl group, a propane-1,2-diyl group, a butane-1,3-diyl group, a 2-methylpropane-1,3-diyl group and 2-methylpropane-1,2-diyl group.

Examples of the perfluoroalkanediyl group for $L^{3a}$ include difluoromethylene, perfluoroethylene, perfluoropropane-1,3-diyl, perfluoropropane-1,2-diyl, perfluoropropane-2,2-diyl, perfluorobutane-1,4-diyl, perfluorobutane-2,2-diyl, perfluorobutane-1,2-diyl, perfluoropentane-1,5-diyl, perfluoropentane-2,2-diyl, perfluoropentane-3,3-diyl, perfluorohexane-1,6-diyl, perfluorohexane-2,2-diyl, perfluorohexane-3,3-diyl, perfluoroheptane-1,7-diyl, perfluoroheptane-2,2-diyl, perfluoroheptane-3,4-diyl, perfluoroheptane-4,4-diyl, perfluorooctan-1,8-diyl, perfluorooctan-2,2-diyl, perfluorooctan-3,3-diyl and perfluorooctan-4,4-diyl groups.

Examples of the perfluorocycloalkanediyl group for $L^{3a}$ include perfluorocyclohexanediyl, perfluorocyclopentanediyl, perfluorocycloheptanediyl and perfluoroadamantanediyl groups.

$L^{3a}$ is preferably a C1-C6 perfluoroalkanediyl group, more preferably a C1-C3 perfluoroalkanediyl group.

$L^{4a}$ is preferably a single bond, a methylene group or an ethylene group, more preferably a single bond or a methylene group.

Examples of the structural unit represented by formula (a4-0) include the structural units represented by the following formulae and those represented by the following formulae in which a methyl group has been replaced by a hydrogen atom.

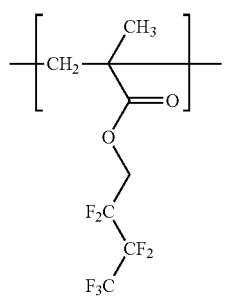
(a4-0-1)

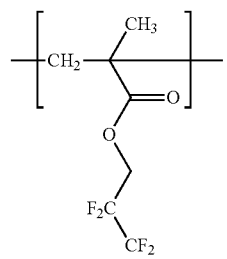
(a4-0-2)

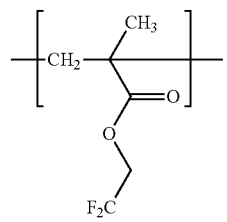
(a4-0-3)

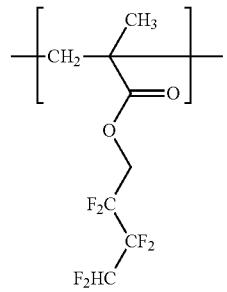
(a4-0-4)

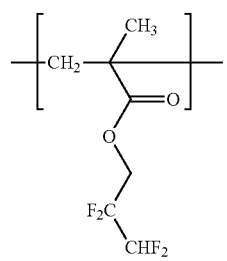
(a4-0-5)

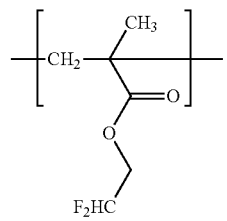
(a4-0-6)

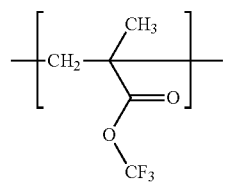
(a4-0-7)

(a4-0-8) 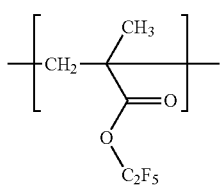

(a4-0-9) 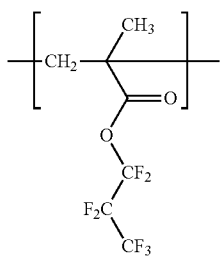

(a4-0-10) 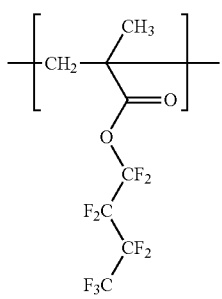

(a4-0-11) 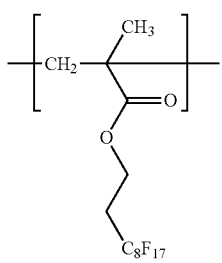

(a4-0-12) 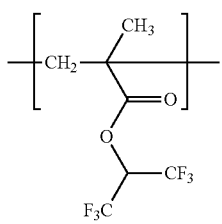

(a4-0-13) 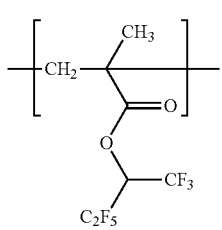

(a4-0-14) 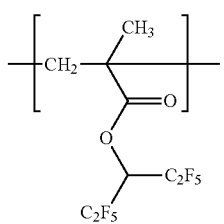

(a4-0-15) 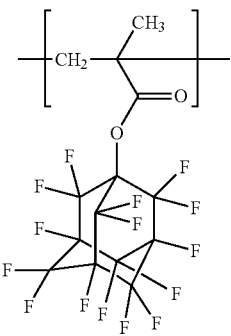

(a4-0-16)

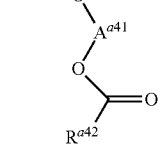

The structural unit represented by formula (a4-1) is as follow.

(a4-1)

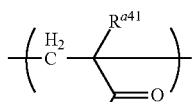

In the formula, $R^{a4}1$ represents a hydrogen atom or a methyl group;

$A^{a41}$ represents a C1-C6 alkanediyl group which may have a substituent or a moiety represented by formula (a-g1):

$$-A^{a42}-(-X^{a41}-A^{a43}-)_s-X^{a42}-A^{a44}-$$ (a-g1)

in which s represents an integer of 0 to 1, $A^{a42}$ and $A^{a44}$ respectively represent a C1-C5 hydrocarbon group which may have a substituent, $A^{a43}$ represents a single bond or a C1-C5 chain or alicyclic hydrocarbon group which may have a substituent, $X^{a41}$ and $X^{a42}$ respectively represent —O—, —CO—, —CO—O—, or —O—CO—, provided that the sum of carbon atoms of $A^{a42}$, $A^{a43}$, $A^{a44}$, $X^{a41}$ and $X^{a42}$ is 7 or less;

$R^{a42}$ represents a C1-C20 saturated hydrocarbon group which may have a substituent and in which a methylene group can be replaced by an oxygen atom or a carbonyl group, provided that each or both of $A^{a41}$ and $R^{a42}$ have a fluorine atom; and $A^{a44}$ is bonded to —O—CO—$R^{a42}$.

The hydrocarbon group for $R^{a42}$ includes a chain hydrocarbon group, an alicyclic hydrocarbon group, an aromatic hydrocarbon group and any combination of these hydrocarbon groups.

The chain hydrocarbon group and an alicyclic hydrocarbon group are preferably a chain or alicyclic hydrocarbon group while they may have a carbon-carbon double bond.

Examples of the chain or alicyclic hydrocarbon group include alkanediyl groups which may be a linear or branched one, alicyclic hydrocarbon groups, and combination of them.

Examples of the chain hydrocarbon group include a methyl group, an ethyl group, a propyl group, a butyl group, a pentyl group, a hexyl group, a heptyl group, an octyl group, a decyl group, a dodecyl group, a hexadecyl group, a pentadecyl group, a hexyldecyl group, heptadecyl group and an octadecyl group.

Examples of cyclic hydrocarbons include cycloalkyl groups such as a cyclopentyl group, a cyclohexyl group, a cycloheptyl group and a cyclooctyl group; and monovalent polycyclic hydrocarbon groups such as a decahyrdonaphthyl group, an adamantyl group, a norbornyl group, and the following groups where * represents a binding position.

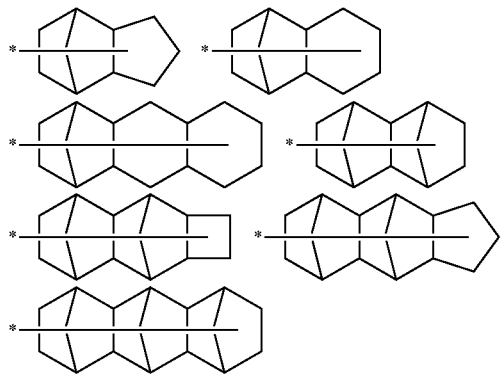

Examples of the aromatic hydrocarbon groups include a phenyl group, a naphthyl group, an anthryl group, a biphenylyl group, a phenanthryl group and a fluorenyl group.

The monovalent chain and cyclic hydrocarbon groups are preferably an alkyl group and an alicyclic hydrocarbon group.

Examples of the alkyl group include a methyl group, an ethyl group, a propyl group, an isopropyl group, a butyl group, an isobutyl group, a tert-butyl group, a pentyl group, a hexyl group, an octyl group and a 2-ethylhexyl group.

The hydrocarbon group represented by $R^{a42}$ preferably has a substituent.

Examples of the substituent include a halogen atom and a group represented by formula (a-g3):

$$—X^{a43}-A^{a45} \qquad (a\text{-}g3)$$

in which $X^{a43}$ represents an oxygen atom, a carbonyl group, a carbonyloxy group or an oxycarbonyl group, and $A^{a45}$ represents a C1-C17 chain or alicyclic hydrocarbon group which has a fluorine atom.

Examples of the chain or alicyclic hydrocarbon group for $A^{a45}$ include those of the chain or alicyclic hydrocarbon group for $R^{a42}$.

$R^{a42}$ is preferably a chain or alicyclic hydrocarbon group which may have a halogen atom, more preferably an alkyl group which has a halogen atom or a group represented by formula (a-g3).

If $R^{a42}$ is a chain or alicyclic hydrocarbon group which has a halogen atom, it is preferably a chain or alicyclic hydrocarbon group which has a fluorine atom, more preferably a perfluoroalkyl group or a perfluorocycloalkyl group, and still more preferably a C1-C6, especially C1-C3, perfluoroalkyl group.

Specific examples of the perfluoroalkyl group include a perfluoromethyl group, a perfluoroethyl group, a perfluoropropyl group, a perfluorobutyl group, a perfluoropentyl group, a perfluorohexyl group, a perfluoroheptyl group, and a perfluorooctyl group. Specific examples of the perfluorocycloalkyl group include a perfluorocyclohexyl group.

Examples of the substituents for $R^{a42}$ include a hydroxy group, a C1-C6 alkoxy group, and a halogen atom such as fluorine atom.

If $R^{a42}$ is a chain or alicyclic hydrocarbon group which has a group represented by formula (a-g3), $R^{a42}$ has preferably 15 or less carbon atoms, more preferably 12 or less carbon atoms.

If $R^{a42}$ has a group represented by formula (a-g3), $R^{a42}$ has preferably one group represented by formula (a-g3).

The chain or alicyclic hydrocarbon group which has a group represented by formula (a-g3) is preferably a group represented by formula (a-g2):

$$-A^{a46}-X^{a44}-A^{a47} \qquad (a\text{-}g2)$$

in which $A^{a46}$ represents a C1-C17 chain or alicyclic hydrocarbon group which may have a fluorine atom, $X^{a44}$ represents a carbonyloxy group or an oxycarbonyl group, and $A^{a47}$ represents a C1-C17 chain or alicyclic hydrocarbon group which may have a fluorine atom, provided that $A^{a46}$, $A^{a47}$ and $X^{a44}$ have 18 or less of carbon atoms in total and one or both of $A^{a46}$ and $A^{a47}$ have a fluorine atom.

The chain or alicyclic hydrocarbon group represented by $A^{a46}$ has preferably 1 to 6, more preferably 1 to 3 carbon atoms.

The chain or alicyclic hydrocarbon group represented by $A^{a47}$ has preferably 4 to 15, more preferably 5 to 12 carbon atoms. $A^{a47}$ is more preferably a cyclohexyl group or an adamantyl group.

Examples of the moiety represented by -$A^{a46}$-$X^{a44}$-$A^{a47}$ include the following ones.

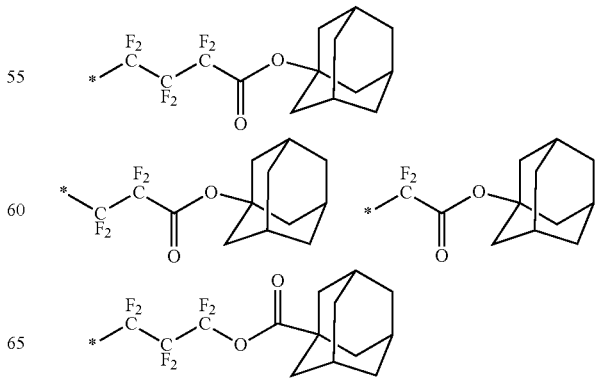

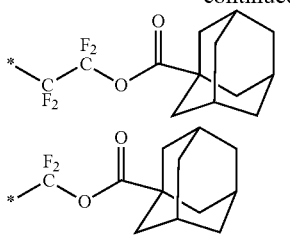

In each formula, * represents a binding position to a carbonyl group.

Examples of $A^{a41}$ typically include a C1-C6 alkanediyl group which may be a linear chain or branched chain. Specific examples of them include linear chain alkanediyl groups such as a methylene group, an ethylene group, a propane-1,3-diyl group, a butane-1,4-diyl group, a pentane-1,5-diyl group, or a hexane-1,6-diyl group; and branched chain alkanediyl groups such as a propane-1,3-diyl group, a butane-1,3-diyl group, a 1-methylbutane-1,2-diyl group, or a 2-methylbutane-1,4-diyl group. Examples of the substituents which such alkanediyl group may have include a hydroxy group or a C1-C6 alkoxy group.

$A^{a41}$ is preferably a C1-C4 alkanediyl group, more preferably a C2-C4 alkanediyl group, and still more preferably an ethylene group.

Examples of the alkanediyl group represented by $A^{a42}$, $A^{a43}$ and $A^{a44}$ include a methylene group, an ethylene group, a propane-1,3-diyl group, a butane-1,4-diyl group, a 2-methylpropane-1,3-diyl group, or a 2-methylbutane-1,4-diyl group. Examples of the substituents which such alkanediyl group may have include a hydroxy group or a C1-C6 alkoxy group.

$X^{a42}$ represents an oxygen atom, a carbonyl group, a carbonyloxy group or an oxycarbonyl group.

Examples of the moiety represented by formula (a-g1) where $X^{a42}$ is an oxygen atom, a carbonyl group, a carbonyloxy group or an oxycarbonyl group include the following ones:

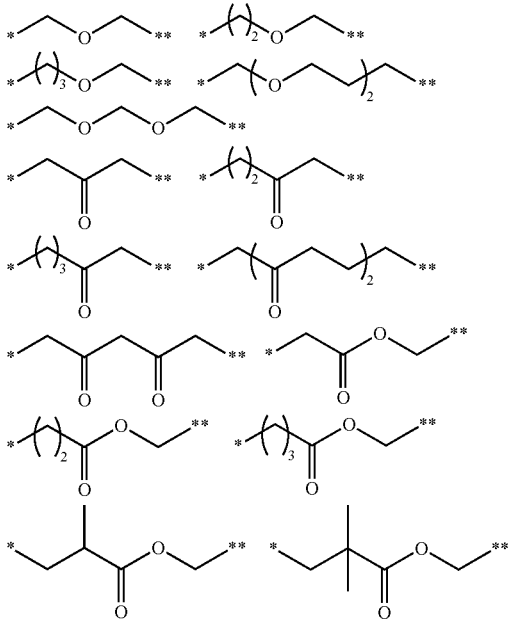

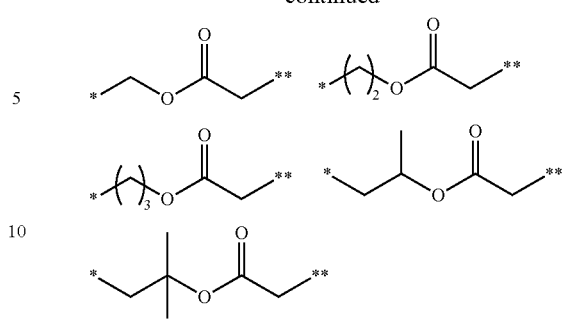

in which * and  represent binding positions, and  represents a binding position to —O—CO—$R^{a42}$.

Typical examples of the structural unit represented by formulae (a4-1) include the structural units represented by the following formulae and those represented by the following formulae in which a methyl group has been replaced by a hydrogen atom.

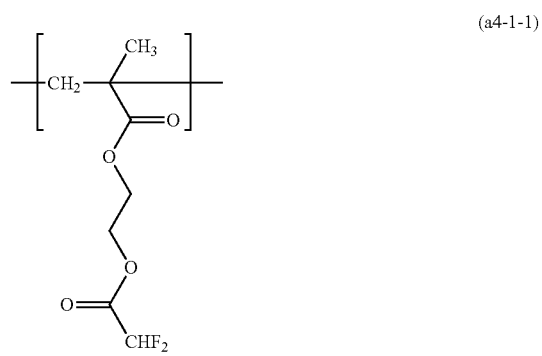

(a4-1-1)

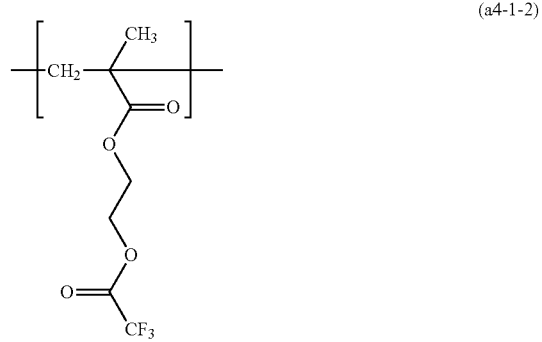

(a4-1-2)

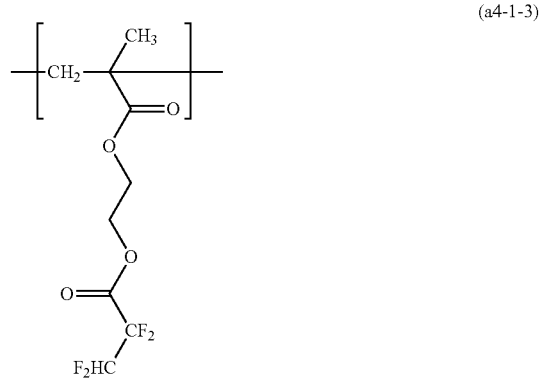

(a4-1-3)

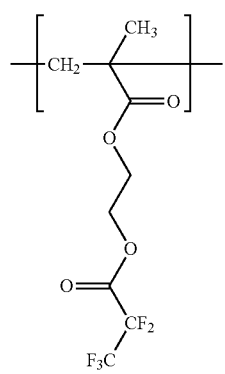 (a4-1-4)
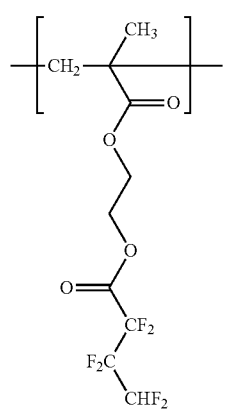 (a4-1-5)
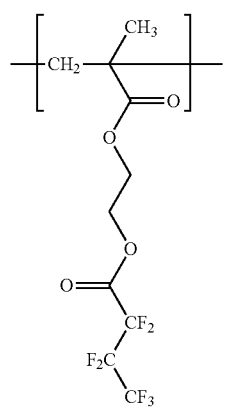 (a4-1-6)
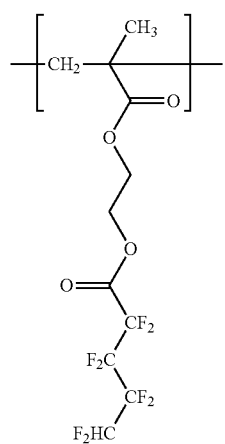 (a4-1-7)
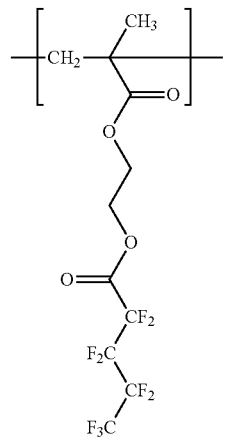 (a4-1-8)
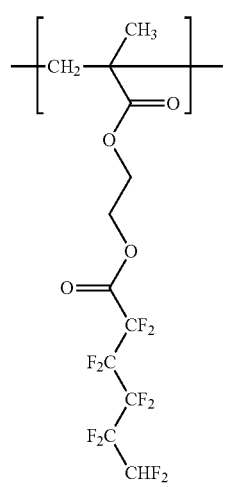 (a4-1-9)
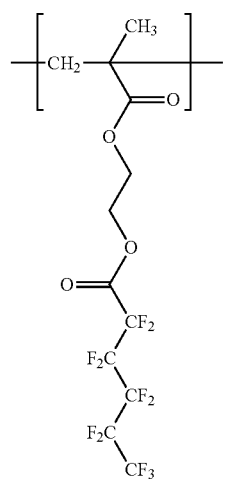 (a4-1-10)

-continued
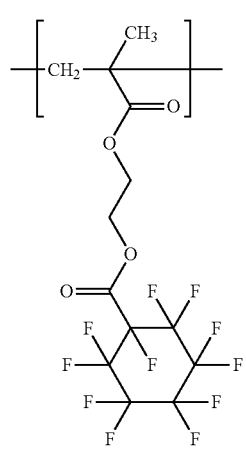
(a4-1-11)
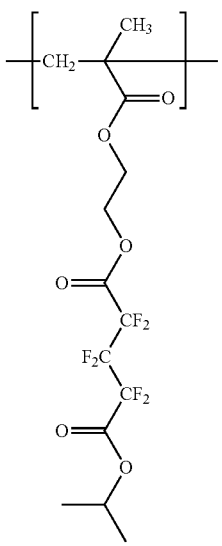
(a4-1'-3)
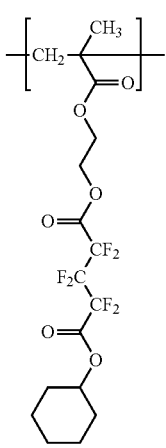
(a4-1'-1)
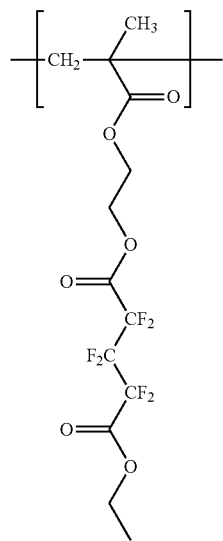
(a4-1'-4)
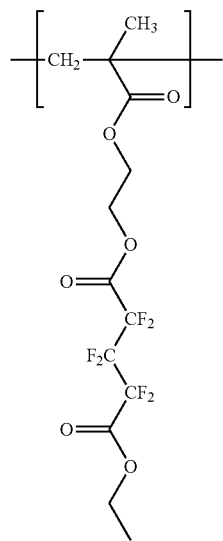
(a4-1'-2)
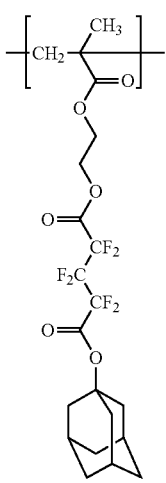
(a4-1'-5)

(a4-1'-6) 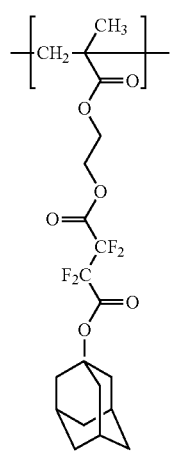
(a4-1'-7) 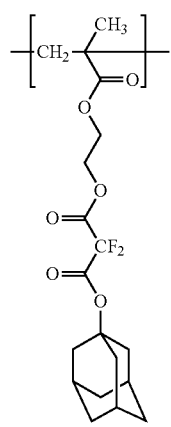
(a4-1'-8) 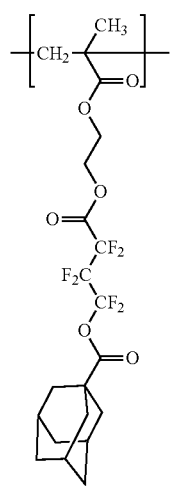
(a4-1'-9) 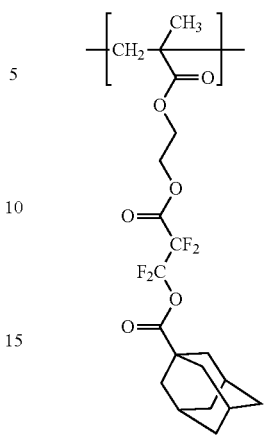
(a4-1'-10) 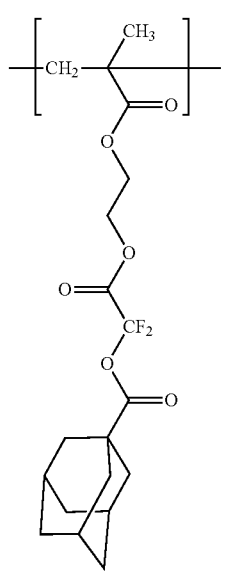
(a4-1'-11) 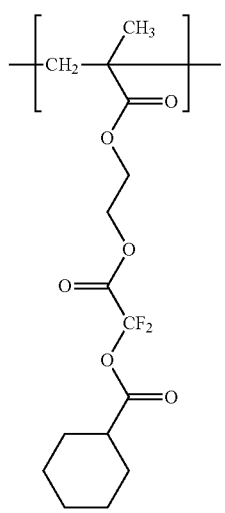
The structural unit represented by the formula (a4-1) is typically a structural unit represented by formula (a4-2):

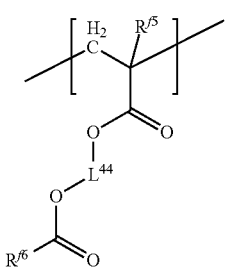

(a4-2)

wherein $R^{f5}$ represents a hydrogen atom or a methyl group, $L^{44}$ represent a C1-C18 divalent saturated hydrocarbon group in which a methylene group can be replaced by —O— or —CO—, and $R^{f6}$ represents a C1-C20 hydrocarbon group that has a fluorine atom, provided that $L^{44}$ and $R^{f6}$ have 2 to 21 carbon atoms in total.

Examples of the divalent saturated hydrocarbon group for $L^{44}$ include a linear alkanediyl group such as methylene, ethylene, propane-1,3-diyl, propane-1,2-diyl, butane-1,4-diyl, pentane-1,5-diyl and hexane-1,6-diyl groups;

a branched alkanediyl group such as 1-methylpropane-1,3-diyl, 2-methylpropane-1,3-diyl, 2-methylpropane-1,2-diyl, 1-methylbutane-1,4-diyl and 2-methylbutane-1,4-diyl groups;

divalent monocyclic hydrocarbon groups such as cycloalkanediyl groups such as a cyclopentanediyl group and a cyclohexanediyl group; and divalent polycyclic alicyclic hydrocarbon groups such as an adamantanediyl group and a norbornanediyl group.

Examples of the hydrocarbon group for $R^{f6}$ include an aliphatic hydrocarbon group and an aromatic hydrocarbon group. The aliphatic hydrocarbon group includes chain and cyclic groups, and a combination thereof. The aliphatic hydrocarbon group is preferably an alkyl group and a cyclic aliphatic hydrocarbon group.

Examples of the alkyl group include methyl, ethyl, n-propyl, isopropyl, n-butyl, sec-butyl, tert-butyl, n-pentyl, n-hexyl, n-heptyl, n-octyl and 2-ethylhexyl groups.

Examples of the cyclic aliphatic hydrocarbon group include any of a monocyclic group and a polycyclic group. Examples of the monocyclic alicyclic hydrocarbon group include a cycloalkyl group such as cyclopropyl, cyclobutyl, cyclopentyl, cyclohexyl, methylcyclohexyl, dimethylcyclohexyl, cycloheptyl, cyclooctyl, and cyclodecyl groups. Examples of the polycyclic hydrocarbon groups includes decahydronaphthyl, adamantyl, 2-alkyladamantane-2-yl, 1-(adamantane-1-yl)alkane-1-yl, norbornyl, methylnorbornyl and isobornyl groups.

Examples of the hydrocarbon group having a fluorine atom for $R^{f2}$ include an alkyl group having a fluorine atom and an alicyclic hydrocarbon group having a fluorine atom.

Specific examples of an alkyl group having a fluorine atom include a fluorinated alkyl group such as difluoromethyl, trifluoromethyl, 1,1-difluoroethyl, 2,2-difluoroethyl, 2,2,2-trifluoroethyl, perfluoroethyl, 1,1,2,2-tetrafluoropropyl, 1,1,2,2,3,3-hexafluoropropyl, perfluoroethylmethyl, 1-(trifluoromethyl)-1,2,2,2-tetrafluoroethyl, perfluoropropyl, 1-(trifluoromethyl)-2,2,2-trifluoroethyl, 1,1,2,2-tetrafluorobutyl, 1,1,2,2,3,3-hexafluorobutyl, 1,1,2,2,3,3,4,4-octafluorobutyl, perfluorobutyl, 1,1-bis(trifluoro)methyl-2,2,2-trifluoroethyl, 2-(perfluoropropyl)ethyl, 1,1,2,2,3,3,4,4-octafluoropentyl, perfluoropentyl, 1,1,2,2,3,3,4,4,5,5-decafluoropentyl, 1,1-bis(trifluoromethyl)-2,2,3,3,3-pentafluoropropyl, 2-(perfluorobutyl)ethyl, 1,1,2,2,3,3,4,4,5,5-decafluorohexyl, 1,1,2,2,3,3,4,4,5,5,6,6-dodecafluorohexyl, perfluoropentylmethyl and perfluorohexyl groups.

Examples of the alicyclic hydrocarbon group having a fluorine atom include a fluorinated cycloalkyl group such as perfluorocyclohexyl and perfluoroadamantyl groups.

In the formula (a4-2), $L^{44}$ is preferably a C2-C4 alkanediyl group, and more preferably an ethylene group.

$R^{f6}$ is preferably a C1-C6 fluorinated alkyl group.

Examples of the structural group represented by formula (a4-2) include ones represented by following formulae and those in which a methyl group has been replaced by a hydrogen atom.

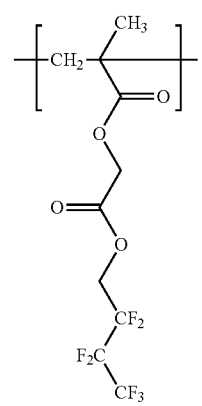

(a4-2-1)

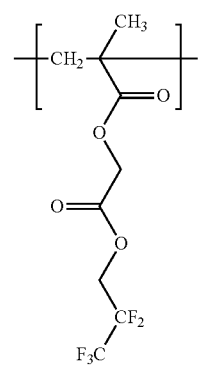

(a4-2-2)

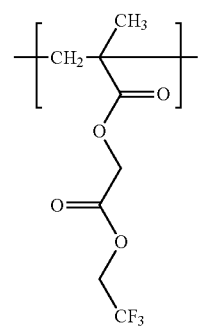

(a4-2-3)

(a4-2-4)

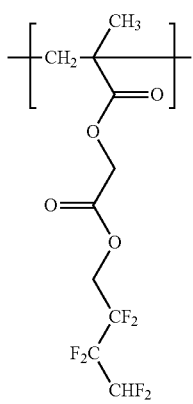

(a4-2-5)

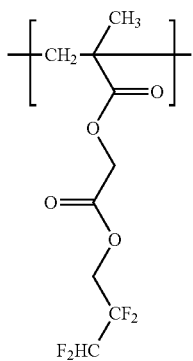

(a4-2-6)

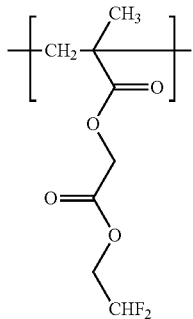

Another typical example of the structural unit represented by the formula (a4-1) includes one represented by formula (a4-3).

(a4-3)

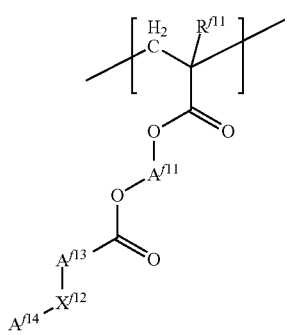

In formula, $R^{f11}$ represents a hydrogen atom or a methyl group.

$A^{f11}$ represents a C1-C6 alkanediyl group.

$A^{f13}$ represents a C1-C18 chain or alicyclic hydrocarbon group which may have a fluorine atom.

$X^{f12}$ represents a carbonyloxy group or an oxycarbonyl group.

$A^{f14}$ represents a C1-C17 chain or alicyclic hydrocarbon group which may have a fluorine atom, provided that one or both of $A^{f13}$ and $A^{f14}$ represents a fluorine-containing aliphatic hydrocarbon group.

Examples of the alkanediyl group for $A^{f11}$ include the same ones as those for $A^{f1}$.

$A^{f13}$ further includes combined groups of chain hydrocarbon groups and alicyclic hydrocarbon groups.

As to $A^{f13}$, the chain or alicyclic hydrocarbon group which may have a fluorine atom is preferably a divalent saturated chain hydrocarbon group which may have a fluorine atom, more preferably a perfluoroalkanediyl group.

Examples of the divalent chain saturated hydrocarbon group which may have a fluorine atom include an alkanediyl group such as a methylene group, an ethylene group, a propanediyl group, a butanediyl group and pentanediyl group; and a perfluoroalkanediyl group such as a difluoromethylene group, a perfluoroethylene group, a perfluoropropanediyl group, a perfluorobutanediyl group and perfluoropentanediyl group.

The divalent cyclic saturated hydrocarbon group which may have a fluorine atom may be a divalent monocyclic or polycyclic group.

Examples of the divalent monocyclic hydrocarbon group which may have a fluorine atom include a cyclohexanediyl group and a perfluorocyclohexanediyl group.

Examples of the divalent polycyclic hydrocarbon group which may have a fluorine atom include an adamantanediyl group, norbornanediyl group, and a perfluoroadamantanediyl group.

In the group represented by $A^{f14}$, the aliphatic hydrocarbon group includes chain saturated hydrocarbon groups, cyclic saturated hydrocarbon groups and combined groups of these saturated hydrocarbon groups.

As to $A^{f14}$, the chain or alicyclic hydrocarbon group which may have a fluorine atom is preferably a saturated aliphatic hydrocarbon group which may have a fluorine atom, more preferably a perfluoroalkanediyl group.

Examples of the chain hydrocarbon group which may have a fluorine atom include a trifluoromethyl group, a fluoromethyl group, a methyl group, a perfluoroethyl group, a 1,1,1-trifluoroethyl group, a 1,1,2,2-tetrafluoroethyl group, an ethyl group, a perfluoropropyl group, a 1,1,1,2,2-pentafluoropropyl group, propyl group, a perfluorobutyl group, 1,1,2,2,3,3,4,4-octafluorobutyl group, a butyl group, a perfluoropentyl group, 1,1,1,2,2,3,3,4,4-nonafluoropentyl group, a pentyl group, a hexyl group, a perfluorohexyl group, a heptyl group, a perfluoroheptyl group, an octyl group and a perfluorooctyl group.

The alicyclic hydrocarbon group which may have a fluorine atom may be monocyclic or polycyclic group.

Examples of the monovalent monocyclic hydrocarbon group which may have a fluorine atom include a cyclopropyl group, cyclopentyl group, cyclohexyl group, and perfluorocyclohexyl group.

Examples of the polycyclic hydrocarbon group which may have a fluorine atom include an adamantyl group, a norbornyl group, and a perfluoroadamantyl group.

Examples of the combined groups of the above-mentioned chain and alicyclic hydrocarbon groups include a cyclopropylmethyl group, a cyclobutylmethyl group, an adamantylmethyl group, a norbornylmethyl group and a perfluoroadamantylmethyl group.

In formula (a4-3), $A^{\prime 11}$ is preferably an ethylene group.

The chain or alicyclic hydrocarbon group represented by $A^{\prime 13}$ has preferably 6 or less, more preferably 2 to 3, of carbon atoms.

The chain or alicyclic hydrocarbon group represented by $A^{\prime 14}$ has preferably 3 to 12, more preferably 3 to 10, of carbon atoms.

$A^{\prime 14}$ has preferably a C3-C12 alicyclic hydrocarbon group, more preferably a cyclopropylmethyl group, a cyclopentyl group, a cyclohexyl group, a norbornyl group or an adamantyl group.

Examples of the structural unit represented by formula (a4-3) include preferably those represented by the following formulae and those represented by the formulae in which the methyl group corresponding to $R^{\prime 11}$ of formula (a4-3) has been replaced by a hydrogen atom.

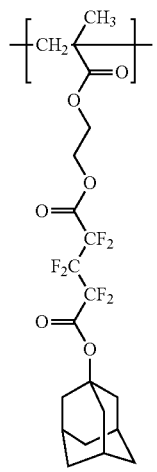

(a4-3-1)

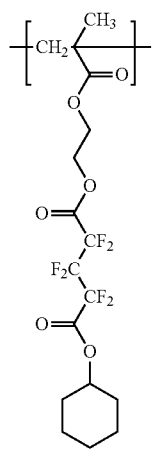

(a4-3-2)

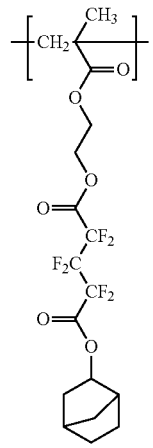

(a4-3-3)

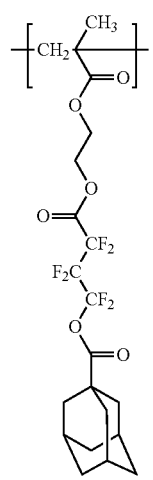

(a4-3-4)

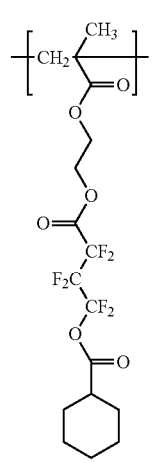

(a4-3-5)

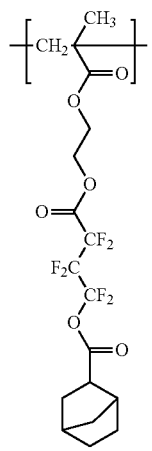

(a4-3-6)

Another typical example of the structural unit (a4-1) includes those represented by formula (a4-4).

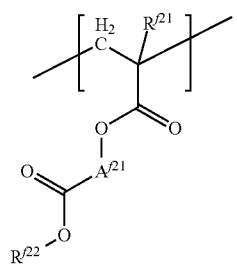

(a4-4)

In formula (a4-4), wherein $R'^{21}$ represents a hydrogen atom or a methyl group;

$A'^{21}$ represents $-(CH_2)_{j1}-$, $-(CH_2)_{j2}-O-(CH_2)_{j3}-$ or $-(CH_2)_{j4}-CO-O-(CH_2)_{j5}-$ where j1, j2, j3, j4 or j5 each independently represent an integer of 1 to 6; and $R'^{22}$ represents a C1-C10 hydrocarbon group having a fluorine atom.

For $R'^{22}$, examples of the hydrocarbon group having a fluorine atom include those as referred to for $R'^{2}$.

$R'^{22}$ is preferably a C1-C10 alkyl group having a fluorine atom or a C3-C10 alicyclic hydrocarbon group having a fluorine atom, more preferably a C1-C10 alkyl group having a fluorine atom, and still more preferably a C1-C6 alkyl group having a fluorine atom.

In formula (a4-4), $A'^{21}$ is preferably $-(CH_2)_{j1}-$, more preferably a methylene or ethylene group, and still more preferably a methylene group.

Examples of the structural unit represented by formula (a4-4) include preferably the following ones and those represented by the following formulae in which the methyl group corresponding to $R'^{21}$ has been replaced by a hydrogen atom.

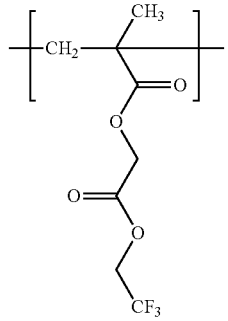 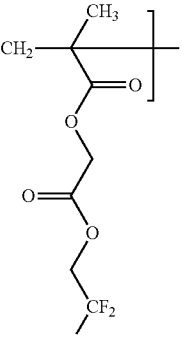

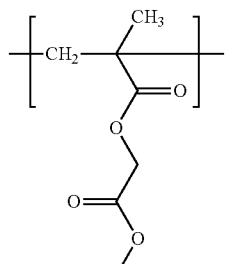 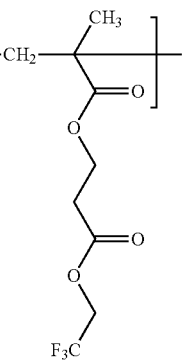

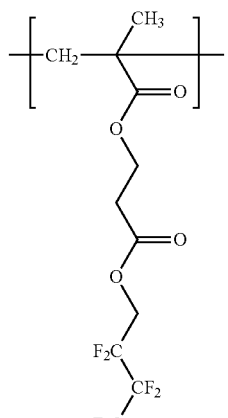 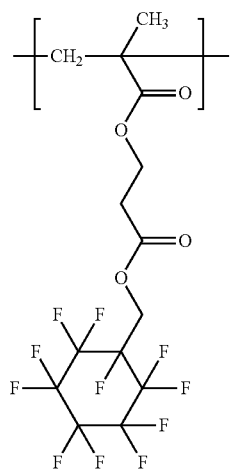

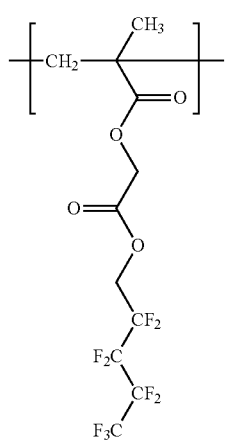 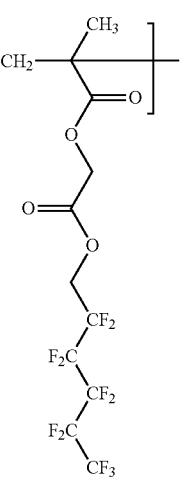

-continued

[chemical structures of four methacrylate-based monomer units with fluorinated side chains]

When Resin (A) has the structural unit (a4), its content is preferably 1 to 20% by mole, more preferably 2 to 15% by mole and still more preferably 3 to 10% by mole based on 100% by mole of all the structural units of the resin.

Other examples of the structural unit(s) include one having an acid-stable hydrocarbon group. The structural unit(s) having an acid-stable hydrocarbon group is sometimes referred to as "structural unit (a5)".

Herein, the term "acid-stable hydrocarbon group" means such a hydrocarbon group that is not removed from the structural unit having the group by action of an acid generated from an acid generator as described above.

The acid-stable hydrocarbon group may be a linear, branched or cyclic hydrocarbon group.

The structural unit which has a hydrocarbon not being removed therefrom by action of an acid may have a linear, branched or cyclic hydrocarbon, preferably an alicyclic hydrocarbon group.

Examples of the structural unit having an acid-stable hydrocarbon group include one represented by formula (a5-1):

[chemical structure of formula (a5-1)] (a5-1)

where $R^{51}$ represents a hydrogen atom or a methyl group;

$R^{52}$ represents a C3-C18 monovalent alicyclic hydrocarbon group which may have a C1-C8 monovalent aliphatic hydrocarbon group as a substituent, provided that the alicyclic hydrocarbon group has no substituent on the carbon atom bonded to $L^{51}$; and $L^{51}$ represents a single bond or a C1-C18 divalent saturated hydrocarbon group where a methylene group can be replaced by an oxygen atom or carbonyl group.

The alicyclic hydrocarbon group represented by $R^{52}$ may be monocyclic or polycyclic one.

Examples of the alicyclic hydrocarbon group include a monocyclic hydrocarbon group such as a C3-C18 cycloalkyl group (e.g. a cyclopropyl group, a cyclobutyl group, a cyclopentyl group, a cyclohexyl group) and a polycyclic alicyclic hydrocarbon group such as an adamantyl group, or a norbornyl group.

Examples of the aliphatic hydrocarbon group include an alkyl groups such as a methyl group, an ethyl group, n-propyl group, isopropyl group, n-butyl group, sec-butyl group, tert-butyl group, a pentyl group, a hexyl group, an octyl group and 2-ethylhexyl group.

Examples of the alicyclic hydrocarbon group having a substituent include a 3-hydroxyadamantyl group, and a 3-methyladamantyl group.

$R^{52}$ is preferably a C3-C18 unsubstituted alicyclic hydrocarbon group, more preferably an adamantyl group, a norbornyl group or a cyclohexyl group.

Examples of the divalent saturated hydrocarbon group represented by $L^{51}$ include divalent aliphatic hydrocarbon groups and divalent alicyclic hydrocarbon groups, preferably divalent aliphatic hydrocarbon groups.

Examples of divalent aliphatic hydrocarbon groups include alkanediyl groups such as a methylene group, an ethylene group, a propanediyl group, a butanediyl group and a pentanediyl group.

The divalent alicyclic hydrocarbon groups may be monocyclic or polycyclic one.

Examples of divalent monocyclic hydrocarbon groups include cycloalkanediyl groups such as a cyclopentanediyl group and a cyclohexanediyl group. Examples of divalent polycyclic alicyclic hydrocarbon groups include an adamantanediyl group and a norbornanediyl group.

Examples of the divalent hydrocarbon group where a methylene group has been replaced by an oxygen atom or carbonyl group include those represented by formulae (L1-1) to (L1-4).

[structure (L1-1)] *—L^{x1}—X^{x1}—L^{x2}—   (L1-1)

[structure (L1-2)] *—L^{x3}—O—L^{x4}—   (L1-2)

-continued

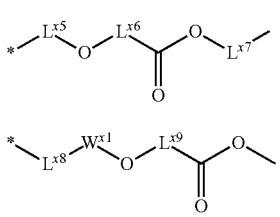
(L1-3)

(L1-4)

In these formulae, * represents a binding position to an oxygen atom.

$X^{x1}$ is a carbonyloxy group or an oxycarbonyl group; and $L^{x1}$ is a C1-C16 divalent aliphatic saturated hydrocarbon group, and $L^{x2}$ is a single bond or a C1-C15 divalent chain or alicyclic hydrocarbon group, provided that the total number of the carbon atoms in $L^{x1}$ and $L^{x2}$ is 16 or less.

$L^{x3}$ is a C1-C17 divalent aliphatic saturated hydrocarbon group, and $L^{x4}$ is a single bond or a C1-C16 divalent chain or alicyclic hydrocarbon group, provided that the total number of the carbon atoms in $L^{x3}$ and $L^{x4}$ is 17 or less.

$L^{x5}$ is a C1-C15 divalent aliphatic saturated hydrocarbon group, and $L^6$ and $L^7$ are a single bond or a C1-C14 divalent chain or alicyclic hydrocarbon group, provided that the total number of the carbon atoms in $L^{x5}$, $L^{x6}$ and $L^{x7}$ is 15 or less.

$L^{x8}$ and $L^{x9}$ are each independently a single bond or a C1-C12 divalent chain or alicyclic hydrocarbon group, and $W^{x1}$ is a C3-C15 divalent cyclic saturated hydrocarbon group, provided that the total number of the carbon atoms in $L^{x8}$, $L^{x9}$ and $W^{x1}$ is 15 or less.

$L^{x1}$ is preferably a C1-C8 divalent aliphatic saturated hydrocarbon group, more preferably a methylene group or an ethylene group.

$L^{x2}$ is preferably a single bond, or a C1-C8 divalent aliphatic saturated hydrocarbon group, more preferably a single bond.

$L^{x3}$ is preferably a C1-C8 divalent aliphatic saturated hydrocarbon group, more preferably a methylene group or an ethylene group.

$L^{x4}$ is preferably a single bond or a C1-C8 divalent aliphatic saturated hydrocarbon group, more preferably a single bond, a methylene group or an ethylene group.

$L^{x5}$ is preferably a C1-C8 divalent aliphatic saturated hydrocarbon group, more preferably a methylene group or an ethylene group.

$L^{x6}$ is preferably a single bond or a C1-C8 divalent aliphatic saturated hydrocarbon group, more preferably a methylene group or an ethylene group.

$L^{x7}$ is preferably a single bond or a C1-C8 divalent aliphatic saturated hydrocarbon group, more preferably a methylene group or an ethylene group.

$L^x$ is preferably a single bond or a C1-C8 divalent aliphatic saturated hydrocarbon group, more preferably a single bond or a methylene group.

$L^{x9}$ is preferably a single bond or a C1-C8 divalent aliphatic saturated hydrocarbon group, more preferably a single bond or a methylene group.

$W^{x1}$ is a preferably C3-C10 divalent cyclic saturated hydrocarbon group, more preferably a cyclohexanediyl group or an adamantanediyl group.

Examples of the group represented by formula (L1-1) include the following ones.

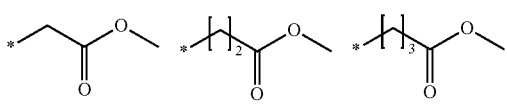

-continued

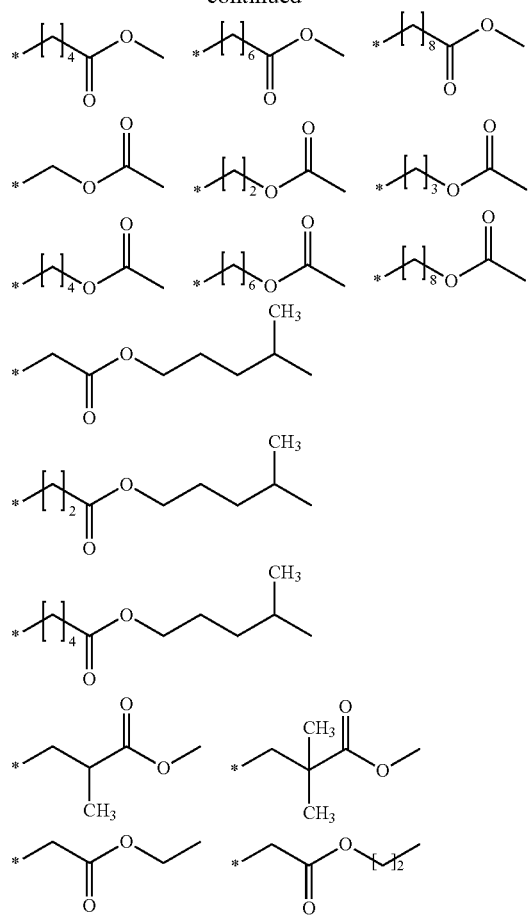

In these formulae, * represents a binding position to an oxygen atom.

Examples of the group represented by formula (L1-2) include the following ones.

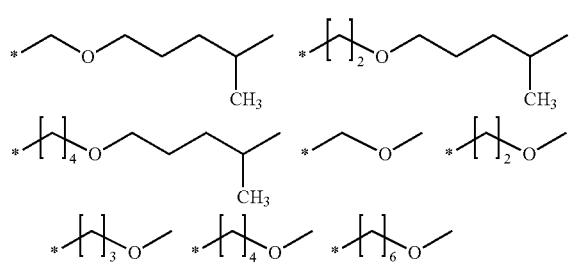

In these formulae, * represents a binding position to an oxygen atom.

Examples of the group represented by formula (L1-3) include the following ones.

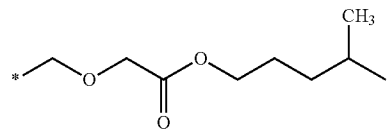

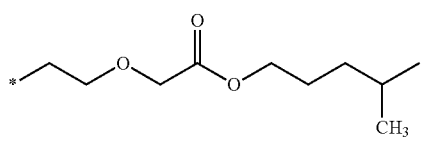

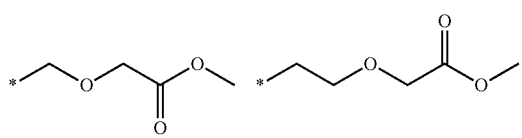

In these formulae, * represents a binding position to an oxygen atom.

Examples of the group represented by formula (L1-4) include the following ones.

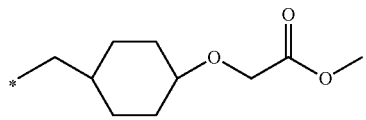

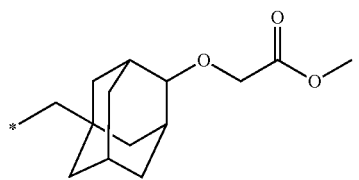

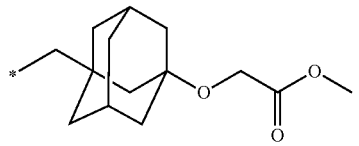

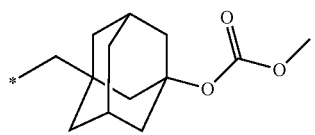

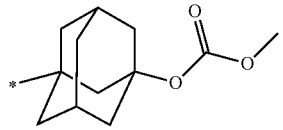

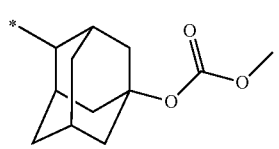

In these formulae, * represents a binding position to an oxygen atom.

$L^{51}$ is preferably a single bond or a group represented by formula (L1-1).

Examples of the structural unit represented by formula (a5-1) include the following ones and those where a methyl group has been replaced by a hydrogen atom in each formula.

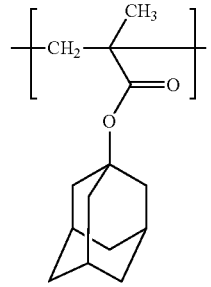
(a5-1-1)

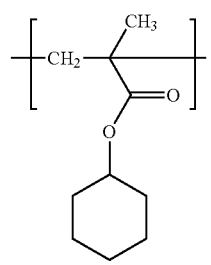
(a5-1-2)

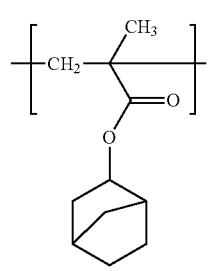
(a5-1-3)

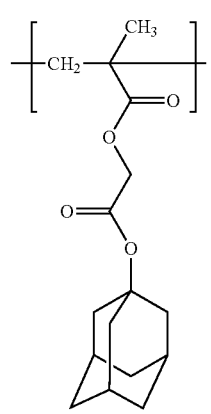
(a5-1-4)

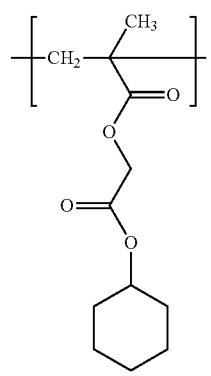
(a5-1-5)

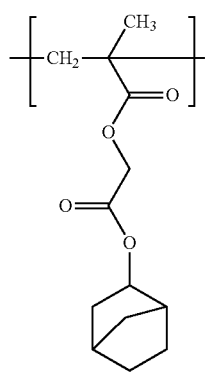 (a5-1-6)
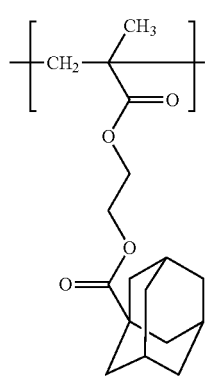 (a5-1-7)
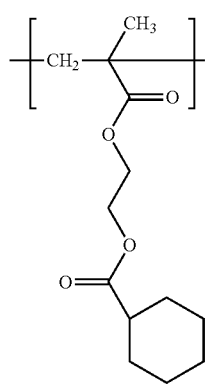 (a5-1-8)
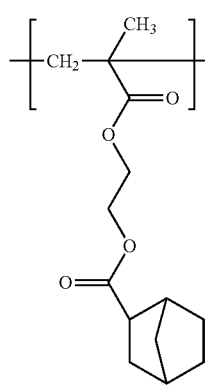 (a5-1-9)
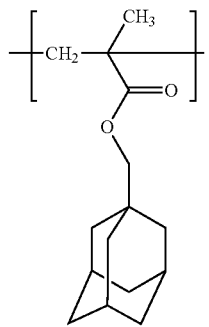 (a5-1-10)
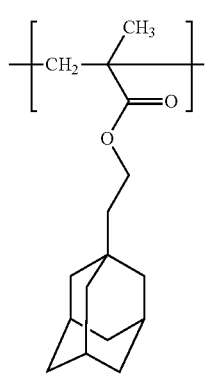 (a5-1-11)
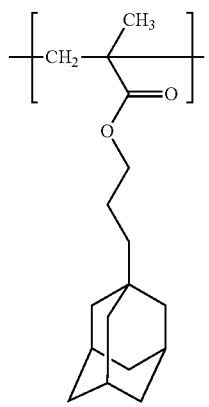 (a5-1-12)
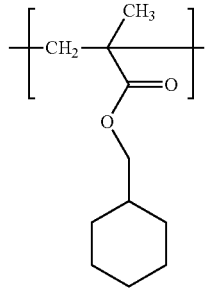 (a5-1-13)

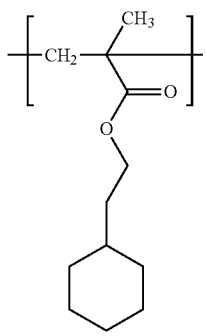
(a5-1-14)

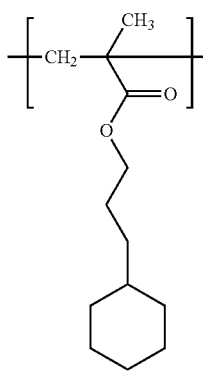
(a5-1-15)

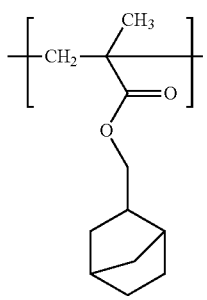
(a5-1-16)

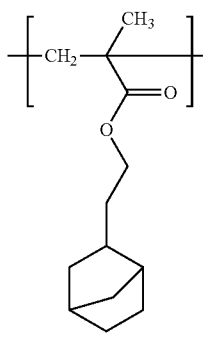
(a5-1-17)

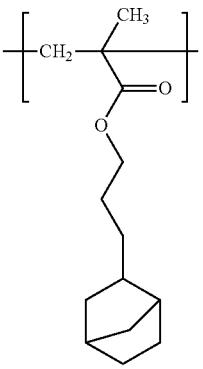
(a5-1-18)

When Resin (A) has the structural unit (a5), its content is preferably 1 to 30% by mole, more preferably 2 to 20% by mole and still more preferably 3 to 15% by mole based on 100% by mole of all the structural units of the resin.

<Structural Unit (II)>

Resin (A) may comprise a structural unit decomposed by irritation to generate an acid. Said structural unit is referred to as "the structural unit (II)". Examples of the structural unit (II) include one as described in JP2016-79235A1.

The structural unit (II) preferably comprises a sulufonate or carboxylate group and an organic cation, or a $S^+$ group and an organic cation at its side chain.

The structural unit (II) which comprises a sulufonate or carboxylate group and an organic cation at its side chain is preferably represented by formula (II-2-A'):

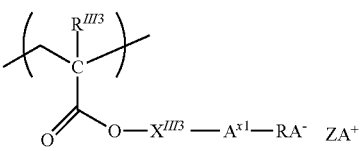
(II-2-A')

wherein $X^{III3}$ represents a C1-C18 divalent saturated hydrocarbon group in which a methylene group can be replaced by —O—, —S— or —CO— and in which a hydrogen atom can be replaced by a fluorine atom, a hydroxyl group or a C1-C6 alkyl group which may have a fluorine atom, $A^{x1}$ represents a C1-C8 alkanediyl group in which a hydrogen atom can be replaced by a fluorine atom or a C1-C6 perfluoroalkyl group, $RA^-$ represents a sulufonate or carboxylate group, $R^{III3}$ represents a hydrogen atom or a C1-C6 alkyl group in which a hydrogen atom can be replaced by a fluorine atom, and $ZA^+$ represents an organic cation.

For $R^{III3}$, examples of the halogen atom include a fluorine atom, a chlorine atom, a bromine atom and an iodine atom.

For $R^{III3}$, examples of a hydroxyl-containing alkyl group include a hydroxymethyl group and a hydroxyethyl group.

For $A^{x1}$, examples of the alkanediyl group include a methylene group, an ethylene group, a propane-1,3-diyl group, a butane-1,4-diyl group, a pentane-1,5-diyl group, a hexane-1,6-diyl group, an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, pentane-1,4-diyl group, and 2-methylbutane-1,4-diyl group.

For $X^{III3}$, examples of divalent aliphatic hydrocarbon groups include a linear alkanediyl group, a branched alkanediyl group, a monocyclic alicyclic hydrocarbon, a polycyclic alicyclic hydrocarbon, and any combinations of these groups, specific examples of which include
a linear alkanediyl group such as a methylene group, an ethylene group, a propane-1,3-diyl group, a propane-1,2-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-12-diyl group;
a branched alkanediyl group such as a butane-1,3-diyl group, a 2-methylpropane-1,3-diyl group, a 2-methylpropane-1,2-diyl group, a pentane-1,4-diyl group, and a 2-methylbutane-1,4-diyl group;
cycloalkanediyl groups such as a cyclobutane-1,3-diyl group, a cyclopentane-1,3-diyl group, a cyclohexane-1,4-diyl group and a cyclooctane-1,5-diyl group; and divalent polycyclic alicyclic hydrocarbon groups such as norbornane-1,4-diyl group, norbornane-2,5-diyl group, adamantane-1,5-diyl group, and adamantane-2,6-diyl group.

Examples of the saturated hydrocarbon group in which a methylene group has been replaced by —O—, —S— or —CO— include divalent groups represented by the formulae (X1) to (X53).

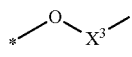
(X1)

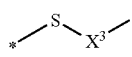
(X2)

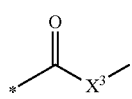
(X3)

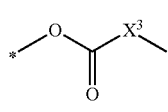
(X4)

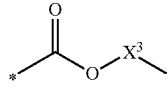
(X5)

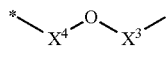
(X6)

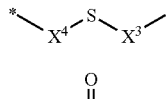
(X7)

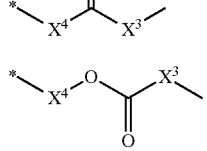
(X8)

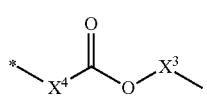
(X9)

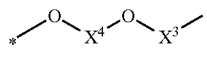
(10)

(X11)

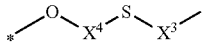
(X12)

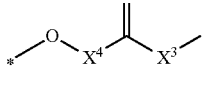
(X13)

(X14)

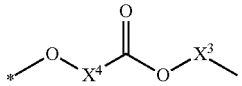
(X15)

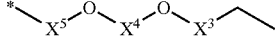
(X16)

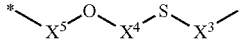
(X17)

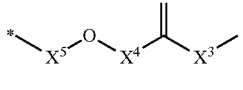
(X18)

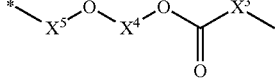
(X19)

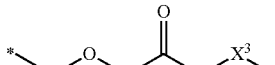
(X20)

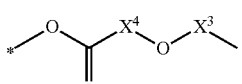
(X21)

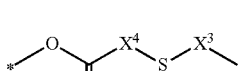
(X22)

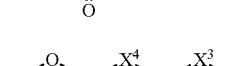
(X23)

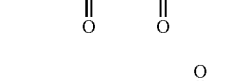
(X24)

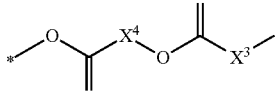
(X25)

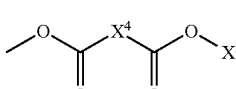
(X26)

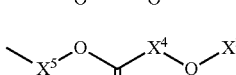
(X27)

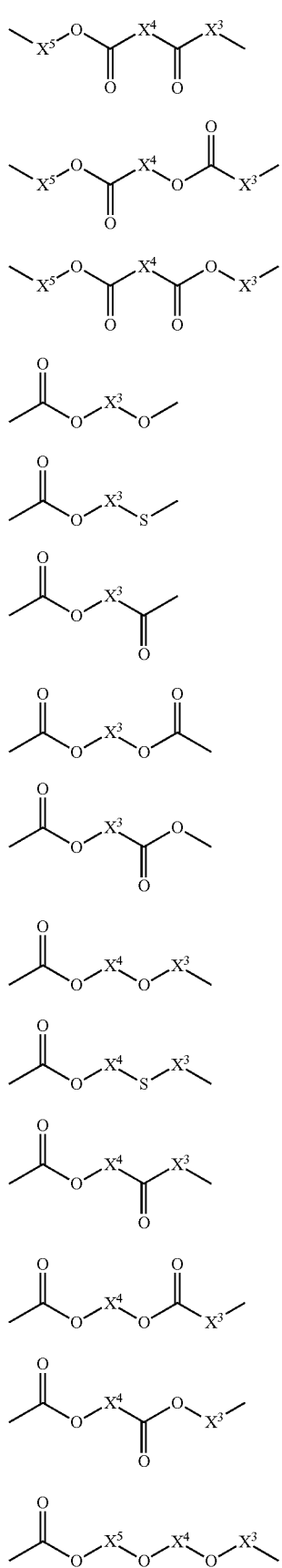
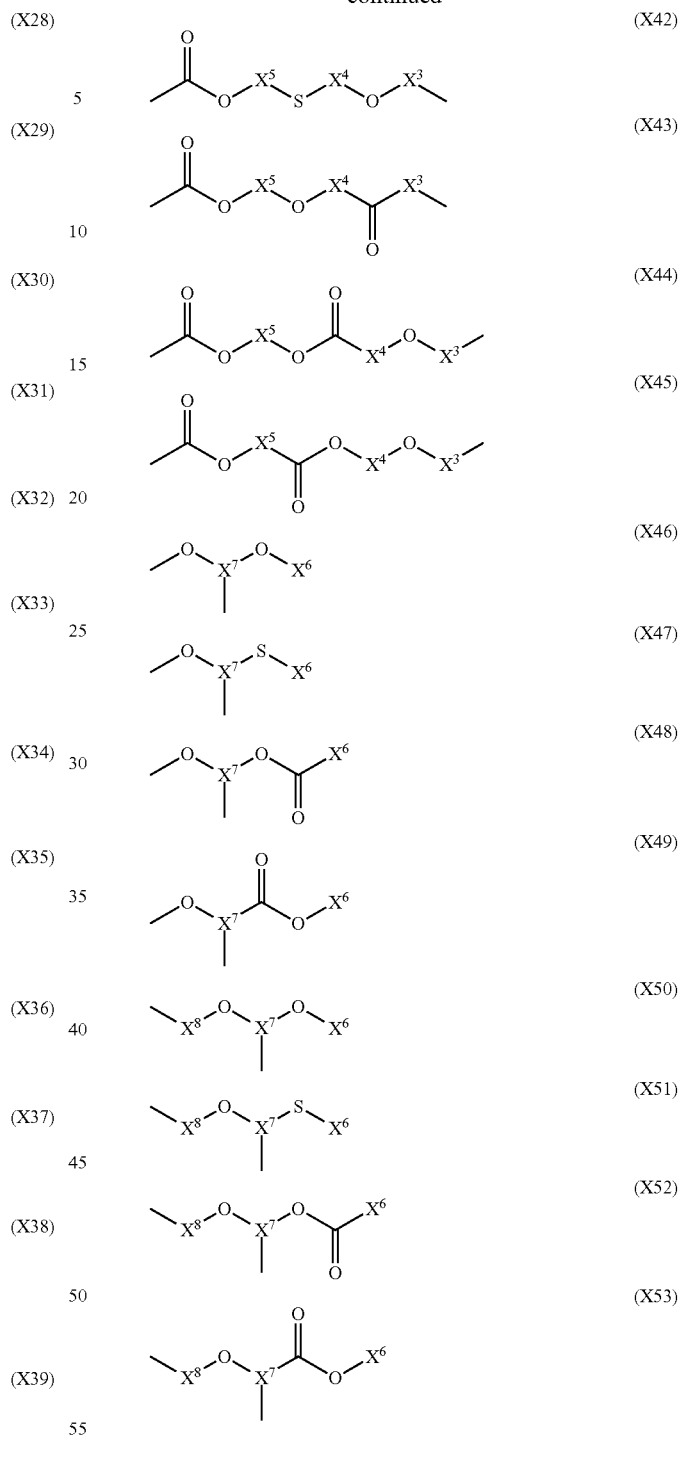

In each formula, $X^3$ represents a C1-C16 divalent hydrocarbon group, $X^4$ represents a C1-C15 divalent hydrocarbon group, $X^5$ represents a C1-C13 divalent hydrocarbon group, $X^6$ represents a C1-C14 divalent hydrocarbon group, $X^7$ represents a C1-C14 divalent hydrocarbon group, and $X^8$ represents a C1-C13 divalent hydrocarbon group and * represents a binding position to $A^{x1}$, provided that each divalent group represented by one of formulae (X1) to (X53) has 1 to 17 carbon atoms in total.

Examples of the organic cation represented by $ZA^+$ include an organic onium cation such as an organic sulfonium cation, an organic iodonium cation, an organic ammonium cation, a benzothiazolium cation and an organic phosphonium cation.

Among them, an organic sulfonium cation and an organic iodonium cation are preferred, and a sulfonium cation, specifically arylsulfonium cation, is more preferred.

The structural unit (II-2-A') is preferably represented by formula (II-2-A):

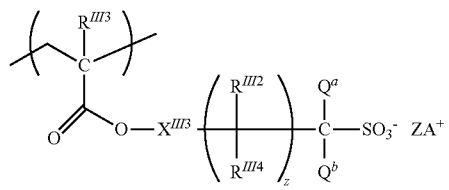
(II-2-A)

wherein $X^{III3}$, $R^{III3}$ and $ZA^+$ are as defined above;
$R^{III2}$ and $R^{III4}$ each independently represent a hydrogen atom, a fluorine atom or a C1-C6 perfluoroalkyl group;
Z represents an integer of 0 to 6; and
$Q^a$ and $Q^b$ each independently represent a fluorine atom or a C1-C6 perfluoroalkyl group.

For $Q^a$, $Q^b$, $R^{III2}$ and $R^{III4}$, examples of a perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferred.

The structural unit (II-2-A) is preferably represented by formula (II-2-A-1):

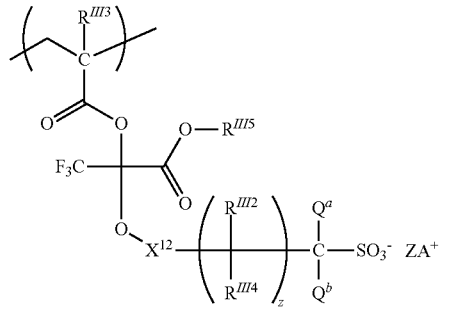
(II-2-A-1)

wherein $R^{III2}$, $R^{III3}$, $R^{III4}$, $R^{III2}$, $Q^a$, $Q^b$, z and $ZA^+$ are as defined above;
$R^{III5}$ represents a C1-C12 saturated hydrocarbon group, and $X^{I2}$ represents a C1-C18 divalent saturated hydrocarbon group in which a methylene group can be replaced by —O—, —S— or —CO— and in which a hydrogen atom can be replaced by a halogen atom or a hydroxyl group.

For $R^{III5}$, examples of the saturated hydrocarbon group include chain alkyl groups such as methyl group, an ethyl group, a propyl group, an isopropyl group, a butyl group, a sec-butyl group, a tert-butyl group, a pentyl group, a hexyl group, a heptyl group, a 2-ethylhexyl group and a dodecyl group.

For $X^{I2}$, examples of the divalent saturated hydrocarbon group include the same examples as the divalent saturated hydrocarbon group for $X^{III3}$.

The structural unit (II-2-A-1) is preferably represented by formula (II-2-A-2):

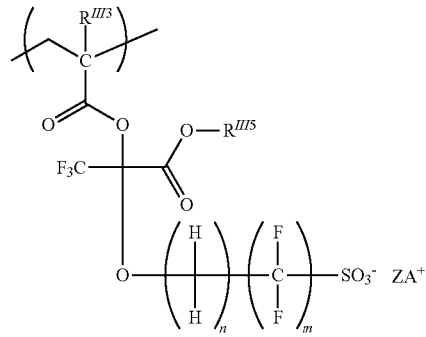
(II-2-A-2)

wherein $R^{III2}$, $R^{III5}$, and $ZA^+$ are as defined above; and
n and m each independently represent 1 or 2.

Examples of the structural unit represented by formula (II-2-A') include the following ones and those recited in WO2012/050015A1.

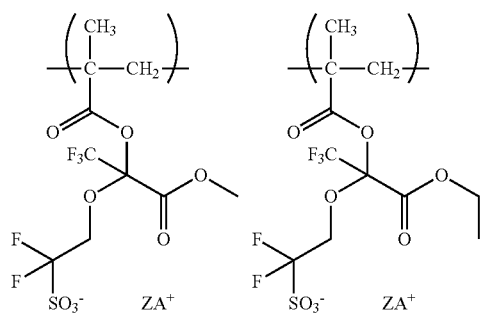

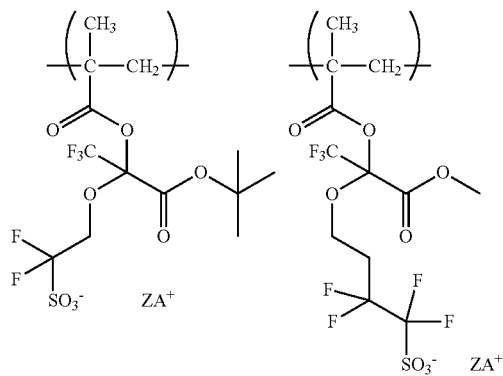

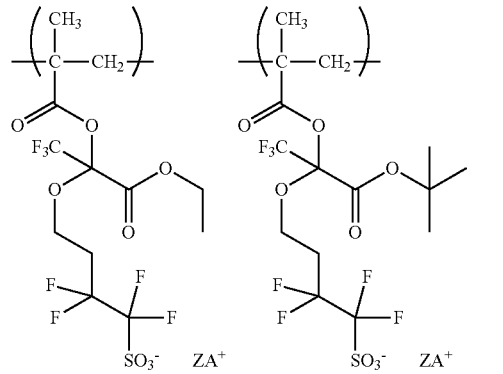

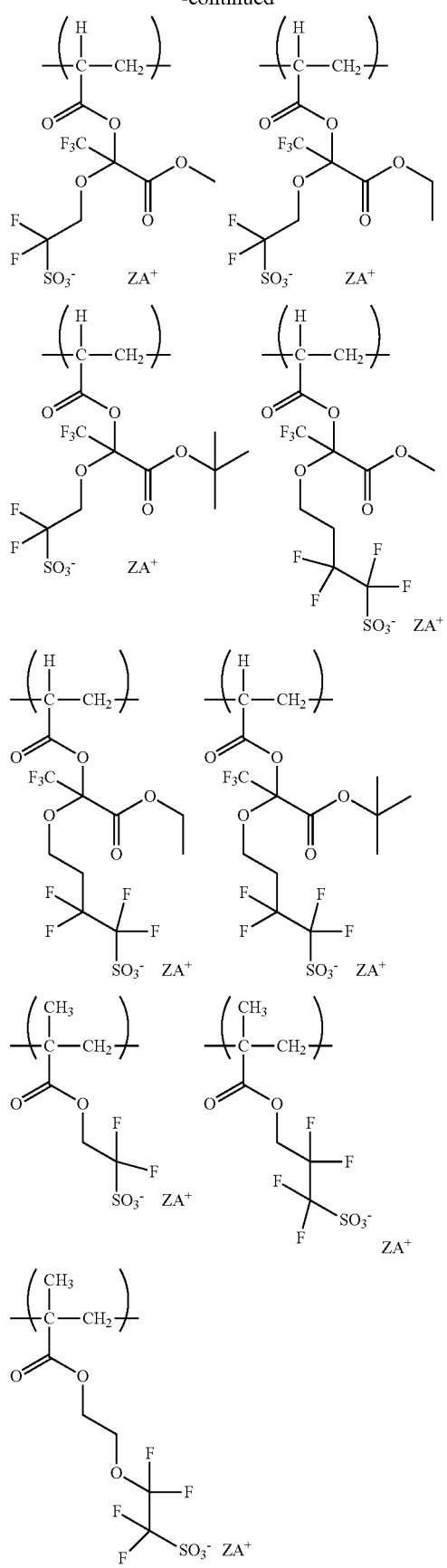
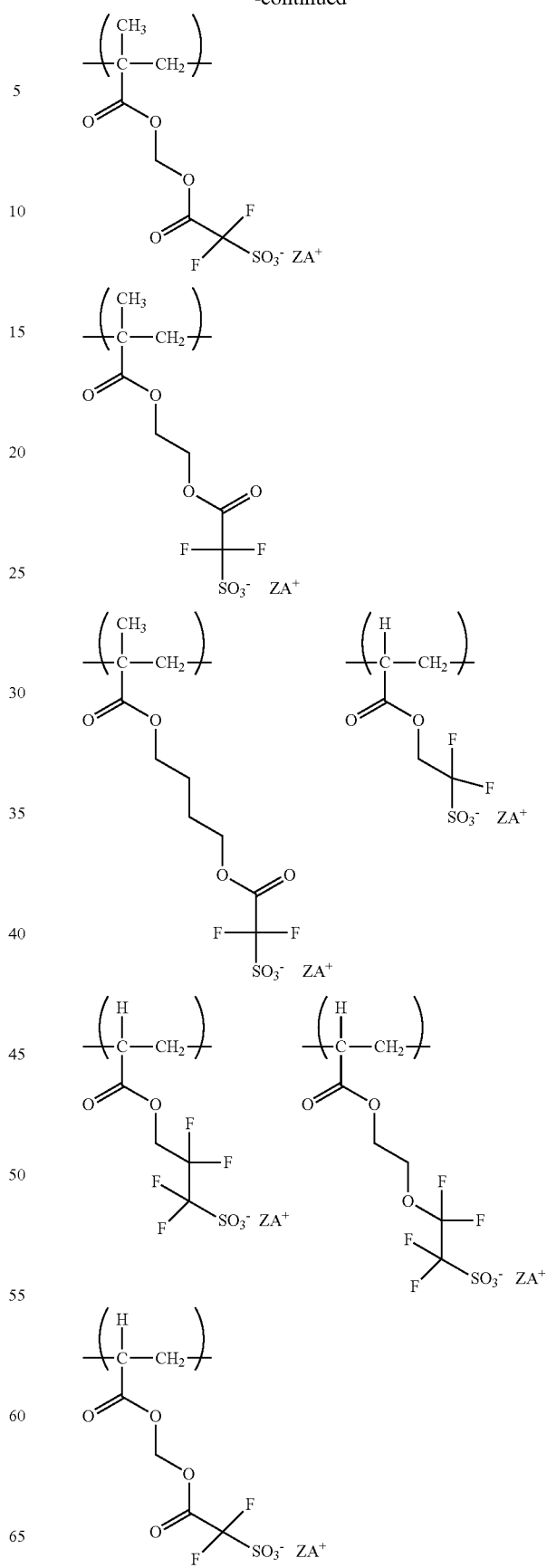

-continued

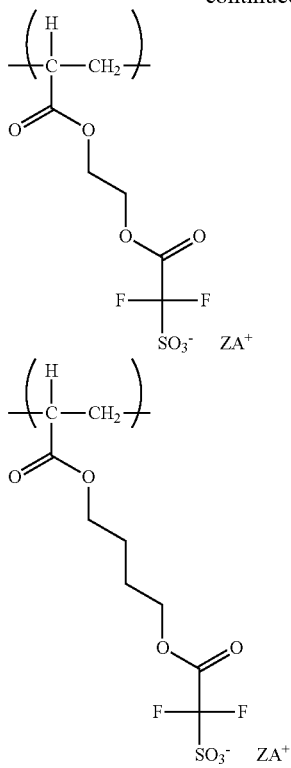

The structural unit (II) which comprises a S⁺ group and an organic cation at its side chain is preferably represented by formula (II-1-1):

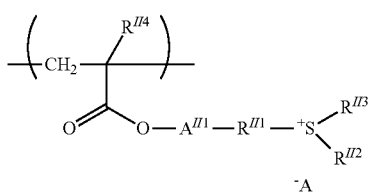

(II-1-1)

wherein $A^{II1}$ represents a single bond or a divalent connecting group,
$R^{II1}$ represents a C6-C18 divalent aromatic hydrocarbon group,
$R^{II2}$ and $R^{II3}$ each independently represent a C1-C18 hydrocarbon group or jointly represents a ring structure together S⁺ bonded thereto,
$R^{II4}$ represents a hydrogen atom, a halogen atom or a C1-C6 alkyl group in which a hydrogen atom can be replaced by a halogen atom, and A⁻ represents an organic cation.

For $R^{II1}$, examples of the aromatic hydrocarbon group include a phenylene group and nathylene group.

For $R^{II2}$ and $R^{II3}$, examples of the hydrocarbon group include the alkyl groups, alicyclic hydrocarbon groups, aromatic hydrocarbon groups and any combination of these groups.

For $R^{II4}$, examples of the halogen atom include a fluorine atom, a chlorine atom, a bromine atom and an iodine atom.

For $R^{II4}$ examples of a hydroxyl-containing alkyl group include a hydroxymethyl group and a hydroxyethyl group.

For $A^{II}$, examples of the divalent connecting group include a C1-C18 divalent saturated hydrocarbon group in which a methylene group can be replaced by —O—, —S— or —CO—. Specific examples of the divalent connecting group include the same saturated hydrocarbon group represented by $X^{III1}$.

Examples of cation of the structural unit represented by formula (II-1-1) include the following ones.

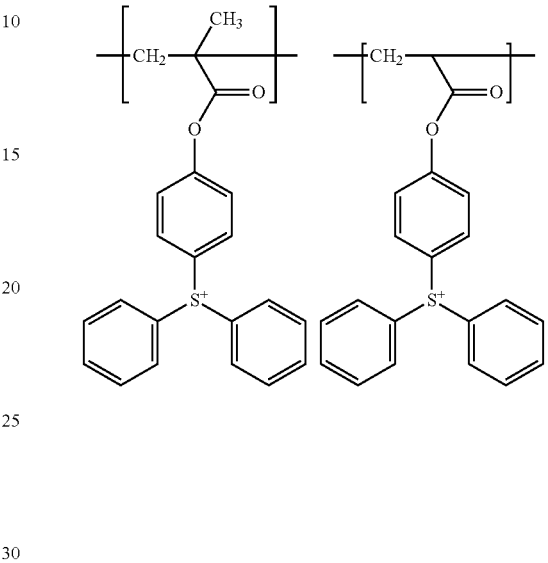

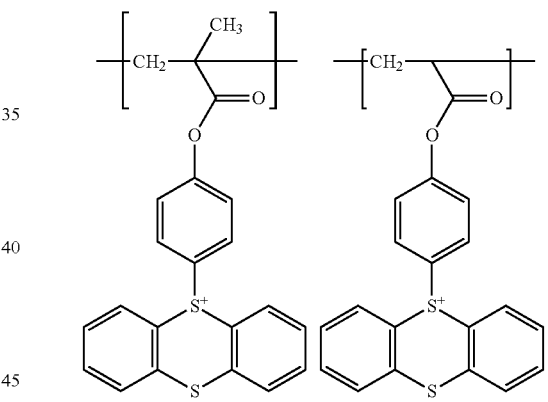

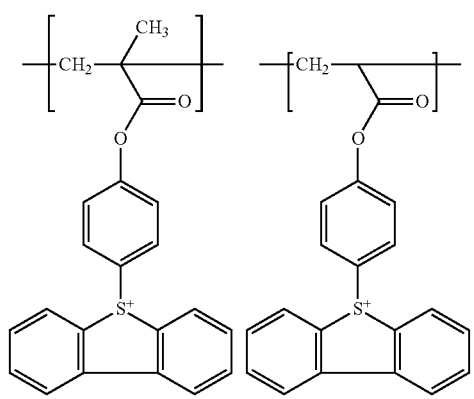

159
-continued
160
-continued
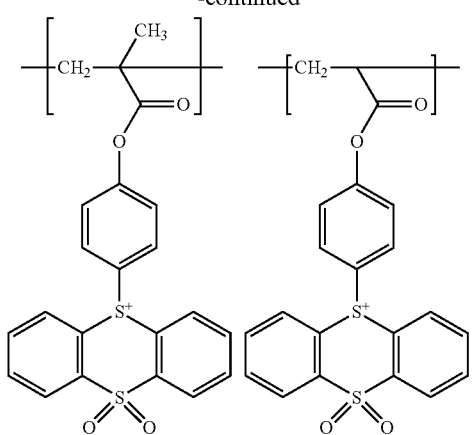
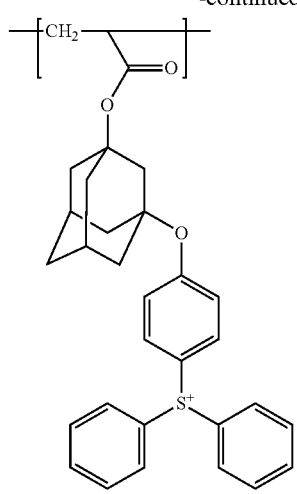
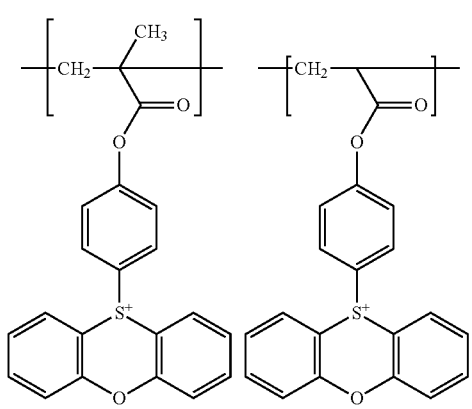
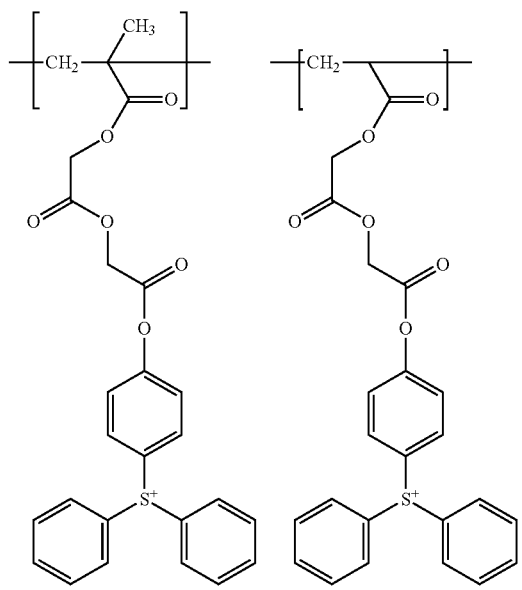
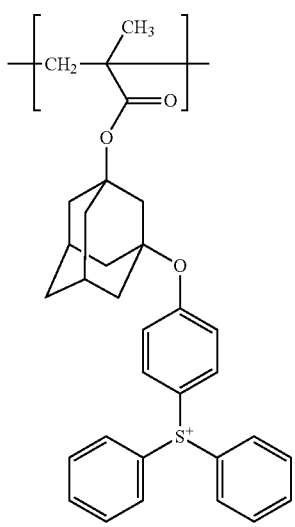
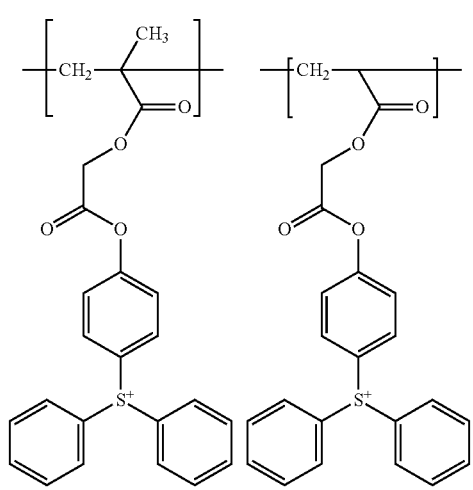

-continued

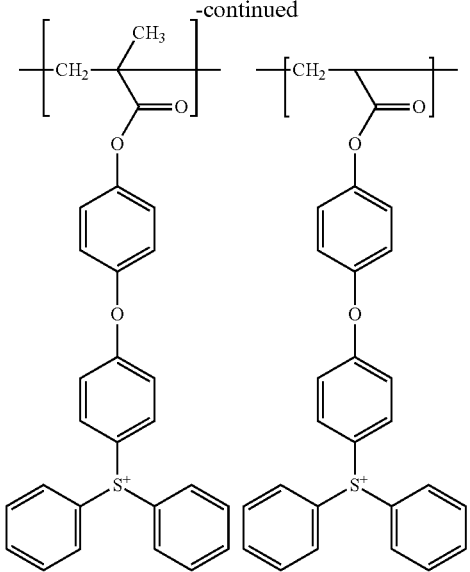

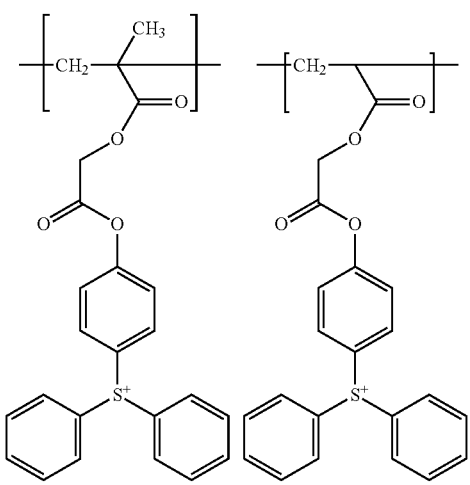

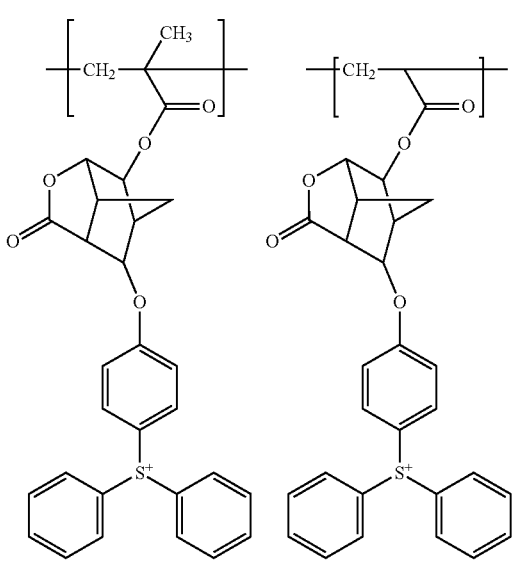

-continued

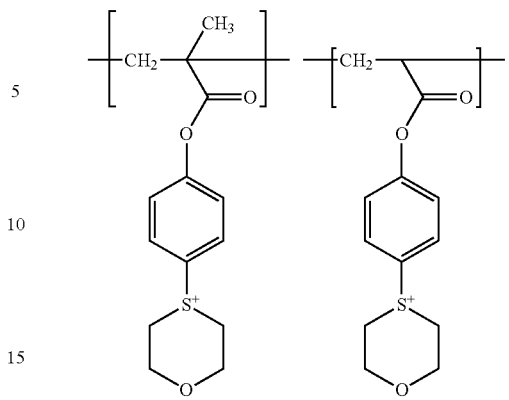

Examples of the organic cation represented by A⁻ include a sulfonate anion, a sulfonylimide anion, a sulfonylmethide anion and a carboxylate anion.

Among them, a sulfonate anion is preferred. For A-, a sulfonate anion is preferably the same one as used for the salt represented by formula (B1).

For A⁻, examples of a sulfonylimide anion include the following ones.

   (I-b-1)

   (I-b-2)

   (I-b-3)

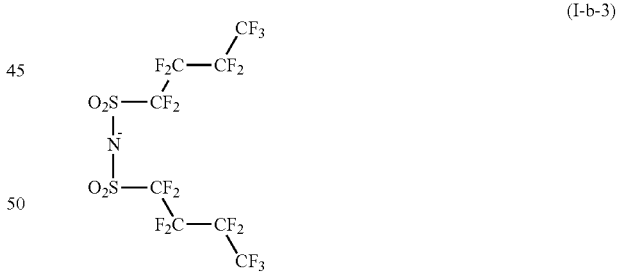

   (I-b-4)

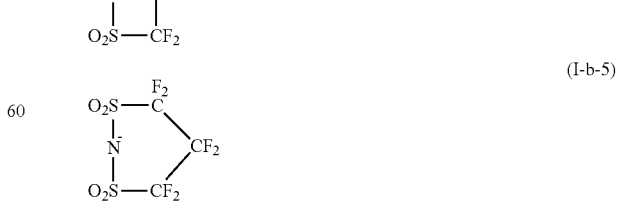   (I-b-5)

For A⁻, examples of a sulfonylmethide anion include the following ones.

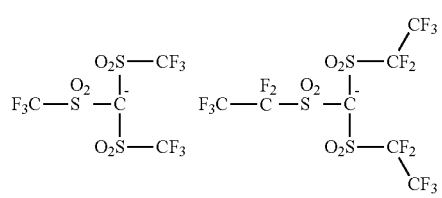
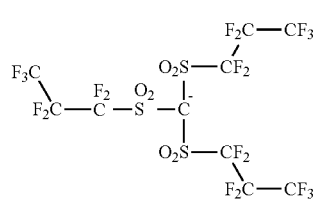
For A⁻, examples of a carbonyloxy anion include the following ones.
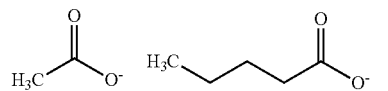
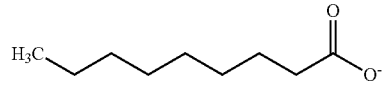
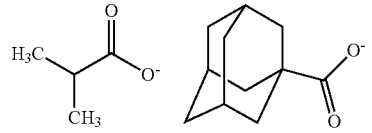
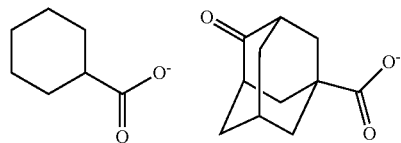
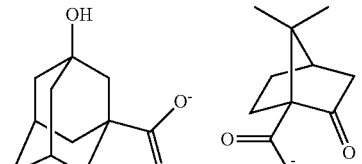
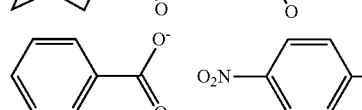
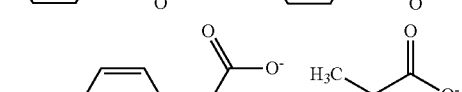
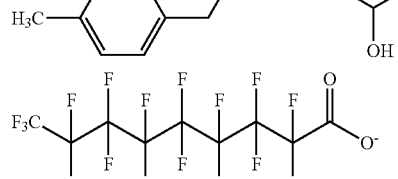
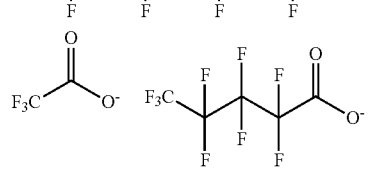
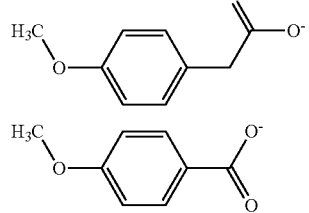
Examples of the structural unit represented by formula (II-1-1) include the following ones.
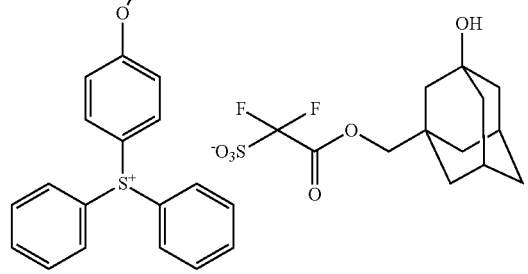
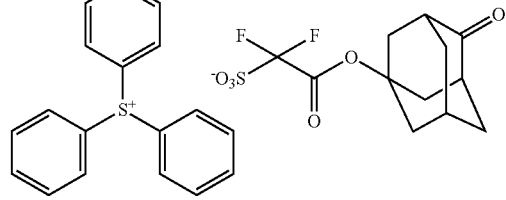
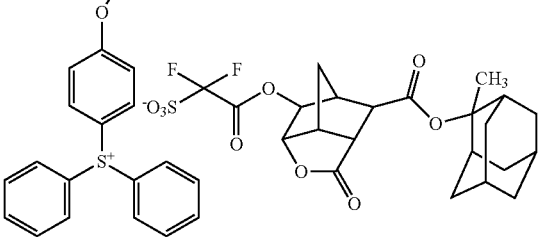

-continued

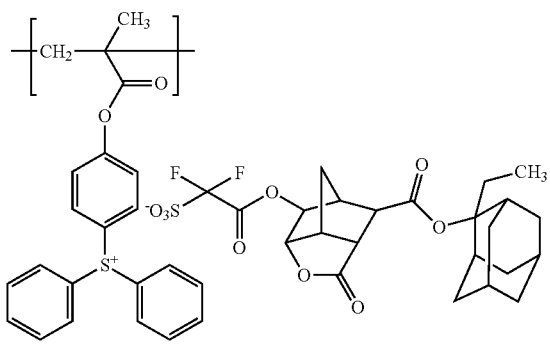

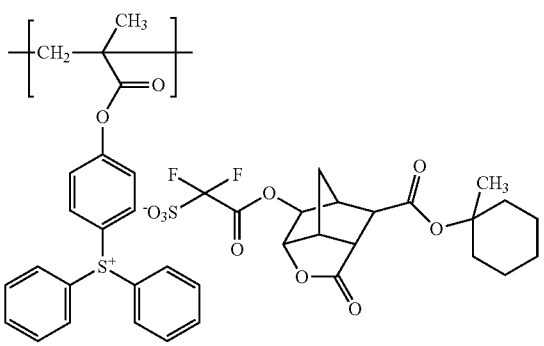

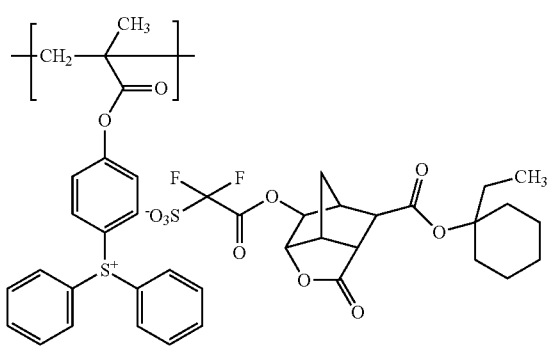

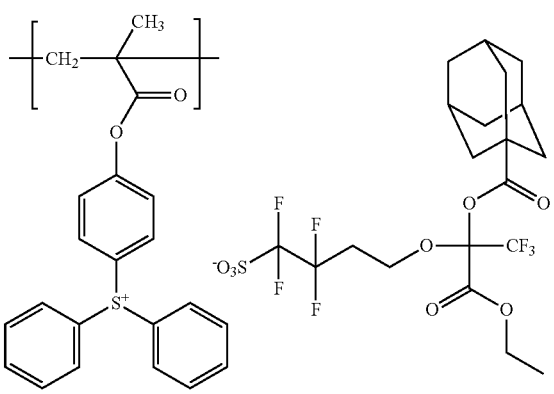

-continued

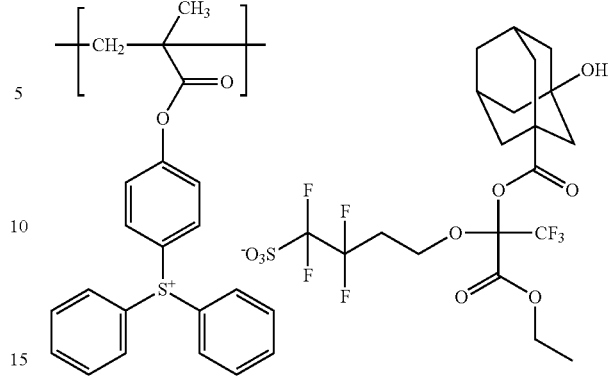

When Resin (A) has the structural unit (II), its content is preferably 1 to 20% by mole, more preferably 2 to 15% by mole, still more preferably 3 to 15% by mole, further still more preferably 3 to 10% by mole, based on 100% by mole of all the structural units of the resin.

Resin (A) has preferably the structural unit (a1) and the structural unit(s).

The structural unit having no acid-labile group is preferably the structural unit (a2) and the structural unit (a3). The structural unit (a2) is preferably the structural unit (a2-1). The structural unit (a3) is preferably the structural unit (a3-1), the structural unit (a3-2) and the structural unit (a3-4).

Resin (A) can be produced according to known polymerization methods such as radical polymerization.

The resin has usually 2,000 or more of the weight-average molecular weight, preferably 2,500 or more of the weight-average molecular weight, more preferably 3,000 or more of the weight-average molecular weight. The resin has usually 50,000 or less of the weight-average molecular weight, preferably more 30,000 or less of the weight-average molecular weight, and preferably more 15,000 or less of the weight-average molecular weight.

The weight-average molecular weight can be measured with gel permeation chromatography.

Examples of another resin than Resin (A) include what consists of structural units having no acid-labile group, preferably what has the structural unit having a fluorine atom such as the structural unit (a4). Here, such another resin is referred to as "Resin (X)".

Resin (X) may be one which consists of the structural unit having a fluorine atom, or one which further comprise the structural unit (a2), the structural unit (a3), the structural unit (a5) or another structural unit having no acid-labile group, known in the art. Resin (X) preferably contains the structural unit having a fluorine atom and the structural unit (a5).

In Resin (X), the content of the structural unit (a4) is preferably 30% by mole or more, more preferably 40% by mole or more, still more preferably 45% by mole or more based on sum of the structural units in the resin.

Resin (X) usually has 6000 or more of the weight-average molecular weight, preferably 7000 or more of the weight-average molecular weight. The resin usually has 80,000 or less of the weight-average molecular weight, preferably has 60,000 or less of the weight-average molecular weight.

The weight-average molecular weight can be measured with known methods such as liquid chromatography or gas chromatography.

When the photoresist composition contains Resin (X), the content of the resin is preferably 1 to 60 weight parts, more preferably 2 to 50 weight parts, and still more preferably 2 to 40 weight parts, further more preferably 1 to 30 weight parts, further still more preferably 1 to 8 weight parts, relative to 100 parts of Resin (A).

The total content of the resins in the photoresist composition of the present invention is usually 80% by mass or more, preferably 90% by mass or more, based on sum of solid component, and usually 99% by mass or less based on sum of solid component.

In this specification, "solid component" means components other than solvent in the photoresist composition.

The resin can be obtained by conducting polymerization reaction of the corresponding monomer or monomers. The polymerization reaction is usually carried out in the presence of a radical initiator.

This polymerization reaction can be conducted according to known methods.

<Solvent>

Preferably, the photoresist composition of the disclosure further contains a solvent.

The amount of the solvent is usually 90% by weight or more, preferably 92% by weight or more preferably 94% by weight or more based on total amount of the photoresist composition of the present invention.

The amount of the solvent is usually 99.9% by weight or less and preferably 99% by weight or less based on total amount of the photoresist composition of the present invention. The content can be measured with known methods such as liquid chromatography or gas chromatography.

Examples of the solvent include a glycol ether ester such as ethyl cellosolve acetate, methyl cellosolve acetate and propylene glycol monomethyl ether acetate; a glycol ether such as propylene glycol monomethyl ether; an ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

<Quencher>

The photoresist composition of the disclosure may further contain a quencher such as a basic compound. The "quencher" has the property that it can trap an acid, especially an acid generated from the acid generator by exposure to light for lithography.

Examples of the quencher include a basic compound, such as a basic nitrogen-containing organic compound, and a salt which generates an acid having acidity weaker than an acid generated from the acid generators.

Examples of the basic nitrogen-containing organic compound include an amine compound such as an aliphatic amine, an aromatic amine and an ammonium salt. Examples of the aliphatic amine include a primary amine, a secondary amine and a tertiary amine. Examples of the aromatic amine include an aromatic amine.

Examples of the quencher include 1-naphthylamine, 2-naphthylamine, aniline, diisopropylaniline, 2-,3- or 4-methylaniline, 4-nitroaniline, N-methylaniline, N,N-dimethylaniline, diphenylamine, hexylamine, heptylamine, octylamine, nonylamine, decylamine, dibutylamine, pentylamine, dioctylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, 2 tris [2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenyl methane, piperazine, morpholine, piperidine, hindered amine compound having a piperidine structure, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl) ethene, 1,2-di(4-pyridyl)ethene, 1,3-di(4-pyridyl) propane, 1,2-di(4-pyridyloxy) ethane, di(2-pyridyl) ketone, 4,4'-dipyridyl sulfide, 4,4'-dipyridyl disulfide, 2,2'-dipyridylamine, 2,2'-dipicolylamine and bipyridine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

As to salt which generates an acid having acidity weaker than an acid generated from the acid generators, the acidity in the salts is shown by the acid dissociation constant (pKa).

The acid dissociation constant of acid generated from the salt for a quencher is usually a salt of $-3<$pKa.

The salt for a quencher is preferably a salt of $-1<$pKa$<7$, and more preferably a salt of $0<$pKa$<5$.

Specific examples of the salt for a quencher include the following ones, an onium carboxylic acid salt such as the salt of formula (D), and salts recited in US2012/328986A1, US2011/171576A1, US2011/201823A1, JP2011-39502A1, and US2011/200935A1.

The photoresist composition comprises preferably onium carboxylic acid salt, more preferably the salt of formula (D).

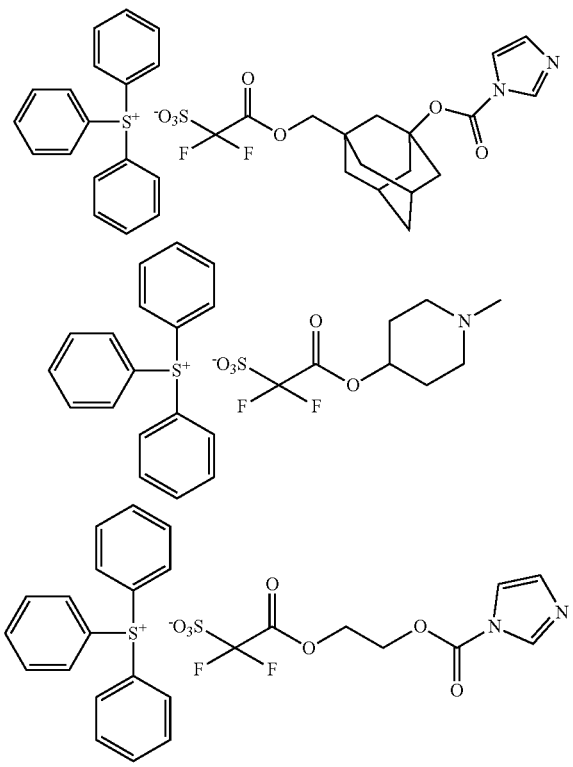

-continued

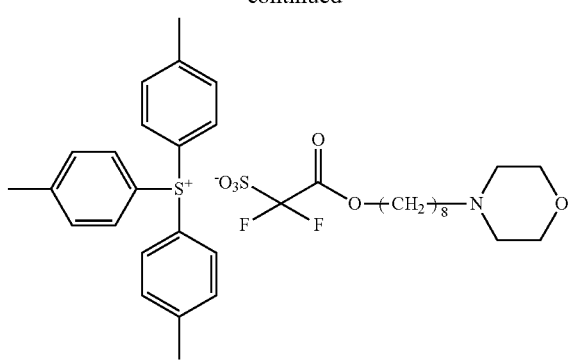

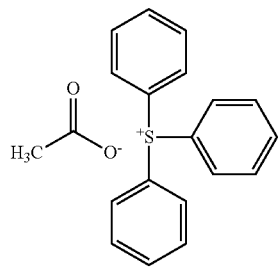

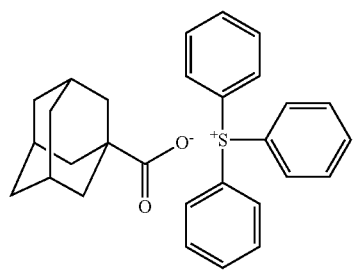

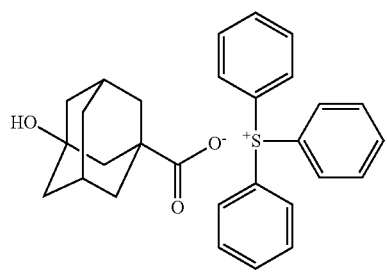

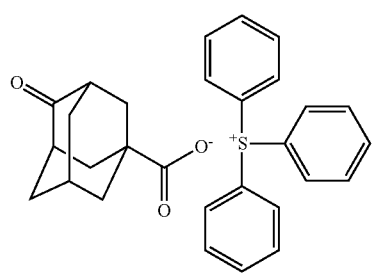

-continued

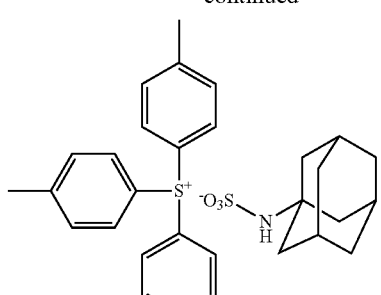

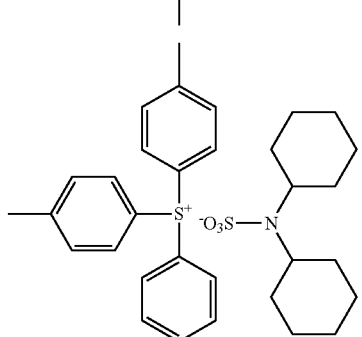

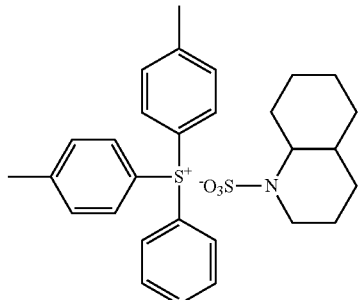

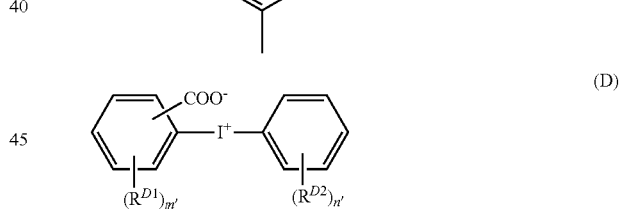

(D)

In formula (D), $R^{D1}$ and $R^{D2}$ respectively represent a C1-C12 monovalent hydrocarbon group, a C1-C6 alkoxy group, a C2-C7 acyl group, a C2-C7 acyloxy group, a C2-C7 alkoxycarbonyl group, a nitro group or a halogen atom. The symbols m' and n' each independently represent an integer of 0 to 4, preferably an integer of 0 to 2, more preferably 0.

Examples of the compounds of formula (D) include the following ones.

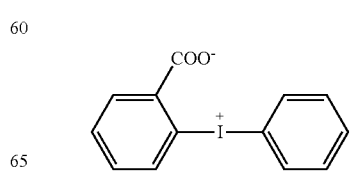

-continued

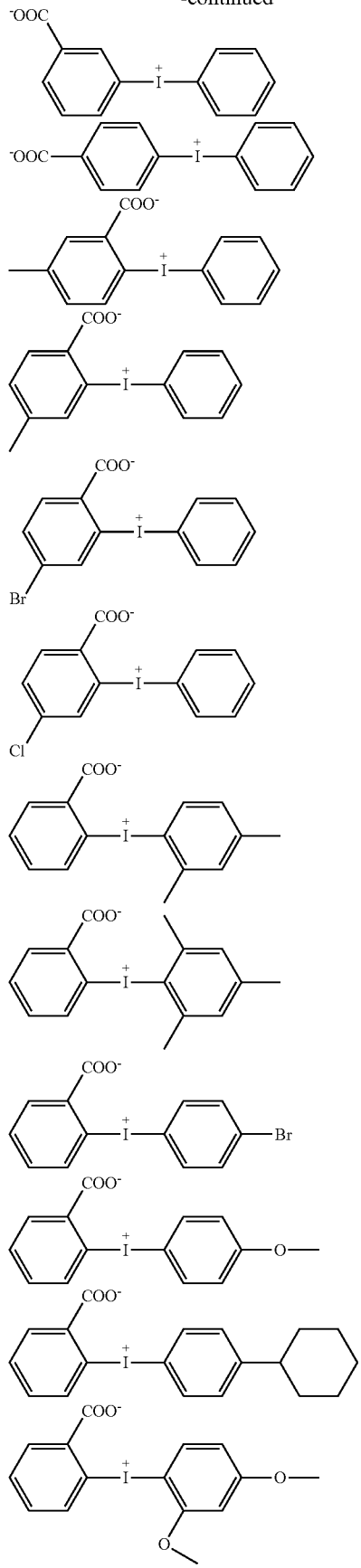

-continued

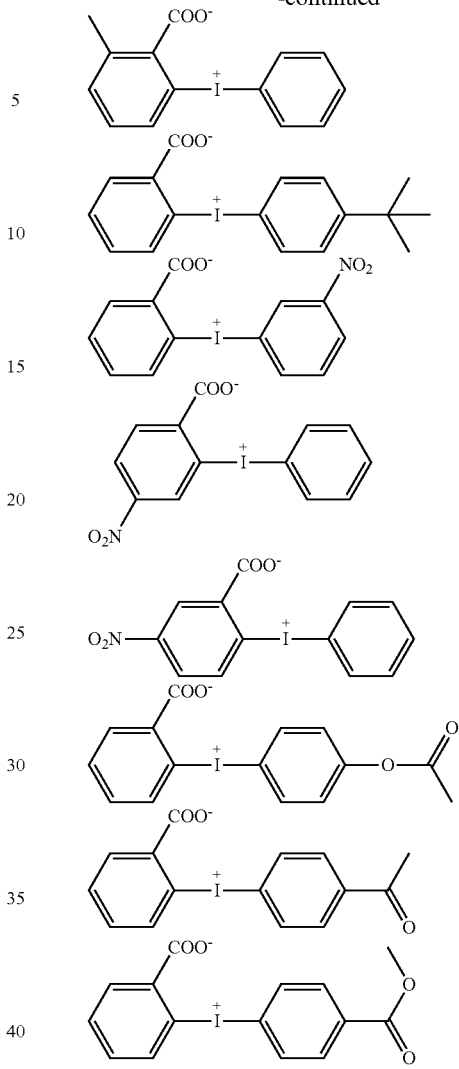

The content of quencher is preferably 0.01 to 5% by mass, more preferably 0.01 to 4% by mass, still more preferably 0.01 to 3% by mass, and further more preferably 0.01 to 1% by mass, based on sum of solid component.

The photoresist compositions of the present invention may comprise, if necessary, a small amount of various additives such as a sensitizer, a dissolution inhibitor, other polymers, a surfactant, a stabilizer and a dye as long as the effect of the present invention is not prevented.

The photoresist compositions of the present invention can be prepared by mixing, usually in a solvent, an acid generator which contains the salt (I) and Resin (A), and if necessary a quencher, and/or additives at a suitable ratio for the composition, optionally followed by filtrating the mixture with a filter having 0.003 µm to 0.2 µm of a pore size.

The order of mixing these components is not limited to any specific order. The temperature at mixing the components is usually 10 to 40° C., which can be selected in view of the resin or the like. The mixing time is usually 0.5 to 24 hours, which can be selected in view of the temperature. The means for mixing the components is not limited to specific one. The components can be mixed by being stirred.

The amounts of the components in the photoresist compositions can be adjusted by selecting the amount to be used for production of them.

The photoresist compositions of the present invention are useful for a chemically amplified photoresist composition.

The photoresist compositions of the disclosure are useful for a chemically amplified photoresist composition.

A photoresist pattern can be produced by the following steps (1) to (5):

(1) a step of applying the photoresist composition of the present invention on a substrate, (2) a step of forming a composition film by conducting drying, (3) a step of exposing the composition film to radiation, (4) a step of baking the exposed composition film, and (5) a step of developing the baked composition film with an alkaline developer.

The applying of the photoresist composition on a substrate is usually conducted using a conventional apparatus such as spin coater. Examples of the substrate include a silicon wafer or a quartz wafer on which a sensor, a circuit, a transistor or the like is formed.

The formation of the composition film is usually conducted using a heating apparatus such as hot plate or a decompressor, and the heating temperature is usually 50 to 200° C. When the pressure is reduced during heating, the operation pressure is usually 1 to $1.0*10^5$ Pa. The heating time is usually 10 to 180 seconds.

The composition film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), a light source radiating harmonic laser light in a far UV region or a vacuum UV region by wavelength conversion of laser light from a solid laser light source (such as YAG or semiconductor laser), and a light source radiating electron beam or EUV (extreme ultraviolet) light.

The temperature of baking of the exposed composition film is usually 50 to 200° C., and preferably 70 to 150° C.

The development of the baked composition film is usually carried out using a development apparatus. The development method includes dipping methods, paddle methods, spray methods and dynamic dispense method. The developing temperature is preferably 5 to 60° C., and the developing time is preferably 5 to 300 seconds.

The positive and negative type photoresist patterns can be obtained by the development depending on a developer to be used therefor.

When a positive type photoresist pattern is prepared from the photoresist composition of the present invention, the development can be conducted with an alkaline developer. The alkaline developer to be used may be any one of various alkaline aqueous solution used in the art. Generally, an aqueous solution of tetramethylammonium hydroxide or (2-hydroxyethyl)trimethylammonium hydroxide (commonly known as "choline") is often used. The alkaline developer may comprise a surfactant.

After development, the photoresist film having photoresist pattern is preferably washed with ultrapure water, and the remained water on the photoresist film and the substrate is preferably removed therefrom.

When a negative type photoresist pattern is prepared from the photoresist composition of the present invention, the development can be conducted with a developer containing an organic solvent, such developer is sometimes referred to as "organic developer".

Examples of an organic solvent for organic developer include ketone solvents such as 2-hexanone, 2-heptanone; glycolether ester solvents such as propyleneglycolmonomethylether acetate; ester solvents such as butyl acetate; glycolether solvents such as propyleneglycolmonomethylether; amide solvents such as N,N-dimethylacetamide; and aromatic hydrocarbon solvents such as anisole.

The content of organic solvent is preferably from 90% to 100% by weight, more preferably from 95% to 100% by weight, in an organic developer. Preferred is that the organic developer essentially consists of an organic solvent.

Among them, the organic developer is preferably a developer comprising butyl acetate and/or 2-heptanone.

The total content of butyl acetate and 2-heptanone is preferably from 90% to 100% by weight, more preferably from 95% to 100% by weight. Preferred is that the organic developer essentially consists of butyl acetate and/or 2-heptanone.

The organic developer may comprise a surfactant or a very small amount of water.

Development with an organic developer can be stopped by replacing the developer by other solvent than it such as alcohol.

The photoresist composition of the present invention is suitable for KrF excimer laser lithography, ArF excimer laser lithography, EUV (extreme ultraviolet) lithography, EUV immersion lithography and EB (electron beam) lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted.

The weight-average molecular weight of any material used in the following examples is a value found by gel permeation chromatography under the following conditions.

Column: HLC-8120GPC Type (Three Columns with guard column), TSKgel Multipore HXL-M, manufactured by TOSOH CORPORATION Solvent: Tetrahydrofuran, Flow rate: 1.0 mL/min.

Detector: RI detector

Column temperature: 40° C.

Injection volume: 100 μL

Standard reference material: Standard polystyrene

Structures of compounds were determined by NMR (GX-270 Type or EX-270 Type, manufactured by JEOL LTD.) and mass spectrometry (Liquid Chromatography: 1100 Type, manufactured by AGILENT TECHNOLOGIES LTD., Mass Spectrometry: LC/MSD Type or LC/MSD TOF Type, manufactured by AGILENT TECHNOLOGIES LTD.).

Example 1

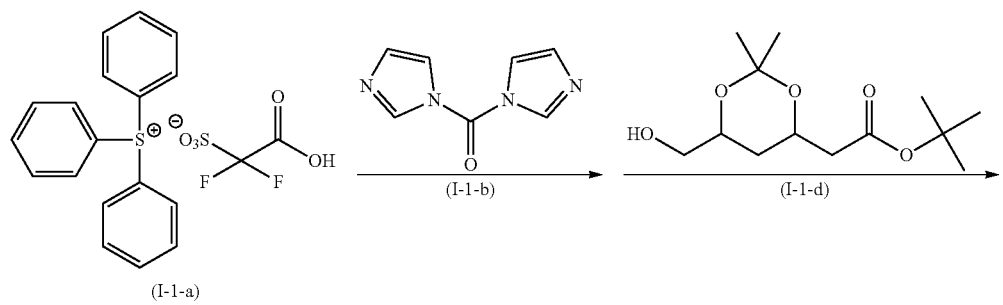

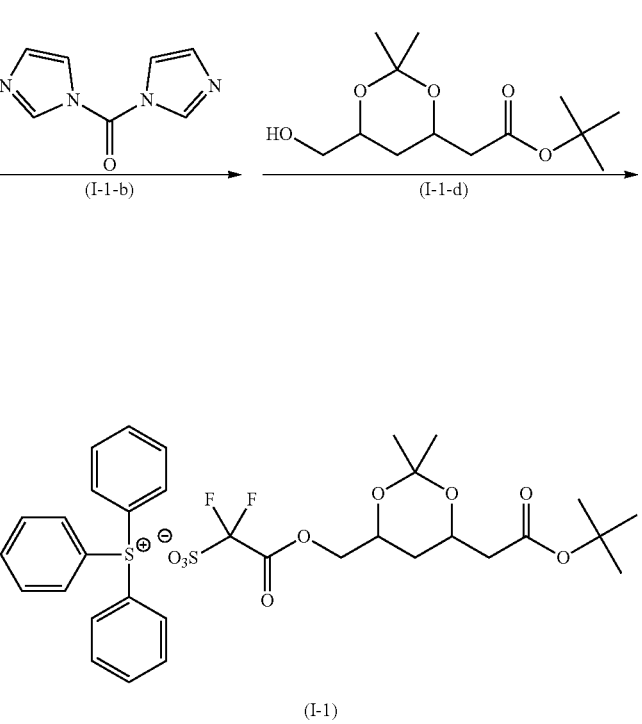

In a reactor, 35 parts of the salt represented by the formula (I-1-a) and 175 parts of chloroform were mixed and stirred at 23° C. for 30 minutes. To the obtained mixture, 13.59 parts of carbonyldiimidazole was added and then stirred at 60° C. for one hour. The obtained reaction mixture was cooled to 23° C. and then a mixture of 24.94 parts of the compound represented by the formula (I-1-d) and 50 parts of chloroform was added thereto, followed by being stirred at 23° C. for two hours.

To the reaction mixture, 450 parts of chloroform and 150 parts of ion-exchanged water were added and then stirred at 23° C. for 30 minutes. Then the obtained organic layer was collected therefrom.

To the collected organic layer, 100 parts of 5% aqueous oxalic acid solution was added and then stirred at 23° C. for 30 minutes for washing, followed by separating into an organic layer. The organic layer was washed five times as mentioned above.

Then the resultant mixture was concentrated. To the obtained residue, 37.5 parts of acetonitrile and 115 parts of tert-butylmethylether were added and the resultant mixture was stirred at 23° C. for 30 minutes, and then its supernatant was removed therefrom. The obtained residue was dissolved in acetonitrile and then concentrated to obtain 25.73 parts of the salt represented by formula (I-1).

MS (ESI(+), spectrum): $M^+$ 263.1
MS (ESI(−), spectrum): $M^-$ 417.1

Examples 2

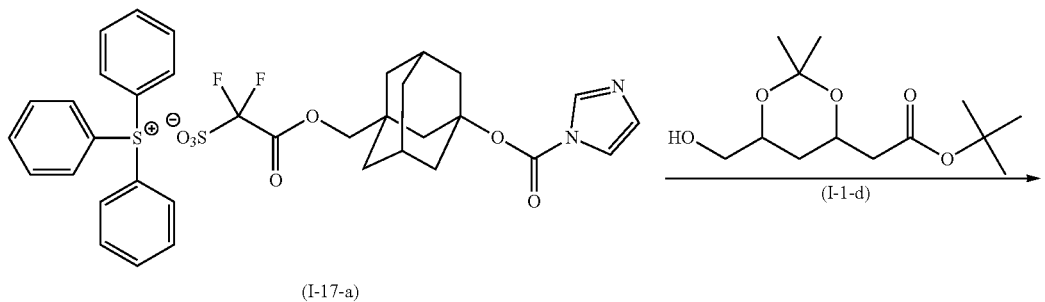

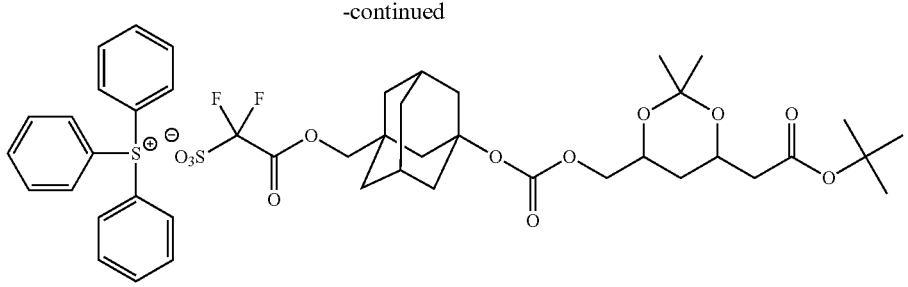

(I-17)

In a reactor, 9.54 parts of the salt represented by the formula (I-17-a) and 30 parts of chloroform were mixed and stirred at 23° C. for 30 minutes. To the obtained mixture, a mixture of 3.57 parts of the compound represented by the formula (I-1-d) and 10 parts of chloroform was added thereto, followed by being stirred at 23° C. for 8 hours.

To the reaction mixture, 30 parts of ion-exchanged water were added and then stirred at 23° C. for 30 minutes. Then the obtained organic layer was collected therefrom. To the collected organic layer, 20 parts of 5% aqueous oxalic acid solution was added and then stirred at 23° C. for 30 minutes, followed by separating into an organic layer. To the collected organic layer, 30 parts of ion-exchanged water was added and then stirred at 23° C. for 30 minutes for washing, followed by separating into an organic layer. The organic layer was washed five times as mentioned above.

Then the resultant mixture was concentrated. To the obtained residue, 30 parts of tert-butylmethylether was added and the resultant mixture was stirred at 23° C. for 30 minutes, and then its supernatant was removed therefrom. The obtained residue was concentrated to obtain 10.25 parts of the salt represented by formula (I-17).

MS (ESI(+), spectrum): M$^+$263.1
MS (ESI(−), spectrum): M$^-$ 625.2

In a reactor, 6.17 parts of the salt represented by the formula (I-2-a), 1.7 parts of carbonyldiimidazole and 30 parts of chloroform were mixed and stirred at 23° C. for 8 hours.

To the obtained mixture, a mixture of 2.6 parts of the compound represented by the formula (I-1-d) and 10 parts of chloroform was added thereto, followed by being stirred at 23° C. for 8 hours.

To the reaction mixture, 30 parts of ion-exchanged water were added and then stirred at 23° C. for 30 minutes. Then the obtained organic layer was collected therefrom.

To the collected organic layer, 20 parts of 5% aqueous oxalic acid solution was added and then stirred at 23° C. for 30 minutes, followed by separating into an organic layer.

To the collected organic layer, 30 parts of ion-exchanged water was added and then stirred at 23° C. for 30 minutes for washing, followed by separating into an organic layer. The organic layer was washed five times as mentioned above.

Then the resultant mixture was concentrated. To the obtained residue, 30 parts of tert-butylmethylether was added and the resultant mixture was stirred at 23° C. for 30 minutes, and then its supernatant was removed therefrom. The obtained residue was concentrated to obtain 6.45 parts of the salt represented by formula (I-2).

MS (ESI(+), spectrum): M$^+$263.1
MS (ESI(−), spectrum): M$^-$ 595.2

Example 3

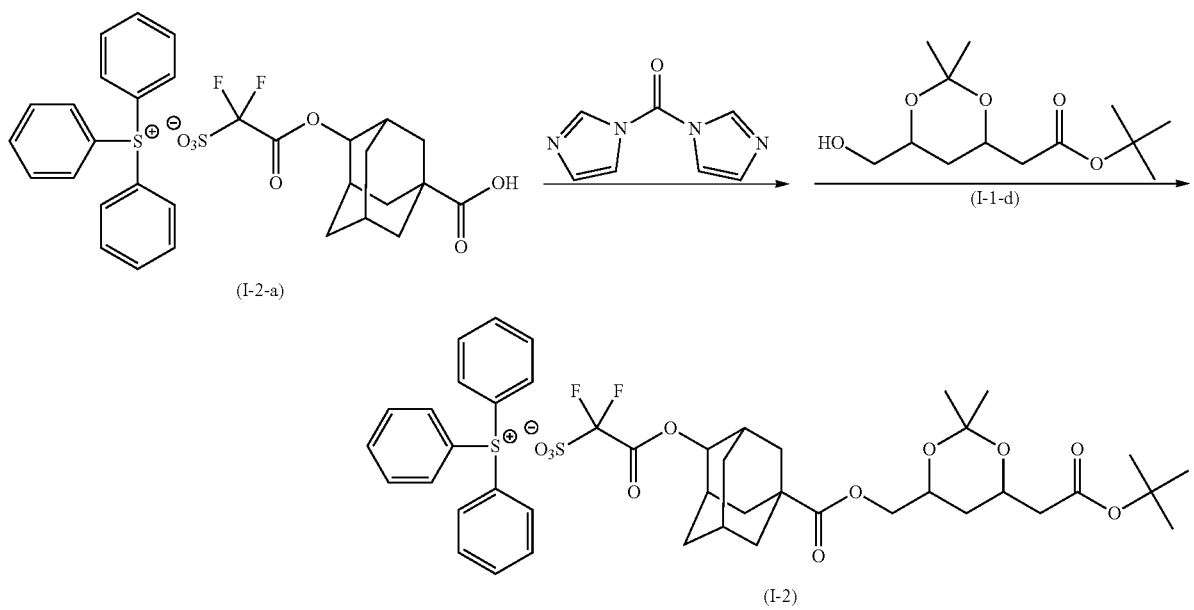

Example 4

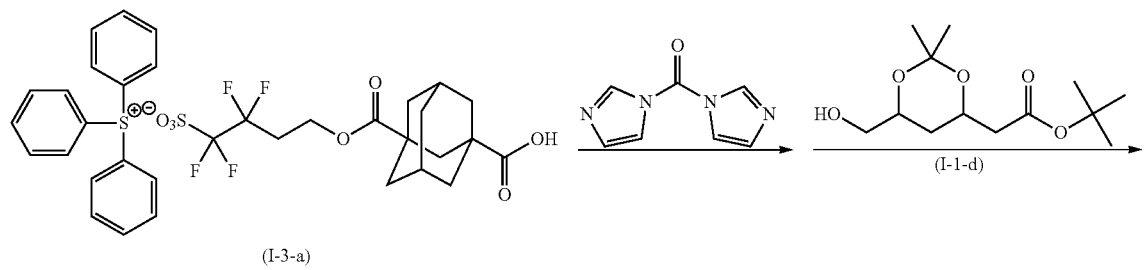

(I-3-a)      (I-1-d)

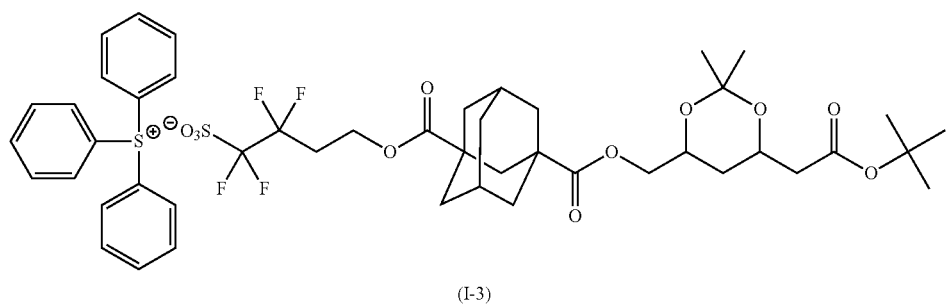

(I-3)

In a reactor, 6.94 parts of the salt represented by the formula (I-3-a), 1.7 parts of carbonyldiimidazole and 30 parts of chloroform were mixed and stirred at 23° C. for 8 hours.

To the obtained mixture, a mixture of 2.6 parts of the compound represented by the formula (I-1-d) and 10 parts of chloroform was added thereto, followed by being stirred at 23° C. for 8 hours.

To the reaction mixture, 30 parts of ion-exchanged water were added and then stirred at 23° C. for 30 minutes. Then the obtained organic layer was collected therefrom.

To the collected organic layer, 20 parts of 5% aqueous oxalic acid solution was added and then stirred at 23° C. for 30 minutes, followed by separating into an organic layer.

To the collected organic layer, 30 parts of ion-exchanged water was added and then stirred at 23° C. for 30 minutes for washing, followed by separating into an organic layer. The organic layer was washed five times as mentioned above.

Then the resultant mixture was concentrated. To the obtained residue, 30 parts of tert-butylmethylether was added and the resultant mixture was stirred at 23° C. for 30 minutes, and then its supernatant was removed therefrom. The obtained residue was concentrated to obtain 5.28 parts of the salt represented by formula (I-3).

MS (ESI(+), spectrum): M+263.1
MS (ESI(−), spectrum): M⁻ 673.2

Example 5

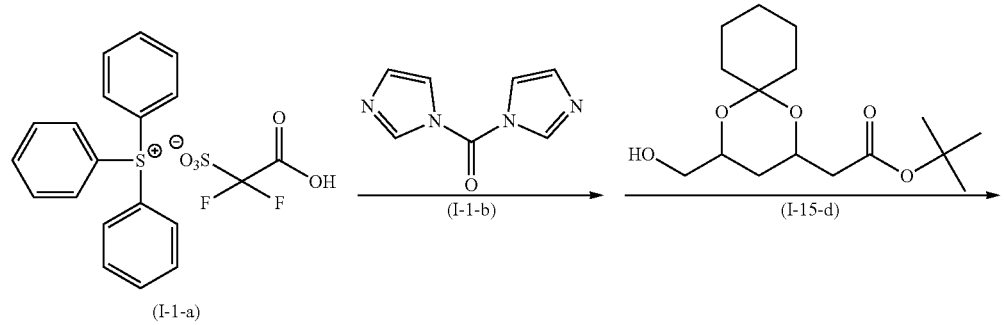

(I-1-a)      (I-1-b)      (I-15-d)

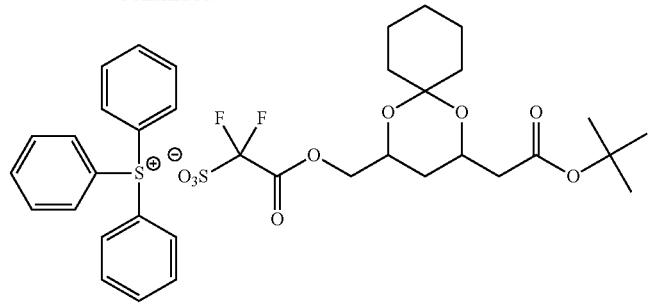

(I-15)

In a reactor, 35 parts of the salt represented by the formula (I-1-a) and 175 parts of chloroform were mixed and stirred at 23° C. for 8 hours. To the obtained mixture, 13.59 parts of carbonyldiimidazole was added and then stirred at 60° C. for one hour. The obtained reaction mixture was cooled to 23° C. and then a mixture of 28.78 parts of the compound represented by the formula (I-15-d) and 50 parts of chloroform was added thereto, followed by being stirred at 23° C. for two hours.

To the reaction mixture, 450 parts of chloroform and 150 parts of ion-exchanged water were added and then stirred at 23° C. for 30 minutes. Then the obtained organic layer was collected therefrom.

To the collected organic layer, 100 parts of 5% aqueous oxalic acid solution was added and then stirred at 23° C. for 30 minutes, followed by separating into an organic layer.

To the collected organic layer, 230 parts of ion-exchanged water was added and then stirred at 23° C. for 30 minutes for washing, followed by separating into an organic layer. The organic layer was washed five times as mentioned above.

Then the resultant mixture was concentrated. To the obtained residue, 37.5 parts of acetonitrile and 115 parts of tert-butylmethylether were added and the resultant mixture was stirred at 23° C. for 30 minutes, and then its supernatant was removed therefrom. The obtained residue was concentrated to obtain 26.22 parts of the salt represented by formula (I-15).

MS (ESI(+), spectrum): M⁺263.1

MS (ESI(−), spectrum): M⁻ 457.1

Synthesis of resin

Monomers used in the following Example are following monomers.

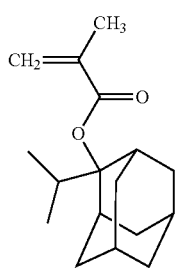

(a1-1-3)

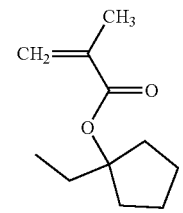

(a1-2-5)

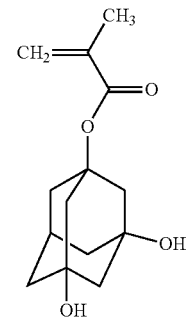

(a2-1-3)

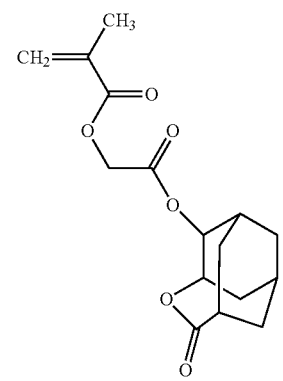

(a3-4-2)

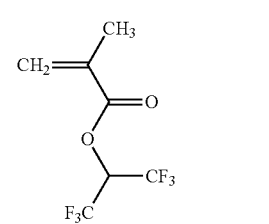

(a4-0-12)

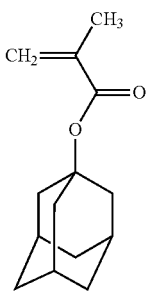

(a5-1-1)

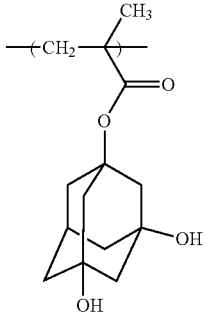

Those monomers are sometimes referred to as "Monomer (X)" in which (X) represents the sign of the formula corresponding to the monomer. For example, the monomer represented by formula (a1-1-3) is referred to as "Monomer (a1-1-3)".

Resin Synthesis Example 1

The monomers (a1-1-3), (a1-2-5), (a2-1-3) and (a3-4-2) were mixed in a molar ratio of 45/14/2.5/38.5 (monomer (a1-1-3)/monomer (a1-2-5)/monomer (a2-1-3)/monomer (a3-4-2)), and propyleneglycolmonomethyletheracetate was added in 1.5 times parts based on total parts of all monomers to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a large amount of a mixture of methanol and water to cause precipitation, followed by being filtrated.

The collected precipitate was dissolved in propyleneglycolmonomethyletheracetate, and then a large amount of the mixture of methanol and water was added thereto to cause precipitation, followed by being filtrated: This reprecipitation step was conducted twice. As a result, a polymer having a weight-average molecular weight of about 7,600 was obtained in a yield of 68%. The polymer had the following structural units. That resin is referred to as polymer A1.

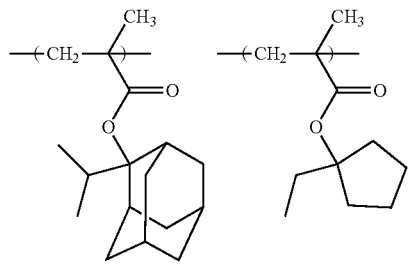

Resin Synthesis Example 2

The monomers (a5-1-1) and (a4-0-12) were mixed in a molar ratio of 50/50 (monomer (a5-1-1)/monomer (a4-0-12)), and methylisobutylketone was added in 1.2 times parts based on total parts of all monomers to prepare a mixture. To the mixture, azobisisobutyronitrile were added as an initiator in a ratio of 3 mol % based on all monomer molar amount, and the obtained mixture was heated at 70° C. for about 5 hours. The reaction mixture obtained was poured into a large amount of a mixture of methanol and water to cause precipitation, followed by being filtrated. As a result, a polymer having a weight-average molecular weight of about 10,000 was obtained in a yield of 91%. The polymer had the following structural units. That resin is referred to as polymer X1.

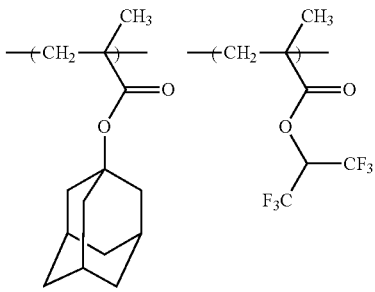

Examples 6 to 12 and Comparative Example 1
<Producing Photoresist Compositions>

The following components as listed in the following table were mixed and dissolved in the solvent as mentioned below, and then filtrated through a fluorine resin filter having pore diameter of 0.2 μm, to prepare photoresist compositions.

TABLE 5

| Comp. No. | Resin (kind/ amount (part)) | Acid generator (kind/ amount (part)) | Compound of formula (I) (kind/ amount (part)) | Quencher (kind/ amount (part)) | PB(° C.)/ PEB (° C.) |
|---|---|---|---|---|---|
| 1 | X1/0.2 A1/10 | None | I-1/1.1 | D1/0.28 | 90/85 |
| 2 | X1/0.2 A1/10 | B1-21/0.5 B1-22/0.3 | I-1/0.4 | D1/0.28 | 90/85 |

TABLE 5-continued

| Comp. No. | Resin (kind/ amount (part)) | Acid generator (kind/ amount (part)) | Compound of formula (I) (kind/ amount (part)) | Quencher (kind/ amount (part)) | PB(° C.)/ PEB (° C.) |
|---|---|---|---|---|---|
| 3 | X1/0.2 A1/10 | None | I-17/1.1 | D1/0.28 | 90/85 |
| 4 | X1/0.2 A1/10 | B1-21/0.5 B1-22/0.3 | I-17/0.4 | D1/0.28 | 90/85 |
| 5 | X1/0.2 A1/10 | None | I-2/1.1 | D1/0.28 | 90/85 |
| 6 | X1/0.2 A1/10 | None | I-3/1.1 | D1/0.28 | 90/85 |
| 7 | X1/0.2 A1/10 | None | I-15/1.1 | D1/0.28 | 90/85 |
| Compar. comp 1 | X1/0.2 A1/10 | IX-1/1.1 | None | D1/0.28 | 90/85 |

In Table 5, each of characters represents the following component:

<Resin>

A1: Resin A1, X1: Resin X1

<Salt (I)>

I-1: Salt represented by formula (I-1)

I-2: Salt represented by formula (I-2)

I-3: Salt represented by formula (I-3)

I-15: Salt represented by formula (I-15)

I-17: Salt represented by formula (I-17)

<Acid Generator>

B1-21: Salt represented by formula (B1-21), produced according to the method as recited in JP2012-224611A1

B1-22: Salt represented by formula (B1-22), produced according to the method as recited in JP2012-224611A1

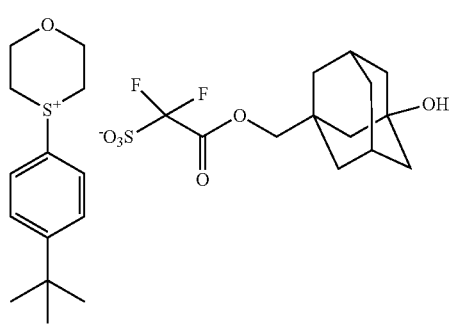

(B1-21)

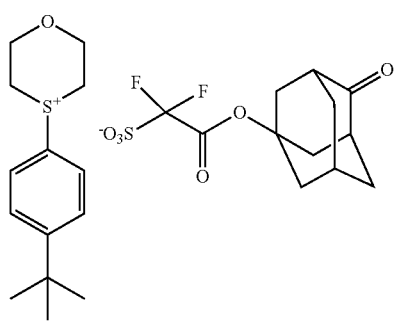

(B1-22)

X1-1: Salt represented by formula (X1-1), produced according to the method as recited in JP2012-193160A1

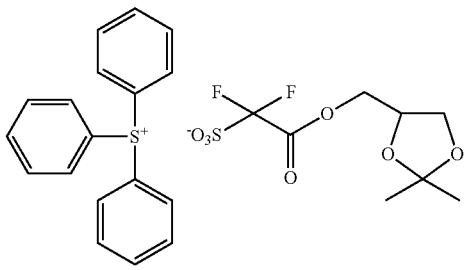

<Quencher>

D1: The compound of the following formula, which was manufactured by Tokyo Chemical Industries, Co., Ltd.

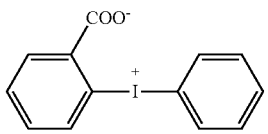

<Solvent>

Mixture of the following solvents

| | |
|---|---|
| propyleneglycolmonomethylether acetate | 265 parts |
| propyleneglycolmonomethylether | 20 parts |
| 2-heptanone | 20 parts |
| γ-butyrolactone | 3.5 parts |

<Evaluation>

Silicon wafers were each coated with "ARC-29", which is an organic anti-reflective coating composition available from Nissan Chemical Industries, Ltd., and then baked at 205° C. for 60 seconds, to form a 78 nm-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each prebaked on a direct hotplate at the temperature as listed in the column "PB" of Table 5 for 60 seconds. Using an ArF excimer stepper (XT:1900G1 manufactured by ASML INC., NA=1.35, 3/4 Annular, X-Y polarization) and a mask for forming contact hole pattern (hole pitch: 90 nm, hole diameter: 55 nm), each wafer having the respective resist film was subjected to exposure, with the exposure quantity being varied stepwise.

After the exposure, each wafer was subjected to post-exposure baking on a hotplate at the temperature as listed in the column "PEB" of Table 5 for 60 seconds and then to development for 20 seconds at 23° C. with butyl acetate (Tokyo Chemical Industries, Co., Ltd.) in the manner of dynamic dispense method to produce a negative photoresist pattern.

<Evaluation as to Critical Dimension Uniformity (CDU)>

The photoresist patterns were formed by the same method as described above in which exposure was conducted at the effective sensitivity. The hole diameter was measured at 24 points per one hole of the pattern. The average of the values determined as the hole diameter was defined as the average hole diameter of the hole.

As to the average hole diameter, the standard deviation was obtained based on the population which consisted of 400 holes within the same wafer, which was defined as CDU value.

Effective sensitivity (ES) means the exposure quantity with which exposure using the above-mentioned mask provides a pattern with 50 nm of the hole diameter after development.

TABLE 6

| Ex. No. | Composition No. | CDU value (nm) |
|---|---|---|
| Ex. 12 | 1 | 1.72 |
| Ex. 13 | 2 | 1.64 |
| Ex. 14 | 3 | 1.63 |
| Ex. 15 | 4 | 1.65 |
| Ex. 16 | 5 | 1.61 |
| Ex. 17 | 6 | 1.60 |
| Ex. 18 | 7 | 1.70 |
| Comp. Ex. 1 | Compar. Comp. 1 | 1.98 |

The salt of the present invention is useful as a component for a photoresist composition, and the photoresist composition containing the salt of the present invention can provide photoresist patterns with smaller CDU.

What is claimed is:

1. A salt represented by the formula (I):

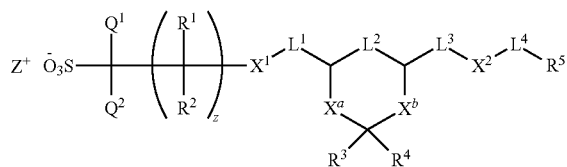

(I)

wherein $Q^1$ and $Q^2$ independently each represent a fluorine atom or a C1-C6 perfluoroalkyl group, $R^1$ and $R^2$ independently each represent a hydrogen atom, a fluorine atom or a C1-C6 perfluoroalkyl group, z represents an integer of 0 to 6, $X^1$ and $X^2$ independently each represent *—CO—O—, *—O—CO—, —O—CO—O— or —O—, where * represents a binding potion to —C($R^1$)($R^2$)—, —C($Q^1$)($Q^2$)- or $L^4$, $L^1$ represents a C1-C28 divalent saturated hydrocarbon group in which a methylene group can be replaced by —O—, —S—, —CO— or —S(O)$_2$— and in which a hydrogen atom can be replaced by a fluorine atom or a hydroxyl group, $L^2$, $L^3$ and $L^4$ independently each represent a single bond or a C1-C6 alkanediyl group, $X^a$ and $X^b$ independently each represent an oxygen atom or a sulfur atom, $R^3$ and $R^4$ independently each represent a C1-C6 alkyl group, or represent a C5-C12 alicyclic hydrocarbon ring together with a carbon atom bonded to $R^3$ and $R^4$, $R^5$ represents a hydrogen atom, a hydroxyl group, a halogen atom or a C3-C24 cyclic hydrocarbon group in which a hydrogen atom can be replaced by a substituent and in which a methylene group can be replaced by —O—, —S—, —CO— or —S(O)$_2$—, and $Z^+$ represents an organic cation.

2. The salt according to claim 1 wherein $X^1$ represents *—CO—O— or *—O—CO— where * represents a binding potion to —C($R^1$)($R^2$)— or —C($Q^1$)($Q^2$)-.

3. The salt according to claim 1 wherein $L^1$ represents a C1-C24 alkanediyl group in which a methylene group can be replaced by —O— or —CO—, or a group consisting of a divalent alicyclic hydrocarbon group and an alkanediyl group in which a methylene group can be replaced by —O— or —CO—.

4. An acid generator comprising the salt according to claim 1.

5. A photoresist composition comprising the acid generator according to claim 4 and a resin which comprises a structural unit having an acid-labile group.

6. The photoresist composition according to claim 5 which further comprises a salt generating an acid weaker in acidity than an acid generated from the acid generator.

7. A process for producing a photoresist pattern comprising the following steps (1) to (5):
(1) a step of applying the photoresist composition according to claim 5 on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

* * * * *